(12) United States Patent
Quattrocchio et al.

(10) Patent No.: US 8,629,258 B2
(45) Date of Patent: Jan. 14, 2014

(54) PLANT NUCLEIC ACIDS ASSOCIATED WITH CELLULAR PH AND USES THEREOF

(75) Inventors: Francesca Quattrocchio, Amsterdam (NL); Ronald Koes, Amsterdam (NL); Walter Verweij, Almere Buiten (NL); Filippa Brugliera, Preston (AU); Kees Spelt, Amsterdam (NL); Masako Mizutani, Kyoto (JP)

(73) Assignees: Vereniging voor Christelijk Hoger Onderwijs, Wetenschappelijk Onderzoek en Patientenzorg, Amsterdam (NL); Suntory Holdings Limited, Osaka (JP)

( * ) Notice: Subject to any disclaimer, the term of this patent is extended or adjusted under 35 U.S.C. 154(b) by 897 days.

(21) Appl. No.: 12/303,091

(22) PCT Filed: May 28, 2007

(86) PCT No.: PCT/AU2007/000739
§ 371 (c)(1),
(2), (4) Date: Jun. 4, 2009

(87) PCT Pub. No.: WO2007/137345
PCT Pub. Date: Dec. 6, 2007

(65) Prior Publication Data
US 2009/0293144 A1    Nov. 26, 2009

(30) Foreign Application Priority Data
Jun. 1, 2006    (AU) ............................ 2006902982

(51) Int. Cl.
| | | |
|---|---|---|
| C12N 15/29 | (2006.01) | |
| C12N 15/113 | (2010.01) | |
| C12N 15/82 | (2006.01) | |
| C12N 5/10 | (2006.01) | |
| A01H 5/00 | (2006.01) | |
| A01H 4/00 | (2006.01) | |
| A01H 5/02 | (2006.01) | |

(52) U.S. Cl.
USPC ......... 536/23.6; 435/419; 435/430; 536/24.5; 800/285; 800/282

(58) Field of Classification Search
None
See application file for complete search history.

(56) References Cited

U.S. PATENT DOCUMENTS

| | | | |
|---|---|---|---|
| 6,399,106 B1 * | 6/2002 | Yamasaki ..................... | 424/618 |
| 6,803,500 B1 * | 10/2004 | Iida et al. ..................... | 800/282 |
| 2003/0233670 A1 * | 12/2003 | Edgerton et al. ............. | 800/278 |
| 2005/0260754 A1 * | 11/2005 | Kock et al. ................... | 435/455 |
| 2006/0015970 A1 | 1/2006 | Pennell et al. | |
| 2006/0150283 A1 * | 7/2006 | Alexandrov et al. ......... | 800/288 |

FOREIGN PATENT DOCUMENTS

| | | |
|---|---|---|
| EP | 1 652 916 A1 | 5/2006 |
| WO | WO 92/00371 A1 | 1/1992 |
| WO | WO 92/17056 A1 | 10/1992 |
| WO | WO 93/01290 A1 | 1/1993 |
| WO | WO 93/20206 A1 | 10/1993 |
| WO | WO 94/03591 A1 | 2/1994 |
| WO | WO 94/03606 A1 | 2/1994 |
| WO | WO 94/24301 A1 | 10/1994 |
| WO | WO 96/36716 A1 | 11/1996 |
| WO | WO 97/32023 A1 | 9/1997 |
| WO | WO 01/72984 A1 | 10/2001 |
| WO | WO 03/014381 A1 | 2/2003 |
| WO | WO 03/062428 A1 | 7/2003 |
| WO | WO 2004/020637 A1 | 3/2004 |
| WO | WO 2005/017147 A1 | 2/2005 |
| WO | WO 2006/105598 A1 | 10/2006 |

OTHER PUBLICATIONS

Agrawal et al. RNA Interference: Biology, Mechanism, and Applications, 2003, Microbiol. Mol. Biol. Rev 67: 657-685.*
Mol et al. How genes paint flowers and seeds, 1998, Trends in Plant Science 3:212-217.*
Arango et al, The plasma membrane proton pump ATPase: the significant of gene subfamilies, 2003, Palnta 216:355-365.*
Guo et al, Protein tolerance to random amino acid change, 2004, PNAS 101:9205-9210.*
Condliffe et al. (2003) Acta Hort. 612: 115-120.*
Morsomme et al. (2000) Biochemica et Biophysica Acta 1469: 133-157.*
EMBL Accession No. EB175073.
EMBL Accession No. AB086373.
EMBL Accession No. AF156691.
EMBL Accession No. S79323.
EMBL Accession No. X66737.
EMBL Accession No. M27888.
EMBL Accession No. DQ334807.
Genbank Accession No. AAA34052.
Boutry et al.1989 "Molecular cloning of a family of plant genes encoding a protein homologous to plasma membrane $H^+$-translocating ATPases" *Biochemical and Biophysical Research Communications* 162(2): 567-574.
Moriau et al. 1993 "Identification and characterization of a second plasma membrane $H^+$-ATPase gene subfamily in *Nicotiana plumbaginifolia*" *Plant Molecular Biology* 21(6): 955-963.
Nakajima et al. 1995 "Isolation of cDNA for a Plasma Membrane $H^+$-ATPase from Guard Cells of *Vicia faba L.*" *Plant and Cell Physiology* 36(5):919-924.

(Continued)

*Primary Examiner* — David T Fox
*Assistant Examiner* — Steven Bernacki
(74) *Attorney, Agent, or Firm* — Knobbe Martens Olson & Bear LLP

(57) ABSTRACT

The present invention relates generally to the field of plant molecular biology and agents useful in the manipulation of plant physiological or biochemical properties. More particularly, the present invention provides genetic and proteinaceous agents capable of modulating or altering the level of acidity or alkalinity in a cell, group of cells, organelle, part or reproductive portion of a plant. Genetically altered plants, plant parts, progeny, subsequent generations and reproductive material including flowers or flowering parts having cells exhibiting an altered cellular pH compared to a non-genetically altered plant are also provided.

11 Claims, 26 Drawing Sheets

(56) References Cited

OTHER PUBLICATIONS

Oufattole et al., 2000 "Identification and expression of three new *Nicotiana plumbaginifolia* genes which encode isoforms of a plasma-membrane H+-ATPase, and one of which is induced by mechanical stress" *Planta* 210(5):715-722.

Quattrocchio et al. 2006 "PH4 of *Petunia* Is an R2R3 MYB Protein That Activates Vacuolar Acidification through Interactions with Basic-Helix-Loop-Helix Transcription Factors of the Anthocyanin Pathway" *The Plant Cell* 18:1274-1291.

Yamaguchi et al. 2001 "Genes Encoding the Vacuolar Na+/H+ Exchanger and Flower Coloration" *Plant and Cell Physiology* 42(5):451-461.

European Search Report for EP 07718985.0 dated May 26, 2009.

Database EMBL [Online] Shibuya et al., XP008092840, Database accession No. EB175073.

Database EMBL [Online] Aono et al., XP008092841, Database accession No. AB086373.

Database EMBL [Online] Oufattole et al., "Identification and expression of three new *Nicotiana plumbaginifolia* genes which encode isoforms of a plasma-membrane H+-ATPase, and the one of which is induced by mechanical stress," XP008092852, Database accession No. AF156691.

Database EMBL [Online] Nakajima et al., "Isolation of cDNA for a plasma membrane H+-ATPase from guard cells of *Vicia faba* L," XP008092844, Database accession No. S79323.

Database EMBL [Online] Moriau et al., "Identification and characterization of a second plasma membrane H+-ATPase gene subfamily in *Nicotiana plumbaginifolia*," XP008092843, Database accession No. X66737.

Database Genbank [Online] Boutry et al., "Molecular cloning of a family of plant genes encoding a protein homologous to plasma membrane H+-translocating ATPases," XP008092919, Database accession No. AAA34052.

Database EMBL [Online] Verweij et al., XP008092842, Database accession No. DQ334807.

Ohnishi Makoto et al., "Characterization of a novel Na+/H+ antiporter gene InNHX2 and comparison of InNHX2 with InNHX1, which is responsible for blue flower coloration by increasing the vacuolar pH in the Japanese morning glory," Plant and Cell Physiology, vol. 46, No. 2, Feb. 2005, pp. 259-267, XP002524880, ISSN: 0032-0781.

Quattrocchio et al., "PH4 of *Petunia* is an R2R3 MYB protein that activates vacuolar acidification through interactions with Basic-Helix-Loop-Helix transcription factors of the anthocyanine pathway," The Plant Cell, vol. 18, No. 5, May 2006, pp. 1274-1291, XP008090984.

Yamaguchi et al., "Genes encoding the vacuolar Na+/H+ exchanger and flower coloration," Plant Cell Physiology, vol. 42, No. 5, 2001, pp. 451-461, XP008090985.

Yoshida Kumi et al., "The involvement of tonoplast proton pumps and Na+(K+)/H+ exchangers in the change of petal color during flower opening of Morning Glory, *Ipomoea tricolor* cv. Heavenly Blue," Plant and Cell Physiology, vol. 46, No. 3, Mar. 2005, pp. 407-415, XP002524881, ISSN: 0032-0781.

Agrawal, N. et al. 2003 "RNA interference: biology, mechanism, and applications" *Microbiology and Molecular Biology Reviews* 67(4):657-685.

Aida, R. et al. 2004 "Efficient transgene expression in *Chrysanthemum*, *Dendranthema grandiflorum* (Ramat.) Kitamura, by using the promoter of a gene for *Chrysanthemum* chlorophyll-*a/b*-binding protein" *Breeding Science* 54:51-58.

Altschul, S.F. et al. 1997 "Gapped BLAST and PSI-BLAST: a new generation of protein database search programs" *Nucleic Acids Res* 25:3389-3402.

Arango, M. et al. 2003 "The plasma membrane proton pump ATPase: the significance of gene subfamilies" *Planta* 216:355-365.

Aswath, C.R. et al. 2004 "*IbMADS4* regulates the vegetative shoot development in transgenic *Chrysanthemum* (*Dendrathema grandiflora* (Ramat.) Kitamura)" *Plant Science* 166:847-854.

Aviv, H. and Leder, P. 1972 "Purification of biologically active globin messenger RNA by chromatography on oligothymidylic acid-cellulose" *Proc Natl Aced Sci USA* 69:1408-1412.

Baxter, I.R. et al. 2005 "A plasma membrane H+-ATPase is required for the formation of proanthocyanidins in the seed coat endothelium of *Arabidopsis thaliana*" *Proc Natl Acad Sci USA* 102:2649-2654.

Bonner, W.M. and Laskey, R.A. 1974 "A film detection method for tritium-labelled proteins and nucleic acids in polyacrylamide gels" *Eur J Biochem* 46:83-88.

Boutry, M. et al. 1989 "Molecular cloning of a family of plant genes encoding a protein homologous to plasma H+-translocating ATPases" *Biochem and Biophys Res Comm* 162:567-574.

Bruening, G. 1998 "Plant gene silencing regularized" *Proc Natl Acad Sci USA* 95:13349-13351.

Brugliera, F. et al. 1994 "Isolation and characterization of a cDNA clone corresponding to the Rt locus of *Petunia hybrida*" *The Plant Journal* 5:81-92.

Colliver, S.P. et al. 1997 "Differential modification of flavenoid and isoflavenoid biosynthesis with an antisense chalcone synthase construct and transgenic *Lotus corniculatus*" *Plant Molecular Biology* 35:509-522.

Di Sansebastiano, G.P. et al. 2001 "Regeneration of a lytic central vacuole and of neutral peripheral vacuoles can be visualized by green fluorescent proteins targeted to either type of vacuoles" *Plant Physiology* 126:78-86.

DeVetten, N. et al. 1997 "The *an11* locus controlling flower pigmentation in *Petunia* encodes a novel WD-repeat protein conserved in yeast, plants, and animals" *Genes & Development* 11: 1422-1434.

Emery, J.F. et al. 2003 "Radial patterning of *Arabidopsis* shoots by Class III HD-ZIP and KANADI genes" *Current Biology* 13:1768-1774.

Elomaa, P. et al. 1996 "Transformation of antisense constructs of the chalcone synthase gene superfamily into *Gerbera hybrida*: differential effect on the expression of family members" *Molecular Breeding* 2:41-50.

Frohman, M.A. et al. 1988 "Rapid production of full-length cDNAs from rare transcripts: Amplification using a single gene-specific oligonucleotide primer" *Proc Natl Acad Sci USA* 85:8998-9002.

Fukada-Tanaka, S. et al. 2000 "Colour-enhancing protein in blue petals" *Nature* 407:581-582.

Genbank Accession No. AY371317.

Genbank Sequence Accession No. AH008041.1, pp. 1-3, published Jul. 13, 2001.

Guo, H.H. et al. 2004 "Protein tolerance to random amino acid change" *Proc Natl Acad Sci USA* 101: 9205-9210.

Gutterson, N. 1995 "Anthocyanin biosynthetic genes and their application to flow color modification through sense suppression" *HortScience* 30:964-966.

Holton, T.A. et al. 1993 "Cloning and expression of cytochrome P450 genes controlling flower colour" *Nature* 366:276-279.

Holton, T.A. and Cornish, E.C. 1995 "Genetics and biochemistry of anthocyanin biosynthesis" *The Plant Cell* 7:1071-1083.

Jahn, T.P. et al. 2002 "Post-translational modification of plant plasma membrane H+-ATPase as a requirement for functional complementation of a yeast transport mutant" *J Biol Chem* 277:6353-6358.

Keskin, O. et al. 2004 "A new, structurally nonredundant, diverse data set of protein-protein interfaces and its implications" *Protein Science* 13:1043-1055.

Kim, C.K. et al. 2004 "*Agrobacterium tumefaciens*-mediated transformation of *Rosa hybrida* using the green fluorescent protein (GFP) gene" *Plant Cell, Tissue and Organ Culture* 78:107-111.

Koes, R. et al. 2005 "Flavenoids: a colorful model for the regulation and evolution of biochemical pathways" *Trends in Plant Science* 10:236-242.

Li, X. et al. 2002 "Optimization of the uidA gene gransfer into somatic embryos of rose via *Agrobacterium tumefaciens*" *Plant Physiol Biochem* 40:453-459.

Lu, C.-Y. et al. 1991 "*Agrobacterium*-mediated transformation of carnation (*Dianthus caryophyllus* L.)" *Biotechnology* 9:864-868.

Marchant, R. et al. 1998 "Expression of a chitinase transgene in rose (*Rosa hybrida* L.) reduces development of blackspot disease (*Diplocarpon rosae* Wolf)" *Molecular Breeding* 4:187-194.

(56) References Cited

OTHER PUBLICATIONS

Marmur, J. and Doty P. 1962 "Determination of the base composition of deoxyribonucleic acid from its thermal denaturation temperature" *J Mol Biol* 5:109-118.

Merrifield, R.B. 1963 "Solid phase peptide synthesis. I. The synthesis of a tetrapeptide" *J Amer Chem Soc* 85:2149-2154.

Mol, J. et al. 1998 "How genes paint flowers and seeds" *Trends in Plant science* 3:212-217.

Nakajima, N. et al. 1995 "Isolation of cDNA for a plasma membrane H+-ATPase from guard cells of *Vicia faba* L." *Plant Cell Physiol* 36:919-924.

Quattrocchio, F. et al. 1998 "Analysis of bHLH and MYB domain proteins: species-specific regulatory differences are caused by divergent evolution of target anthocyanin genes" *The Plant Journal* 13:475-488.

Quattrocchio, F. et al. 1999 "Molecular analysis of the *anthocyanin2* gene of *Petunia* and its role in the evolution of flower color" *The Plant Cell* 11:1433-1444.

Robinson, K.E.P. and Firoozabady, E. 1993 "Transformation of floriculture crops" *Scientia Horticulturae* 55:83-99.

Rout, G.R. et al. 1999 "Biotechnology of the rose: a review of recent progress" *Scientia Horticulturae* 81:201-228.

Short, J. et al. 1988 "λ ZAP: a bacteriophage λ expression vector with in vivo excision properties" *Nucleic Acids Research* 16:7583-7600.

Spelt, C. et al. 2002 "Anthocyanin1 of *Petunia* controls pigment synthesis, vacuolar pH, and seed coat development by genetically distinct mechanisms" *The Plant Cell* 14:2121-2135.

Tanaka, Y. et al. 2005 "Genetic engineering in floriculture" *Plant Cell Tissue and Organ Culture* 80:1-24.

Tanaka, Y. et al. in *Applied Plant Biotechnology*, "Application of Recombinant DNA to Floriculture," Copra VL, Malik VS & Bhat SR (eds), Oxford & IBH, New Delhi, 177-231, 1999.

Thorton, J.M. et al. 2000 "From structure to function: approaches and limitations" *Nature structural Biology, structural genomics supplement*: 991-994.

Teixeira Da Silva, J.A. 2003 "*Chrysanthemum*: advances in tissue culture, cryopreservation, postharvest technology, genetics and transgenic biotechnology" *Biotechnology Advances* 21:715-766.

Van Houwelingen, A. et al. 1998 "Analysis of flower pigmentation mutants generated by random transposon mutagenesis in *Petunia hybrida*" *The Plant Journal* 13:39-50.

Verdonk, J.C. et al. 2003 "Regulation of floral scent production in *Petunia* revealed by targeted metabolomics" *Phytochemistry* 62:997-1008.

De Vlaming, P. et al. 1983 "Genes affecting flower colour and pH of flower limb homogenates in *Petunia hybrida*" *Theor Appl Genet* 66:271-278.

Wells, J.A. 1990 "Additivity of mutational effects in proteins" *Biochemistry* 29:8509-8517.

Winkel-Shirley, B. 2001 "Flavenoid biosynthesis. A colorful model for genetics, biochemistry, cell biology, and biotechnology" *Plant Physiology* 126:485-493.

Winkel-Shirley, B. 2001 "It takes a garden. How work on diverse plant species has contributed to an understanding of flavonoid metabolism" *Plant Physiology* 127:1399-1404.

Yoshida, K. et al. 1995 "Cause of blue petal colour" *Nature* 373:291.

Yoshida, K. et al. 2005 "The involvement of Tonoplast proton pumps and Na+(K+)/H+ exchangers in the change of petal color during flower opening of morning glory, *Ipomoea tricolor* cv. Heavenly Blue" *Plant Cell Physiol* 46:407-415.

Genbank Accession No. AY989894.1, Jun. 1, 2005.

Harms, K. et al. 1994 "Isolation and characterization of P-type H+-ATPase genes from potato" *Plant Molecular Biology* 26: 979-988.

Harper, J.F. et al. 1990 "The *Arabidopsis thaliana* plasma membrane H+-ATPase multigene family" *J Biol Chem* 285: 13601-13608.

Harper, J.F. et al. 1994 "The plasma membrane H+-ATPase gene family in *Arabidopsis*: genomic sequence of AHA10 which is expressed primarily in developing seed." *Mol Gen Genet* 244: 572-587.

Mito, N. et al. 1996 "Sugar regulates mRNA abundance of H+-ATPase gene family members in tomato" *Plant Physiol* 112: 1229-1236.

Japanese Office Action, dated Jul. 22, 2012.

Arziman Z. et al. 2005 "E-RNAi: a web application to design optimized RNAi constructs" *Nucleic Acids Research* 33: W582-W588.

\* cited by examiner

Replicon: pK7GWIWG2(I)

Insert: PPM1-1 233bp

Replicon: pBluescript

Insert: ANS promoter and terminator

Replicon: pWTT2132

Insert: none

Replicon: pWTT2132 19.5kb XhoI (blunt)

Insert: ~4.3kb carnation ANS PPM1 RNAi cassette

Replicon: pCGP2355 26.8kb HincII (blunt)

Insert: ~4.3kb carnation ANS PPM1 RNAi cassette HincII (blunt)

Replicon: pRTppoptcAFP EcoRI/XbaI
3.3kb

Insert: multicloning site from pNEB193
EcoRI/XbaI ~40bp

Replicon: pBinPLUS 12.3kb HindIII

Insert: ~1.7kb carnation 35S PPM1 RNAi cassette

Replicon: pCGP2355 26.8kb HincII (blunt)

Insert: ~1.67kb carnation 35S PPM1 RNAi cassette HincII (blunt)

```
GCTTCGTCGCAGAGGAGGAGGAGGAGGAAGAAGGAAGAAGGAAGGAGCTTCGTCCCTCTTCCCGCGCTTCCGA
AATACTTGGATACTGATTGGAAGCTCGAATCATGGCTGAAGATCTGGACAAACCGTTGTTGGATCCTGAGAAT
TTCAATAGAGATGGCATCGATTTGGAACGCTTACCCCTGGAAGAAGTTTTTGAACAACTGAGAACATCAGCGA
GAGGACTTTCATCCGATGATGCTGAAGCCAGATTGCACATTTTTGGCTACAACAAACTTGAAGAGAAGACAGA
GAACAAAATTTTGAAGTTTCTTAGCTTTATGTGGAACCCCTTGTCATGGGTTATGGAAGCTGCAGCAGTTATG
GCACTTGTCCTTGCTAATGGGGAGGTGAGGGTCCTGACTGGCAAGACTTTGTTGGATTATTGTCCTATTAA
TAATCAATTCAACAATTAGTTTCATAGAGGAGAATAATGCGGGAAATGCTGCATCAGCTCTTATGGAACGTTT
ATCTCCAAAGACAAGGGTTCTCAGAGATGGGCAGTGGCAAGAGCAAGATGCAGGTATTTTAGTGCCAGGAGAC
ATAATTAGCATAAAGCTCGGGGATATAATTCCAGCTGATGCTCGTCTACTTGAAGGAGACCCTCTGAAAGTTG
ATCAGTCGGCTCTTACAGGAGAGTCTCTGGCTGTCACCAAGAGGACAGGTGATGAAGTATTTCTGGTTCAAC
ATGTAAGCATGGAGAAATTGAAGCTGTAGTGATAGCAACCGGAGTTCACTCATTTTTGGAAAAGCAGCACAT
TTAGTCGACACCACTGAAGTTGTGGGACATTTCCAGCAGGTCCTTACTGCCATTGGGAATTTCTGCATTTGCT
CTATAGCTGTGGGAATGGTTCTTGAAATCATTGTCATGTTCCCCATACAGCAACGTTCTTACAGGGATGGAAT
CAACAACCTTCTTGTTCTCTTAATTGGAGGAATTCCAATTGCTATGCCAACAGTGTTATCTGTGACACTTGCA
ATTGGTTCTCATCGACTATCTCAACAGGGTGCTATTACAAAAAGGATGACAGCAATTGAAGAAATGGCGGGAA
TGGATGTCCTTTGTAGTGACAAAACTGGAACTCTTACCCTGAACCGCCTCACTGTTGATAAAAACCTGGTTGA
GGTTTTTAACAATAATATAGACAGAGACACAGTTATCTTATTTGCAGCCAGAGCAGCAAGACTGGAGAATCAA
GACGCAATTGATGCAGCCATTACCAATATGCTTGGTGATCCAAAGGAGGCACGTGCAAACATTACCGAAGTGC
ATTTTCTGCCCTTCAATCCAGTGGACAAGCGTACTGCCATTACATACATCGACTCTGATGGTAATTGGTATAG
GGCCAGCAAAGGAGCTCCAGAACAGATTCTAGATCTTTGCCCTGAGAAAAATGAGATTGCTGGAAGAGTACAT
AGCACCATTGACAAATTTGCTGAAAGAGGCTTGCGGTCTCTTGGAGTTGCTTATCAGGAAGTTCCAGAAAAAA
CTAAAGAAAGCCCTGCCGGTCCTTGGACCTTTTGTGGGTTGTTGCCCTTGTTTGATCCTCCGAGGCATGACAG
TGCTGAGACCATTCGTAGAGCACTTAACCTTGGAGTCGCTGTGAAGATGATTACAGGTGACCAGTTGGCAATT
GCGAAGGAGACAGGGAGACGGCTTGGTATGGGAACAAACATGTATCCTTCCTCTTCATTATTGGGCCGCAAAA
AAGAAGAAGACCACGAAGCCGTGCCAGTGGACGAGCTGATTGAGAAGGCAGATGGCTTTGCTGGTGTCTTCC
CTGAACACAAGTATGAAATTGTAAAAATCTTACAAGAAAAGAAGCATGTCGTTGGAATGACTGGAGATGGCGT
TAACGATGCACCTGCTTTAAAGAAAGCAGACATTGGTATAGCAGTGGCAGATTCCACAGATGCTGCGAGAAGT
GCTTCTGATATAGTCTTAACGGAACCTGGCTTAAGTGTCATTGTCAGTGCTGTCCTGACCAGTCGAGCTATAT
TCCAGAGAATGAAGAATTATACTATATATGCTGTTTCCATTACCATTAGGATTGTGCTTGGTTTCGTGCTTCT
TGCATTGATATGGGAGTATGATTTCCCACCTTTCATGGTTCTGATTATAGCAATACTGAATGATGGGACCATC
ATGACAATTTCCCAAGATCGGGTAAAGCCCTCTCCAAAGCCTGACAGTTGGAAGTTGAATGAGATATTTGCAA
CTGGCATTGTCATTGGTACATATCTAGCTTTGGTTACTGTGTTATTTTACTGGACTGTCATTGAGACCACCTT
CTTTGAGGACACCCTTTGGCTTAATGTCTATATCCGACAACAGTGAGGAAGTTTCATCTGCTGTATATCTGCAA
GTTAGCATCATAAGTCAAGCTCTCATATTTGTTACCCGAAGTCAAGGATGGTCATTTCTTGAGAGACCTGGAG
CTCTGTTGATGATTCATTTGTTGTGGCTCAACTGGTGGCTACTCTGATTGCCGTCTATGCGGAAATCAGCTT
TGCTTACATTAGCGGCATTGGATGGGATGGGCTGGAGTCATATGGTTGTATAGTTTGATTTCTACTTCCCC
TTGGACATTATCAAGTTCGCAATTCGCTATGCCTTGAGTGGAGATGCCTGGAATTTATTGTTTGATAGAAAGA
CAGCTTTTACTGCTAAGAAAGATTATGGGAAGGAAGACAGGGCAGCTAAATGGGTACTTTCTCAGAGAACTTT
ACAGGGGTTGCATGACATGGAGTTCAAGGCAGGTAGAACTAGCCCCAAAAATGCTGGTTGGATTGCCGAACAG
GCCAGACGGCGCGCTGAAATAGCCAGGTTGGGAGAGCTACACACTATGAGAGGACATGTAGAATCTGTAATGA
GGCTAAAAAATTTGGACCCGAACGTTATTTCCGCCCACACAGTCTGAAGCCAATACATGGAGACAGTAGTATT
CAATTTTCTGGTGAAAGAAAATTCTGCAGCATTTGCTCACATAATTGATGTTTGGGTATCTGCAAAAGAAATT
GACATTTGGTTACCAGATTTTTTTTGGGATGGCGTAGGTAACTCTCTGTAATGTTGTCAATTCTTTGGGTGC
TAAAAGTAAGGAGTATATTTTCCTAGTATTAATTTGTCTTAATTTTCAATGTATACAAGGGGACCTTCTGTTT
TTGTGTAATAATTAGGCTACTTGAAACTAATAAACCCACATGCTAGAGTGGAATTTTC
```

Figure 21

```
> NAME = '1-2 protein.fa' : TYPE = Protein
MAEDLDKPLLDPENFNRDGIDLERLPLEEVFEQLRTSARGLSSDDAEARLHIFGYNKLEEKTENKILKFLSFM
WNPLSWVMEAAAVMALVLANGGGEGPDWQDFVGIIVLLIINSTISFIEENNAGNAASALMERLSPKTRVLRDG
QWQEQDAGILVPGDIISIKLGDIIPADARLLEGDPLKVDQSALTGESLAVTKRTGDEVFSGSTCKHGEIEAVV
IATGVHSFFGKAAHLVDTTEVVGHFQQVLTAIGNFCICSIAVGMVLEIIVMFPIQQRSYRDGINNLLVLLIGG
IPIAMPTVLSVTLAIGSHRLSQQGAITKRMTAIEEMAGMDVLCSDKTGTLTLNRLTVDKNLVEVFNNNIDRDT
VILFAARAARLENQDAIDAAITNMLGDPKEARANITEVHFLPFNPVDKRTAITYIDSDGNWYRASKGAPEQIL
DLCPEKNEIAGRVHSTIDKFAERGLRSLGVAYQEVPEKTKESPGGPWTFCGLLPLFDPPRHDSAETIRRALNL
GVAVKMITGDQLAIAKETGRRLGMGTNMYPSSSLLGRKKEEDHEAVPVDELIEKADGFAGVFPEHKYEIVKIL
QEKKHVVGMTGDGVNDAPALKKADIGIAVADSTDAARSASDIVLTEPGLSVIVSAVLTSRAIFQRMKNYTIYA
VSITIRIVLGFVLLALIWEYDFPPFMVLIIAILNDGTIMTISQDRVKPSPKPDSWKLNEIFATGIVIGTYLAL
VTVLFYWTVIETTFFEDTFGLMSISDNSEEVSSAVYLQVSIISQALIFVTRSQGWSFLERPGALLMIAFVVAQ
LVATLIAVYAEISFAYISGIGWGWAGVIWLYSLIFYFPLDIIKFAIRYALSGDAWNLLFDRKTAFTAKKDYGK
EDRAAKWVLSQRTLQGLHDMEFKAGRTSPKNAGWIAEQARRRAEIARLGELHTMRGHVESVMRLKNLDPNVIS
AHTV
```

Figure 22

Replicon: pBluescript SK (-) vector

Insert: ~3.3kb Rose PPM1 cDNA clone

SEQ ID NO:2   1 MAEDLERPLLGPDNFSREGIDLEKLPLEQVFEELRTSKEGLSDEDAEERL 50
SEQ ID NO:99  1 MAEDLDKPLLDPENFNRDGIDLERLPLEEVFEQLRTSARGLSSDDAEARL 50
                ***..*.*.**.*.***..*.**...*..*.

SEQ ID NO:2   51 NIFGPNKLEEKRENKFIKFLGFMWNPLSWVMEAAAIMAIALANGGGQGPD 100
SEQ ID NO:99  51 HIFGYNKLEEKTENKILKFLSFMWNPLSWVMEAAAVMALVLANGGGEGPD 100
                 .* ** * .* ********** . **** *

SEQ ID NO:2   101 WQDFVGIVCLLLINSTISFIEENNAGNAAAALMARLAPRTKVLRDGRWQE 150
SEQ ID NO:99  101 WQDFVGIIVLLIINSTISFIEENNAGNAASALMERLSPKTRVLRDGQWQE 150
                  *****. .****************.* **.*.*.***.*

SEQ ID NO:2   151 KDAAILVPGDIISIKLGDIIPADARLLEGDPLKVDQSALTGESLPVTKKT 200
SEQ ID NO:99  151 QDAGILVPGDIISIKLGDIIPADARLLEGDPLKVDQSALTGESLAVTKRT 200
                  . **************************************** *.*

SEQ ID NO:2   201 GDEVFSGSTCKHGEIEAVVIATGVHSFFGKAAHLVDSTQVTGHFQKVLAS 250
SEQ ID NO:99  201 GDEVFSGSTCKHGEIEAVVIATGVHSFFGKAAHLVDTTEVVGHFQQVLTA 250
                  ************************************.*.* **...

SEQ ID NO:2   251 IGNFCICSIAMGMILEIIVMFPVQNRSYRTGINNLLVLLIGGIPIAMPTV 300
SEQ ID NO:99  251 IGNFCICSIAVGMVLEIIVMFPIQQRSYRDGINNLLVLLIGGIPIAMPTV 300
                  ********..*******.*.** ******************

SEQ ID NO:2   301 LSVTLAIGSHRLSQQGAITKRMTAIEEMAGMDVLCSDKTGTLTLNRLTID 350
SEQ ID NO:99  301 LSVTLAIGSHRLSQQGAITKRMTAIEEMAGMDVLCSDKTGTLTLNRLTVD 350
                  ************************************************.*

SEQ ID NO:2   351 RNLIEVFQKDMDKDMVVLLAARASRLENQDAIDAAVINMLADPKEARANI 400
SEQ ID NO:99  351 KNLVEVFNNNIDRDTVILFAARAARLENQDAIDAAITNMLGDPKEARANI 400
                  ..*. .*.*.*.*.*.* **.*******. * *********

Figure 24A

SEQ ID NO:2   401 REVHFLPFNPVDKRTAITYIDSDGKWYRASKGAPEQILTLCQEKQQIAAK 450
SEQ ID NO:99  401 TEVHFLPFNPVDKRTAITYIDSDGNWYRASKGAPEQILDLCPEKNEIAGR 450
                  ******************.**********.  ..  .

SEQ ID NO:2   451 VHTIIDKFAERGLRSLAVSFQEIPENSKESPGGPWQFCGLLPLFDPPRHD 500
SEQ ID NO:99  451 VHSTIDKFAERGLRSLGVAYQEVPEKTKESPGGPWTFCGLLPLFDPPRHD 500
                  .******** .....*****.************

SEQ ID NO:2   501 SAETIRRALNLGVCVKMITGDQLAIAKETGRRLGMGTNMYPSCSLFGRDK 550
SEQ ID NO:99  501 SAETIRRALNLGVAVKMITGDQLAIAKETGRRLGMGTNMYPSSSLLGRKK 550
                  ***********.***********************. ** *

SEQ ID NO:2   551 DE-TEALPVDELIEKADGFAGVFPEHKYEIVKILQMNEHVVGMTGDGVND 599
SEQ ID NO:99  551 EEDHEAVPVDELIEKADGFAGVFPEHKYEIVKILQEKKHVVGMTGDGVND 600
                  .*   .*********************     *********

SEQ ID NO:2   600 APALKKADIGIAVADATDAARSAADLVLTEPGLSVIVSAVLTSRAIFQRM 649
SEQ ID NO:99  601 APALKKADIGIAVADSTDAARSASDIVLTEPGLSVIVSAVLTSRAIFQRM 650
                  *************.*****.*.************************

SEQ ID NO:2   650 KNYTIYAVSITIRIVLGFMLLALIWKYDFPPFMVLIIAILNDGTIMTISK 699
SEQ ID NO:99  651 KNYTIYAVSITIRIVLGFVLLALIWEYDFPPFMVLIIAILNDGTIMTISQ 700
                  ****************.**.*********************.

SEQ ID NO:2   700 DRVKPSPRPDSWKLNEIFATGVVLGTYLALVTVLFYWLADSTQFFEAHFH 749
SEQ ID NO:99  701 DRVKPSPKPDSWKLNEIFATGIVIGTYLALVTVLFYWTVIETTFFEDTFG 750
                  *****.***********.*.*************    *  ***  *

SEQ ID NO:2   750 VKSLSGSSEEMSSAVYLQVSIISQALIFVTRSQSWSFTERPGALLMFAFV 799
SEQ ID NO:99  751 LMSISDNSEEVSSAVYLQVSIISQALIFVTRSQGWSFLERPGALLMIAFV 800
                  . *.*   *.***************** * ******.*

SEQ ID NO:2   800 VAQLVATLIAVYAHISFASVRGIGWGWAGVIWLYSLIFYIPLDIIKFAVC 849
SEQ ID NO:99  801 VAQLVATLIAVYAEISFAYISGIGWGWAGVIWLYSLIFYFPLDIIKFAIR 850
                  ***********.  . *************.******..

Figure 24B

```
SEQ ID NO:2   850 YALTGEAWNLLFDKKTAFTSKKDYGREDREAQWVLSQRSLQRVISPEFEP 899
SEQ ID NO:99  851 YALSGDAWNLLFDRKTAFTAKKDYGKEDRAAKWVLSQRTLQGLHDMEFKA 900
                  ***.*.*******.*****.*****.*** *.******.**  .   **

SEQ ID NO:2   900 RSRRPS---MIAEQAKRRAEITRLRELYTLRGHIESVARLKNLDLNKIQT 946
SEQ ID NO:99  901 GRTSPKNAGWIAEQARRRAEIARLGELHTMRGHVESVMRLKNLDPNVIS- 949
                    *        *****.*****.** ** *.***.*** ****** * *

SEQ ID NO:2   947 AHTV* 951
              SEQ ID NO:99  950 AHTV  953
                                ****
```

Figure 24C

PLANT NUCLEIC ACIDS ASSOCIATED WITH CELLULAR PH AND USES THEREOF

This application is U.S. National Phase of International Application PCT/AU2007/000739, filed May 28, 2007 designating the U.S., and published in English as WO 2007/137345 on Dec. 6, 2007, which claims priority to Australian Patent Application No. 2006902982, filed Jun. 1, 2006.

FIELD

The present invention relates generally to the field of plant molecular biology and agents useful in the manipulation of plant physiological or biochemical properties. More particularly, the present invention provides genetic and proteinaceous agents capable of modulating or altering the level of acidity or alkalinity in a cell, group of cells, organelle, part or reproductive portion of a plant. Genetically altered plants, plant parts, progeny, subsequent generations and reproductive material including flowers or flowering parts having cells exhibiting an altered cellular pH compared to a non-genetically altered plant are also provided.

BACKGROUND

Reference to any prior art in this specification is not, and should not be taken as, an acknowledgment or any form of suggestion that this prior art forms part of the common general knowledge in any country.

Bibliographic details of references provided in the subject specification are listed at the end of the specification.

The cut-flower, ornamental and agricultural plant industries strive to develop new and different varieties of plants with features such as novel flower colors, better taste/flavor of fruits (e.g. grapes, apples, lemons, oranges) and berries (e.g. strawberries, blueberries), improved yield, longer life, more nutritious, novel colored seeds for use as proprietary tags, etc.

Furthermore, plant byproduct industries which utilize plant parts value novel products which have the potential to impart altered characteristics to their products (e.g. juices, wine) such as, appearance, style, taste, smell and texture.

In the cut flower and ornamental plant industries, an effective way to create such novel varieties is through the manipulation of flower color. Classical breeding techniques have been used with some success to produce a wide range of colors for almost all of the commercial varieties of flowers and/or plants available today. This approach has been limited, however, by the constraints of a particular species' gene pool and for this reason it is rare for a single species to have the full spectrum of colored varieties. For example, the development of novel colored varieties of plants or plant parts such as flowers, foliage and stems would offer a significant opportunity in both the cut flower and ornamental markets. In the cut flower or ornamental plant industry, the development of novel colored varieties of major flowering species such as rose, chrysanthemum, tulip, lily, carnation, gerbera, orchid, lisianthus, begonia, torenia, geranium, petunia, nierembergia, pelargonium, iris, impatiens and cyclamen would be of great interest. A more specific example would be the development of a blue rose for the cut flower market.

To date, creation of a "true" blue shade in cut flowers has proven to be extremely difficult. Success in creating colors in the "blue" range has provided a series of purple colored carnation flowers (see the website for Florigene Pty Ltd, Melbourne, Australia; and International Patent Application PCT/AU96/00296). These are now on the market in several countries around the world. There is a need, however, to generate altered flower colors in other species in addition to bluer colors in carnation and other cut flower species such as *Rosa* sp., *Dianthus* sp., *Gerbera* sp., *Chrysanthemum* sp., *Dendranthema* sp., lily, *Gypsophila* sp., *Torenia* sp., *Petunia* sp., orchid, *Cymbidium* sp., *Dendrobium* sp., *Phalaenopsis* sp., *Cyclamen* sp., *Begonia* sp., *Iris* sp., *Alstroemeria* sp., *Anthurium* sp., *Catharanthus* sp., *Dracaena* sp., *Erica* sp., *Ficus* sp., *Freesia* sp., *Fuchsia* sp., *Geranium* sp., *Gladiolus* sp., *Helianthus* sp., *Hyacinth* sp., *Hypericum* sp., *Impatiens* sp., *Iris* sp., *Chamelaucium* sp., *Kalanchoe* sp., *Lisianthus* sp., *Lobelia* sp., *Narcissus* sp., *Nierembergia* sp., *Ornithoglaum* sp., *Osteospermum* sp., *Paeonia* sp., *Pelargonium* sp., *Plumbago* sp., *Primrose* sp., *Ruscus* sp., *Saintpaulia* sp., *Solidago* sp., *Spathiphyllum* sp., *Tulip* sp., *Verbena* sp., *Viola* sp., *Zantedeschia* sp. etc. It is apparent that other plants have been recalcitrant to genetic manipulation of flower color due to certain physiological characteristics of the cells. One such physiological characteristics is vacuolar pH.

In all living cells, the pH of the cytoplasm is about neutral, whereas in the vacuoles and lysosomes an acidic environment is maintained. The $H^+$-gradient across the vacuolar membrane is a driving force that enables various antiporters and symporters to transport compounds across the vacuolar membrane. The acidification of the vacuolar lumen is an active process. Physiological work indicated that two proton pumps, a vacuolar $H^+$ pumping ATPase (vATPase) and a vacuolar pyrophosphatase (V-PPase), are involved in vacuolar acidification.

Vacuoles have many different functions and different types of vacuoles may perform these different functions.

The existence of different vacuoles also opens complementary questions about vacuole generation and control of the vacuolar content. The studies devoted to finding an answer to this question are complicated by the fact that isolation and evacuolation of cells (protoplast isolation and culture) induces stress that results in changes in the nature of the vacuolar environment and content.

Mutants in which the process of vacuolar genesis and/or the control of the internal vacuolar environment are affected are highly valuable to allow the study of these phenomena in intact cells in the original tissue. Mutants of this type are not well described in the literature. This has hampered research in this area.

Flower color is predominantly due to three types of pigment: flavonoids, carotenoids and betalains. Of the three, the flavonoids are the most common and contribute a range of colors from yellow to red to blue. The flavonoid pigments are secondary metabolites of the phenylpropanoid pathway. The biosynthetic pathway for the flavonoid pigments (flavonoid pathway) is well established, (Holton and Cornish, *Plant Cell* 7:1071-1083, 1995; Mol et al, *Trends Plant Sci.* 3: 212-217, 1998; Winkel-Shirley, *Plant Physiol.* 126:485-493, 2001a; Winkel-Shirley, *Plant Physiol.* 127:1399-1404, 2001b, Tanaka et al, *Plant Cell, Tissue and Organ Culture* 80 (1):1-24, 2005, Koes et al, *Trends in Plant Science*, May 2005).

The flavonoid molecules that make the major contribution to flower or fruit color are the anthocyanins, which are glycosylated derivatives of anthocyanidins. Anthocyanins are generally localized in the vacuole of the epidermal cells of petals or fruits or the vacuole of the sub epidermal cells of leaves. Anthocyanins can be further modified through the addition of glycosyl groups, acyl groups and methyl groups. The final visible color of a flower or fruit is generally a combination of a number of factors including the type of anthocyanin accumulating, modifications to the anthocyanidin molecule, co-pigmentation with other flavonoids such as flavonols and flavones, complexation with metal ions and the pH of the vacuole.

The vacuolar pH is a factor in anthocyanin stability and color. Although a neutral to alkaline pH generally yields bluer anthocyanidin colors, these molecules are less stable at this pH.

Vacuoles, occupy a large part of the plant cell volume and play a crucial role in the maintenance of cell homeostasis. In mature cells, these organelles can approach 90% of the total cell volume, can store a large variety of molecules (ions, organic acids, sugar, enzymes, storage proteins and different types of secondary metabolites) and serve as reservoirs of protons and other metabolically important ions. Different transporters on the membrane of the vacuoles regulate the accumulation of solutes in this compartment and drive the accumulation of water producing the turgor of the cell. These structurally simple organelles play a wide range of essential roles in the life of a plant and this requires their internal environment to be tightly regulated.

There is a need to be able to manipulate the pH in plant cells and organelles in order to generate desired flower colors.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides a nucleic acid molecule derived, obtainable or from rose plants encoding a polypeptide having pH modulating or altering activity and to the use of the nucleic acid molecule and/or corresponding polypeptide to generate genetic agents or constructs or other molecules which manipulate the pH in a cell, groups of cells, organelles, parts or reproductions of a plant. Manipulation of vacuolar pH is a particular embodiment. Controlling the pH pathway, and optionally, together with manipulation of the anthocyanin pathway provides a powerful technique to generate altered colors or other traits such as taste or flavor, especially in rose, carnation, gerbera, chrysanthemum, lily, gypsophila, apple, begonia, *Euphorbia*, pansy, *Nierembergia*, lisianthus, grapevine, Kalanchoe, pelargonium, *Impatiens*, *Catharanthus*, cyclamen, *Torenia*, orchids, *Petunia*, iris, *Fuchsia*, lemons, oranges, grapes and berries (such as strawberries, blueberries)

Accordingly, a genetic agents and proteinaceous agents are provided which increase or decrease the level of acidity or alkalinity in a plant cell. The ability to alter pH enables manipulation of flower color. The agents include nucleic acid molecules such as cDNA and genomic DNA or parts or fragments thereof, antisense, sense or RNAi molecules or complexes comprising same, ribozymes, peptides and proteins. In a particular embodiment, the vacuolar pH is altered.

Another aspect relates to a nucleic acid molecule comprising a sequence of nucleotides encoding or complementary to a sequence encoding a protein which exhibits a direct or indirect effect on cellular pH, and in particular vacuolar pH. Generally the nucleic acid is derived from rose plants.

Levels of expression of the subject nucleic acid molecule to be manipulated or to be introduced into a plant cell alter cellular pH, and in particular vacuolar pH. This in turn permits flower color or taste or other characteristics to be manipulated.

Genetically modified plants are provided exhibiting altered flower color or taste or other characteristics. Reference to genetically modified plants includes the first generation plant or plantlet as well as vegetative propagants and progeny and subsequent generations of the plant. Reference to a "plant" includes reference to plant parts including reproductive portions, seeds, flowers, stems, leaves, stalks, pollen and germ plasm, callus including immature and mature callus.

A particular aspect described herein relates to down regulation of the pH modulating or altering genetic and proteinaceous agents capable of modulating or altering the level of acidity or alkalinity, leading to an increase in cellular, and in particular vacuolar, pH in a plant, resulting in bluer colored flowers in the plant.

Cut flowers are also provided including severed stems containing flowers of the genetically altered plants or their progeny in isolated form or packaged for sale or arranged on display.

The nucleic acid molecule and polypeptide encoded thereby from rose is particularly contemplated herein together with a rose nucleic acid sequence or polypeptide in combination with sequences from plants such as gerbera, chrysanthemum and carnation. A summary of sequence identifiers used throughout the subject specification is provided in Table 1:

TABLE 1

Summary of sequence identifiers

| SEQ ID NO: | Sequence name | Type of sequence | Description |
| --- | --- | --- | --- |
| 1 | MAC F55.nt | nucleotide | *Petunia* PPM1 cDNA clone |
| 2 | MAC F55.aa | amino acid | Deduced amino acid sequence of *Petunia* PPM1 cDNA nucleotide sequence |
| 3 | MAC 9F1.nt | nucleotide | *Petunia* MAC9F1 cDNA clone |
| 4 | MAC 9F1.aa | amino acid | Deduced amino acid sequence of *Petunia* MAC 9F1 nucleotide sequence |
| 5 | CAC 16.5.nt | nucleotide | *Petunia* cysteine proteinase cDNA clone |
| 6 | CAC 16.5.aa | amino acid | Deduced amino acid sequence of *Petunia* cysteine proteinase nucleotide sequence |
| 7 | Mse A1 | nucleotide | primer |
| 8 | MseA2 | nucleotide | primer |
| 9 | mse + 0 | nucleotide | primer |
| 10 | Mse + A | nucleotide | primer |
| 11 | Mse + C | nucleotide | primer |

TABLE 1-continued

Summary of sequence identifiers

| SEQ ID NO: | Sequence name | Type of sequence | Description |
|---|---|---|---|
| 12 | Mse + G | nucleotide | primer |
| 13 | Mse + T | nucleotide | primer |
| 14 | Eco + A1 | nucleotide | primer |
| 15 | Eco + A2 | nucleotide | primer |
| 16 | Eco + A | nucleotide | primer |
| 17 | Eco + C | nucleotide | primer |
| 18 | Eco + G | nucleotide | primer |
| 19 | Eco + T | nucleotide | primer |
| 20 | Mse + AA | nucleotide | primer |
| 21 | Mse + AC | nucleotide | primer |
| 22 | Mse + AG | nucleotide | primer |
| 23 | Mse + AT | nucleotide | primer |
| 24 | Mse + CA | nucleotide | primer |
| 25 | Mse + CC | nucleotide | primer |
| 26 | Mse + CG | nucleotide | primer |
| 27 | Mse + CT | nucleotide | primer |
| 28 | Mse + GA | nucleotide | primer |
| 29 | Mse + GC | nucleotide | primer |
| 30 | Mse + GG | nucleotide | primer |
| 31 | Mse + GT | nucleotide | primer |
| 32 | Mse + TA | nucleotide | primer |
| 33 | Mse + TC | nucleotide | primer |
| 34 | Mse + TG | nucleotide | primer |
| 35 | Mse + TT | nucleotide | primer |
| 36 | Eco + AA | nucleotide | primer |
| 37 | Eco + AC | nucleotide | primer |
| 38 | Eco + AG | nucleotide | primer |
| 39 | Eco + AT | nucleotide | primer |
| 40 | Eco + CA | nucleotide | primer |
| 41 | Eco + CC | nucleotide | primer |
| 42 | Eco + CG | nucleotide | primer |
| 43 | Eco + CT | nucleotide | primer |
| 44 | Eco + GA | nucleotide | primer |
| 45 | Eco + GC | nucleotide | primer |
| 46 | Eco + GG | nucleotide | primer |
| 47 | Eco + GT | nucleotide | primer |
| 48 | Eco + TA | nucleotide | primer |
| 49 | Eco + TC | nucleotide | primer |
| 50 | Eco + TG | nucleotide | primer |
| 51 | Eco + TT | nucleotide | primer |
| 52 | 1702 | nucleotide | primer |
| 53 | 1703 | nucleotide | primer |
| 54 | 1741 | nucleotide | primer |
| 55 | 1742 | nucleotide | primer |
| 56 | 1750 | nucleotide | primer |
| 57 | 1788 | nucleotide | primer |
| 58 | 1789 | nucleotide | primer |
| 59 | 1812 | nucleotide | primer |
| 60 | 1831 | nucleotide | primer |
| 61 | 1832 | nucleotide | primer |
| 62 | 1847 | nucleotide | primer |
| 63 | 1848 | nucleotide | primer |
| 64 | 1861 | nucleotide | primer |
| 65 | 1864 | nucleotide | primer |
| 66 | 1885 | nucleotide | primer |
| 67 | 1886 | nucleotide | primer |
| 68 | 1956 | nucleotide | primer |
| 69 | 2035 | nucleotide | primer |
| 70 | 2037 | nucleotide | primer |
| 71 | 2038 | nucleotide | primer |
| 72 | 2039 | nucleotide | primer |
| 73 | 2040 | nucleotide | primer |
| 74 | 2073 | nucleotide | primer |
| 75 | 2075 | nucleotide | primer |
| 76 | 2078 | nucleotide | primer |
| 77 | 2123 | nucleotide | primer |
| 78 | 2124 | nucleotide | primer |
| 79 | 2196 | nucleotide | primer |
| 80 | 2270 | nucleotide | primer |
| 81 | 2271 | nucleotide | primer |
| 82 | 1706 | nucleotide | primer |
| 83 | 1707 | nucleotide | primer |
| 84 | 1743 | nucleotide | primer |
| 85 | 1768 | nucleotide | primer |
| 86 | 1876 | nucleotide | primer |
| 87 | 1877 | nucleotide | primer |

TABLE 1-continued

Summary of sequence identifiers

| SEQ ID NO: | Sequence name | Type of sequence | Description |
|---|---|---|---|
| 88 | 1878 | nucleotide | primer |
| 89 | 2061 | nucleotide | primer |
| 90 | 2101 | nucleotide | primer |
| 91 | 2178 | nucleotide | primer |
| 92 | 1654 | nucleotide | primer |
| 93 | 1655 | nucleotide | primer |
| 94 | 1769 | nucleotide | primer |
| 95 | 1770 | nucleotide | primer |
| 96 | 1870 | nucleotide | primer |
| 97 | 1871 | nucleotide | Primer |
| 98 | 1-2contig.fa | nucleotide | Rose PPM1 cDNA clone |
| 99 | 1-2protein.fa | amino acid | Deduced amino acid sequence of Rose PPM1 cDNA clone |
| 100 | #2124: 5' | nucleotide | primer |
| 101 | #2078: 5' | nucleotide | primer |
| 102 | 1969 | nucleotide | primer |
| 103 | 1970 | nucleotide | primer |
| 104 | rosePPM F1 | nucleotide | primer |
| 105 | rosePPM F2 | nucleotide | primer |
| 106 | rosePPM F3 | nucleotide | primer |
| 107 | rosePPM R1 | nucleotide | primer |

BRIEF DESCRIPTION OF THE FIGURES

FIG. 21 is a representation of rose PPM1 nucleotide sequence (SEQ ID NO: 98).

FIG. 22 is a representation of rose PPM1 amino acid sequence (SEQ ID NO: 99).

FIG. 24 is a ClustalW (v1.4) multiple sequence alignment of SEQ ID NO: 2 (deduced amino acid sequence of petunia PPM1) and SEQ ID NO: 99 (deduced amino acid sequence of rose PPM1). Alignment Score=5014, Gaps Inserted=3, Conserved Identities=795, Pairwise Alignment Parameters: Open Gap Penalty=10.0, Extend Gap Penalty=0.1, Similarity Matrix: blosum, Aligned Length=955, Gaps=3, Identities=795 (83%) and Similarities=77 (8%). "*" represent identical residues and "." represent conservative substitutions

DETAILED DESCRIPTION

Figure 1:
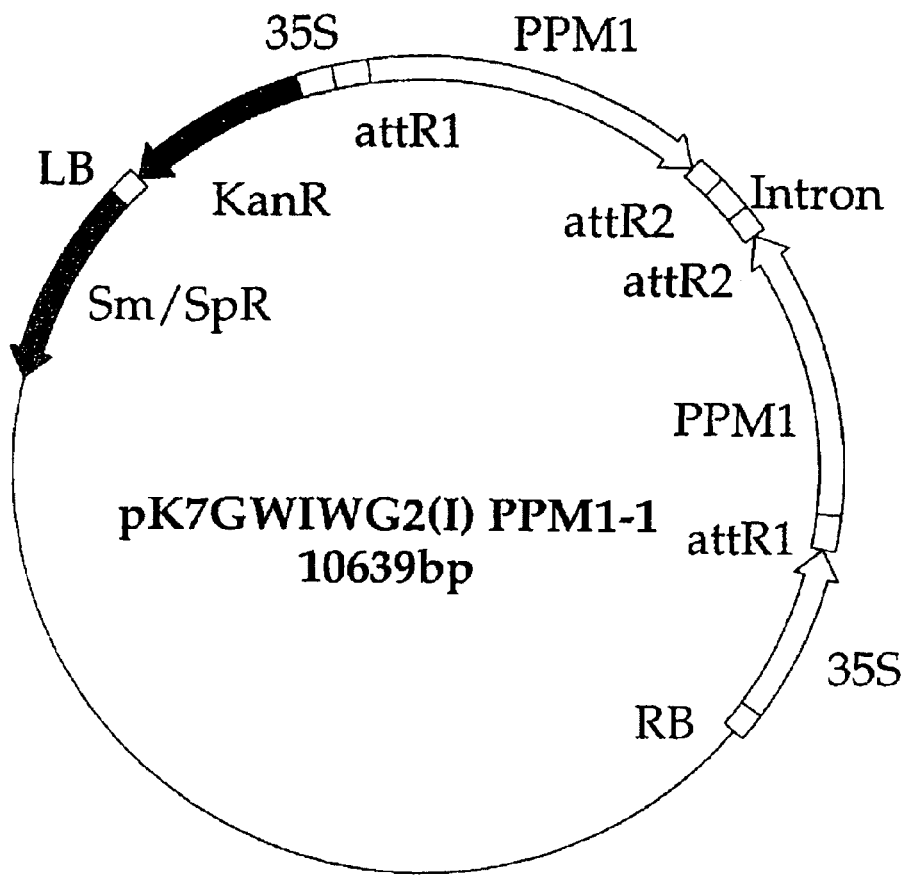
FIG. 1 is a diagrammatical representation of replicon pK7GWIWG2(I) PPM1-1 10639bp.

Nucleic acid sequences encoding polypeptides having pH modulating or altering activities have been identified, cloned and assessed. The recombinant genetic sequences described herein permit the modulation of expression of genes or nucleic acids encoding pH modulating or altering activities by, for example, de novo expression, over-expression, sense suppression, antisense inhibition, ribozyme, minizyme and DNAzyme activity, RNAi-induction or methylation-induction or other transcriptional or post-transcriptional silencing activities. RNAi-induction includes genetic molecules such as hairpin, short double stranded DNA or RNA, and partially double stranded DNAs or RNAs with one or two single stranded nucleotide over hangs. The ability to control cellular pH and in particular vacuolar pH in plants thereby enables the manipulation of petal color in response to pH change. Moreover, plants and reproductive or vegetative parts thereof are contemplated herein including flowers, fruits, seeds, vegetables, leaves, stems and the like. Other aspects include ornamental transgenic or genetically modified plants. The term "transgenic" also includes vegetative propagants and progeny plants and plants from subsequent genetic manipulation and/or crosses thereof from the primary transgenic plants.

Accordingly, one aspect provides an isolated nucleic acid molecule comprising a sequence of nucleotides encoding or complementary to a sequence encoding a pH modulating or altering gene or a polypeptide having pH modulating or altering activity wherein expression of said nucleic acid molecule alters or modulates pH inside the cell. In one aspect, the pH is altered in the vacuole.

More particularly, an isolated nucleic acid molecule derived from rose is provided comprising a sequence of nucleotides encoding or complementary to a sequence encoding a pH modulating or altering gene or a polypeptide having pH modulating or altering activity wherein expression of said nucleic acid molecule alters or modulates pH inside the cell.

In a particular embodiment, the nucleic acid modulates vacuolar pH.

Another aspect contemplates an isolated nucleic acid molecule comprising a sequence of nucleotides encoding or complementary to a sequence encoding a pH modulating or altering gene operably linked to a nucleic acid sequence comprising a sequence of nucleotides encoding or complementary to a sequence encoding an anthocyanin pathway gene.

More particularly, an isolated nucleic acid molecule is provided derived from rose comprising a sequence of nucleotides encoding or complementary to a sequence encoding a pH modulating or altering gene operably linked to a nucleic acid sequence comprising a sequence of nucleotides encoding or complementary to a sequence encoding an anthocyanin pathway gene.

Another aspect of the present invention is directed to an isolated nucleic acid molecule obtainable from rose comprising a sequence of nucleotides encoding or complementary to a sequence encoding a pH modulating or altering gene operably linked to a nucleic acid sequence comprising a sequence of nucleotides encoding or complementary to a sequence encoding an anthocyanin pathway gene.

Homologous nucleic acid molecules and proteins from chrysanthemum, gerbera and carnation are also contemplated.

Reference to "derived" in relation to the nucleic acid molecule from rose or other plants means isolated directly from the plant, is obtainable from a plant, is obtained indirectly via a nucleic acid library in a virus, bacterium or other cell or was originally from the plant but is maintained by a different plant.

By the term "nucleic acid molecule" is meant a genetic sequence in a non-naturally occurring condition. Generally, this means isolated away from its natural state or synthesized or derived in a non-naturally-occurring environment. More specifically, it includes nucleic acid molecules formed or maintained in vitro, including genomic DNA fragments recombinant or synthetic molecules and nucleic acids in combination with heterologous nucleic acids. It also extends to the genomic DNA or cDNA or part thereof encoding pH modulating sequences or a part thereof in reverse orientation relative to its own or another promoter. It further extends to naturally occurring sequences following at least a partial purification relative to other nucleic acid sequences.

The term "genetic sequences" is used herein in its most general sense and encompasses any contiguous series of nucleotide bases specifying directly, or via a complementary series of bases, a sequence of amino acids in a pH modulating protein. Such a sequence of amino acids may constitute a full-length pH modulating or altering enzyme such as is set forth in SEQ ID NO: 99 or an amino acid sequence having at least 50% similarity thereto such as SEQ ID NO:2, 4 or 6, or an active truncated form thereof or may correspond to a particular region such as an N-terminal, C-terminal or internal portion of the enzyme. A genetic sequence may also be referred to as a sequence of nucleotides or a nucleotide sequence and includes a recombinant fusion of two or more sequences.

In accordance with the above aspects of the present invention there is provided a nucleic acid molecule comprising a nucleotide sequence or complementary nucleotide sequence substantially as set forth in SEQ ID NO:98 or having at least about 50% similarity thereto or capable of hybridizing to the sequence set forth in SEQ ID NO: 98 under low stringency conditions such as SEQ ID NO:1, 3 or 5.

The anthocyanin pathway genes optionally contemplated to be used in conjunction with the pH modulating or altering nucleic acids, set forth in SEQ ID NO:98 or 1, 3 or 5 or having at least about 50% similarity or identity thereto or capable of hybridizing to the sequence set forth in SEQ ID NO:98 or 1, 3 or 5 under low stringency conditions, have been previously described, for example, patents and patent application for the families relating to PCT/AU92/00334; PCTAU96/00296; PCT/AU93/00127; PCT/AU97/00124; PCT/AU93/00387; PCT/AU93/00400; PCT/AU01/00358; PCT/AU03/00079; PCT/AU03/01111 and JP 2003-293121.

Table 1 provides a summary of the sequence identifiers. The nucleotide and corresponding amino acid sequence of rose PPM1 is provided in FIGS. 21 and 22 and in SEQ ID NOs:98 and 99, respectively. The present invention further extends to homologous nucleic acids and proteins from chrysanthemum, gerbera and carnation.

Alternative percentage similarities and identities (at the nucleotide or amino acid level) encompassed by the present invention include at least about 60% or at least about 65% or at least about 70% or at least about 75% or at least about 80% or at least about 85% or at least about 90% or above, such as about 95% or about 96% or about 97% or about 98% or about 99%, such as at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In a particular embodiment, there is provided an isolated nucleic acid molecule comprising a nucleotide sequence or complementary nucleotide sequence substantially as set forth in SEQ ID NO:98 or having at least about 50% similarity thereto or capable of hybridizing to the sequence set forth in SEQ ID NO:98 or complementary strands of either under low stringency conditions, wherein said nucleotide sequence encodes a polypeptide having pH modulating or altering activity.

For the purposes of determining the level of stringency to define nucleic acid molecules capable of hybridizing to SEQ ID NO:98 reference herein to a low stringency includes and encompasses from at least about 0% to at least about 15% v/v formamide and from at least about 1M to at least about 2 M salt for hybridization, and at least about 1 M to at least about 2 M salt for washing conditions. Generally, low stringency is from about 25-30° C. to about 42° C. The temperature may be altered and higher temperatures used to replace the inclusion of formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 1.0% w/v SDS at 25-42° C.; a moderate stringency is 2×SSC buffer, 1.0% w/v SDS at a temperature in the range 20° C. to 65° C.; high stringency is 0.1×SSC buffer, 0.1% w/v SDS at a temperature of at least 65° C.

Another aspect of the present invention provides a nucleic acid molecule comprising a sequence of nucleotides encoding or complementary to a sequence encoding an amino acid sequence substantially as set forth in SEQ ID NO:99 or an amino acid sequence having at least about 50% similarity thereto.

The term similarity as used herein includes exact identity between compared sequences at the nucleotide or amino acid level. Where there is non-identity at the nucleotide level, similarity includes differences between sequences which result in different amino acids that are nevertheless related to each other at the structural, functional, biochemical and/or conformational levels. Where there is non-identity at the amino acid level, similarity includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al, (*Nucl. Acids Res.* 25: 3389-3402, 1997). A detailed discussion of sequence analysis can be found in Unit 19.3 of Ausubel et al, *Current Protocols in Molecular Biology* John Wiley & Sons Inc, 1994-1998, Chapter 15, 1998.

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The nucleic acid sequences contemplated herein also encompass oligonucleotides useful as genetic probes for amplification reactions or as antisense or sense molecules capable of regulating expression of the corresponding gene in a plant. Sense molecules include hairpin constructs, short double stranded DNAs and RNAs and partially double stranded DNAs and RNAs which one or more single stranded nucleotide over hangs. An antisense molecule as used herein may also encompass a genetic construct comprising the structural genomic or cDNA gene or part thereof in reverse orientation relative to its own or another promoter. It may also encompass a homologous genetic sequence. An antisense or sense molecule may also be directed to terminal or internal portions of the gene encoding a polypeptide having a pH modulating or altering activity or to combinations of the above such that the expression of the gene is reduced or eliminated.

With respect to this aspect, there is provided an oligonucleotide of 5-50 nucleotides such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 having substantial similarity to a part or region of a molecule with a nucleotide sequence set forth in SEQ ID NO:98. By substantial similarity or complementarity in this context is meant a hybridizable similarity under low, alternatively and preferably medium and alternatively and most preferably high stringency conditions specific for oligonucleotide hybridization (Sambrook et al, *Molecular Cloning: A Laboratory Manual, 2nd* edition, Cold Spring Harbor Laboratories, Cold Spring Harbor, N.Y., USA, 1989). Such an oligonucleotide is useful, for example, in screening for pH modulating or altering genetic sequences from various sources or for monitoring an introduced genetic sequence in a transgenic plant. The preferred oligonucleotide is directed to a conserved pH modulating or altering genetic sequence or a sequence conserved within a plant genus, plant species and/or plant variety.

In one aspect, the oligonucleotide corresponds to the 5' or the 3' end of the nucleic acid modulating or altering pH sequences. For convenience, the 5' end is considered herein to define a region substantially between the start codon of the structural gene to a centre portion of the gene, and the 3' end is considered herein to define a region substantially between the centre portion of the gene and the terminating codon of the structural gene. It is clear, therefore, that oligonucleotides or probes may hybridize to the 5' end or the 3' end or to a region common to both the 5' and the 3' ends. The present invention extends to all such probes.

In one embodiment, the nucleic acid sequence encoding a pH modulating or altering proteins or various functional derivatives thereof is used to reduce the level of an endogenous pH modulating or altering protein (e.g. via co-suppression or antisense-mediated suppression) or other post-transcriptional gene silencing (PTGS) processes including RNAi or alternatively the nucleic acid sequence encoding this enzyme or various derivatives or parts thereof is used in the sense or antisense orientation to reduce the level of a pH modulating or altering protein. The use of sense strands, double or partially single stranded such as constructs with hairpin loops is particularly useful in inducing a PTGS response. In a further alternative, ribozymes, minizymes or DNAzymes could be used to inactivate target nucleic acid sequences.

Still a further embodiment encompasses post-transcriptional inhibition to reduce translation into polypeptide material. Still yet another embodiment involves specifically inducing or removing methylation.

Reference herein to the changing of a pH modulating or altering activity relates to an elevation or reduction in activity of up to 30% or more preferably of 30-50%, or even more preferably 50-75% or still more preferably 75% or greater above or below the normal endogenous or existing levels of activity. Such elevation or reduction may be referred to as modulation or alteration of a pH modulating protein. Often, modulation is at the level of transcription or translation of pH modulating or altering genetic sequences.

The nucleic acids may be a ribonucleic acid or deoxyribonucleic acids, single or double stranded and linear or covalently closed circular molecules. Preferably, the nucleic acid molecule is cDNA. The present invention also extends to other nucleic acid molecules which hybridize under low, preferably under medium and most preferably under high stringency conditions with the nucleic acid molecules of the present invention and in particular to the sequence of nucleotides set forth in SEQ ID NO:98 or a part or region thereof. In a particular embodiment, a nucleic acid molecule is provided having a nucleotide sequence set forth in SEQ ID NO:98 or to a molecule having at least 40%, more preferably at least 45%, even more preferably at least 55%, still more preferably at least 65%-70%, and yet even more preferably greater than 85% similarity at the level of nucleotide or amino acid sequence to at least one or more regions of the sequence set forth in SEQ ID NO:98 and wherein the nucleic acid encodes or is complementary to a sequence which encodes an enzyme having a pH modulating or altering activity. It should be noted, however, that nucleotide or amino acid sequences may have similarities below the above given percentages and yet still encode a pH modulating or altering activity and such molecules may still be considered in the scope of the present invention where they have regions of sequence conservation. Another aspect extends to nucleic acid molecules in the form of oligonucleotide primers or probes capable of hybridizing to a portion of the nucleic acid molecules contemplated above, and in particular those set forth in SEQ ID NO:98, under low, particularly under medium and most particularly under high stringency conditions. Preferably the portion corresponds to the 5' or the 3' end of the gene. For convenience the 5' end is considered herein to define a region substantially between the start codon of the structural genetic sequence to a centre portion of the gene, and the 3' end is considered herein to define a region substantially between the centre portion of the gene and the terminating codon of the structural genetic sequence. It is clear, therefore, that oligonucleotides or probes may hybridize to the 5' end or the 3' end or to a region common to both the 5' and the 3' ends. All such probes are contemplated herein.

The term gene is used in its broadest sense and includes cDNA corresponding to the exons of a gene. Accordingly, reference herein to a gene is to be taken to include:—
(i) a classical genomic gene consisting of transcriptional and/or translational regulatory sequences and/or a coding region and/or non-translated sequences (i.e. introns, 5'- and 3'-untranslated sequences); or
(ii) mRNA or cDNA corresponding to the coding regions (i.e. exons) and 5'- and 3'-untranslated sequences of the gene.

The term gene is also used to describe synthetic or fusion molecules encoding all or part of an expression product. In particular embodiments, the term nucleic acid molecule and gene may be used interchangeably.

The nucleic acid or its complementary form may encode the full-length enzyme or a part or derivative thereof. By "derivative" is meant any single or multiple amino acid substitutions, deletions, and/or additions relative to the naturally occurring enzyme and which retains a pH modulating or altering activity. In this regard, the nucleic acid includes the naturally occurring nucleotide sequence encoding a pH modulating or altering activity or may contain single or multiple nucleotide substitutions, deletions and/or additions to said naturally occurring sequence. The nucleic acid of the present invention or its complementary form may also encode a "part" of the pH modulating or altering protein, whether active or inactive, and such a nucleic acid molecule may be useful as an oligonucleotide probe, primer for polymerase chain reactions or in various mutagenic techniques, or for the generation of antisense molecules.

Reference herein to a "part" of a nucleic acid molecule, nucleotide sequence or amino acid sequence, preferably relates to a molecule which contains at least about 10 contiguous nucleotides or five contiguous amino acids, as appropriate.

Amino acid insertional derivatives of the pH modulating or altering protein of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Typical substitutions are those made in accordance with Table 2.

TABLE 2

Suitable residues for ammo acid substitutions

| Original residue | Exemplary substitutions |
|---|---|
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

Where the pH modulating or altering protein is derivatized by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, *J. Am. Chem. Soc.* 85:2149, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al, 1989 supra.

Other examples of recombinant or synthetic mutants and derivatives of the pH modulating or altering proteins described herein include single or multiple substitutions, deletions and/or additions of any molecule associated with the enzyme such as carbohydrates, lipids and/or proteins or polypeptides.

The terms "analogs" and "derivatives" also extend to any functional chemical equivalent of pH modulating or altering proteins and also to any amino acid derivative described above. For convenience, reference to pH modulating or altering proteins herein includes reference to any functional mutant, derivative, part, fragment, homolog or analog thereof.

Nucleic acid sequences derived from rose are particularly exemplified herein since this represents a convenient source of material to date. However, one skilled in the art will immediately appreciate that similar sequences can be isolated from any number of sources such as other plants or certain microorganisms. All such nucleic acid sequences encoding directly or indirectly a pH modulating protein are encompassed herein regardless of their source. Examples of other suitable sources of genes encoding pH modulating or altering proteins include, but are not limited to Liparieae, *Plumbago* spp, *Rosa* sp., *Gerbera* sp., *Chrysanthemum* sp., *Dendranthema* sp., lily, *Gypsophila* sp., *Torenia* sp., *Petunia* sp., orchid, *Cymbidium* sp., *Dendrobium* sp., *Phalaenopsis* sp., cyclamen, *Begonia* sp., *Iris* sp., *Alstroemeria* sp., *Anthurium* sp., *Catharanthus* sp., *Dracaena* ap., *Erica* sp., *Ficus* sp., *Freesia* sp., *Fuchsia* sp., *Geranium* sp., *Gladiolus* sp., *Helianthus* sp., *Hyacinth* sp., *Hypericum* sp., *Impatiens* sp., *Iris* sp., *Chamelaucium* sp., *Kalanchoe* sp., *Lisianthus* sp., *Lobelia* sp., *Narcissus* sp., *Nierembergia* sp., *Ornithoglaum* sp., *Osteospermum* sp., *Paeonia* sp., *Pelargonium* sp., *Primrose* sp., *Ruscus* sp., *Saintpaulia* sp., *Solidago* sp., *Spathiphyllum* sp., *Tulip* sp., *Verbena* sp., *Viola* sp., *Zantedeschia* sp. etcanenome, hyacinth, *Liatrus* sp., *Viola* sp., *Nierembergia* sp. and *Nicotiana* sp. etc.

A nucleic acid sequence is described herein encoding a pH modulating or altering protein may be introduced into and expressed in a transgenic plant in either orientation thereby providing a means to modulate or alter the vacuolar pH by either reducing or eliminating endogenous or existing pH modulating or altering protein activity thereby allowing the vacuolar pH to increase. A particular effect is a visible effect of a shift to blue in the color of the anthocyanins and/or in the resultant flower color. Expression of the nucleic acid sequence in the plant may be constitutive, inducible or developmental and may also be tissue-specific. The word "expression" is used in its broadest sense to include production of RNA or of both RNA and protein. It also extends to partial expression of a nucleic acid molecule.

According to this aspect, there is provided a method for producing a transgenic flowering plant capable of synthesizing a pH modulating or altering protein, said method comprising stably transforming a cell of a suitable plant with a nucleic acid sequence which comprises a sequence of nucleotides encoding said pH modulating or altering proteins under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous pH modulating or altering proteins at elevated levels relative to the amount expressed in a comparable non-transgenic plant.

Another aspect contemplates a method for producing a transgenic plant with reduced indigenous or existing pH modulating or altering activity, said method comprising stably transforming a cell of a suitable plant with a nucleic acid molecule which comprises a sequence of nucleotides encoding or complementary to a sequence encoding a pH modulating activity, regenerating a transgenic plant from the cell and where necessary growing said transgenic plant under conditions sufficient to permit the expression of the nucleic acid.

Yet another aspect provides a method for producing a genetically modified plant with reduced indigenous or existing pH modulating or altering protein activity, said method comprising altering the pH modulating or altering gene through modification of the indigenous sequences via homologous recombination from an appropriately altered pH modulating or altering gene or derivative or part thereof introduced into the plant cell, and regenerating the genetically modified plant from the cell.

Still another aspect contemplates a method for producing a genetically modified plant with reduced indigenous pH altering protein activity, said method comprising altering the pH by reducing expression of a gene encoding the indigenous pH altering protein by introduction of a nucleic acid molecule into the plant cell and regenerating the genetically modified plant from the cell.

Yet another aspect provides a method for producing a transgenic plant capable of generating a pH altering protein, said method comprising stably transforming a cell of a suitable plant with the isolated nucleic acid molecule obtainable from rose comprising a sequence of nucleotides encoding, or complementary to, a sequence encoding a pH and regenerating a transgenic plant from the cell.

As used herein an "indigenous" enzyme is one, which is native to or naturally expressed in a particular cell. A "non-indigenous" enzyme is an enzyme not native to the cell but expressed through the introduction of genetic material into a plant cell, for example, through a transgene. An "endogenous" enzyme is an enzyme produced by a cell but which may or may not be indigenous to that cell.

As indicated above, a particular nucleic acid molecule encoding a protein which alters pH is from rose.

In a particular embodiment, a method for producing a transgenic flowering plant exhibiting altered floral or inflorescence properties is contemplated, said method comprising stably transforming a cell of a suitable plant with a nucleic acid sequence obtainable or derived from rose, regenerating a transgenic plant from the cell and growing said transgenic plant for a time and under conditions sufficient to permit the expression of the nucleic acid sequence.

The term "inflorescence" as used herein refers to the flowering part of a plant or any flowering system of more than one flower which is usually separated from the vegetative parts by an extended internode, and normally comprises individual flowers, bracts and peduncles, and pedicels. As indicated above, reference to a "transgenic plant" may also be read as a "genetically modified plant".

Alternatively, the method may comprise stably transforming a cell of a suitable plant with a nucleic acid sequence obtainable or derived from rose, or its complementary sequence, regenerating a transgenic plant from the cell and growing said transgenic plant for a time and under conditions sufficient to alter the level of activity of the indigenous or existing pH modulating or altering proteins. In one embodiment, the altered level would be less than the indigenous or existing level of pH modulating or altering activity in a comparable non-transgenic plant. Without wishing to commit to one theory or mode of action is that reduction of the indigenous pH modulating protein activity may require the expression of the introduced nucleic acid sequence or its complementary sequence. However, expression of the introduced genetic sequence or its complement may not be required to achieve the desired effect: namely, a flowering plant exhibiting altered floral or inflorescence properties.

In a related embodiment, a method is provided for producing a flowering plant exhibiting altered floral or inflorescence properties, said method comprising alteration of the pH modulating or altering gene through modification of the indigenous sequences via homologous recombination from an appropriately altered pH modulating or altering gene or derivative or part thereof introduced into the plant cell, and regenerating the genetically modified plant from the cell.

In a particular aspect, the altered floral or inflorescence includes the production of different shades of blue or purple or red flowers or other colors, depending on the genotype and physiological conditions of the recipient plant. In another aspect, the target gene is from rose.

Accordingly, a method is contemplated for producing a transgenic plant capable of expressing a recombinant gene derived from rose encoding a pH modulating or altering protein or part thereof or which carries a nucleic acid sequence which is substantially complementary to all or a part of a mRNA molecule encoding a pH modulating or altering protein, said method comprising stably transforming a cell of a suitable plant with the isolated nucleic acid molecule comprising a sequence of nucleotides encoding, or complementary to a sequence encoding, a pH modulating or altering protein, where necessary under conditions permitting the eventual expression of said isolated nucleic acid molecule, and regenerating a transgenic plant from the cell.

One skilled in the art will immediately recognise the variations applicable to the methods described herein, such as increasing or decreasing the expression of the enzyme naturally present in a target plant leading to differing shades of colors such as different shades of blue, purple or red.

The instant disclosure, therefore, extends to all transgenic plants or parts or cells therefrom of transgenic plants or progeny of the transgenic plants containing all or part of the nucleic acid sequences of the present invention, or antisense forms thereof and/or any homologs or related forms thereof and, in particular, those transgenic plants which exhibit altered floral or inflorescence properties. The transgenic plants may contain an introduced nucleic acid molecule comprising a nucleotide sequence encoding or complementary to a sequence encoding a pH modulating or altering protein. Generally, the nucleic acid would be stably introduced into the plant genome, although the present invention also extends to the introduction of a pH modulating or altering nucleotide sequence within an autonomously-replicating nucleic acid sequence such as a DNA or RNA virus capable of replicating within the plant cell. This aspect also extends to seeds from such transgenic plants. Such seeds, especially if colored, are useful as proprietary tags for plants. Any and all methods for introducing genetic material into plant cells including but not limited to *Agrobacterium*-mediated transformation, biolistic particle bombardment etc. are encompassed herein.

Another aspect contemplates the use of the extracts from transgenic plants or plant parts or cells therefrom of transgenic plants or progeny of the transgenic plants containing all or part of the nucleic acid sequences described herein and in particular rose such as when used as a flavoring or food additive or health product or beverage or juice or coloring.

Plant parts contemplated herein include, but are not limited to flowers, fruits, vegetables, nuts, roots, stems, leaves or seeds.

The extracts may be derived from the plants or plant part or cells therefrom in a number of different ways including but not limited to chemical extraction or heat extraction or filtration or squeezing or pulverization.

The plant, plant part or cells therefrom or extract can be utilized in any number of different ways such as for the production of a flavoring (e.g. a food essence), a food additive (e.g. a stabilizer, a colorant) a health product (e.g. an antioxidant, a tablet) a beverage (e.g. wine, spirit, tea) or a juice (e.g. fruit juice) or coloring (e.g. food coloring, fabric coloring, dye, paint, tint).

A further aspect is directed to recombinant forms of pH modulating or altering proteins such as from rose. The recombinant forms of the enzyme provide a source of material for research, for example, more active enzymes and may be useful in developing in vitro systems for production of colored compounds.

Still a further aspect contemplates the use of the genetic sequences described herein such as from rose in the manufacture of a genetic construct capable of expressing a pH modulating or altering protein or down-regulating an indigenous pH modulating protein in a plant.

The term genetic construct has been used interchangeably throughout the specification and claims with the terms "fusion molecule", "recombinant molecule", "recombinant nucleotide sequence". A genetic construct may include a single nucleic acid molecule comprising a nucleotide sequence encoding a single protein or may contain multiple open reading frames encoding two or more proteins. It may also contain a promoter operably linked to one or more of the open reading frames.

Another aspect is directed to a prokaryotic or eukaryotic organism carrying a genetic sequence encoding a pH modulating or altering proteins such as from rose extrachromasomally in plasmid form.

A recombinant polypeptide is also provided comprising a sequence of amino acids substantially as set forth in SEQ ID NO:99 or an amino acid sequence having at least about 50% similarity to SEQ ID NO:99 or a derivative of said polypeptide.

A "recombinant polypeptide" means a polypeptide encoded by a nucleotide sequence introduced into a cell directly or indirectly by human intervention or into a parent or other relative or precursor of the cell. A recombinant polypeptide may also be made using cell-free, in vitro transcription systems. The term "recombinant polypeptide" includes an isolated polypeptide or when present in a cell or cell preparation. It may also be in a plant or parts of a plant regenerated from a cell which produces said polypeptide.

A "polypeptide" includes a peptide or protein and is encompassed by the term "enzyme".

The recombinant polypeptide may also be a fusion molecule comprising two or more heterologous amino acid sequences.

Still yet another aspect contemplates a pH modulating or altering nucleic acid sequence linked to a nucleic acid sequence involved in modulating or altering the anthocyanin pathway.

Another aspect is direct to the use of a nucleic acid molecule obtainable from rose which encodes a pH altering polypeptide in the manufacture of a plant with an altered pH compared to the pH in a non-manufactured plant of the same species. In a particular embodiment, the vacuolar pH is altered.

The present invention is further described by the following non-limiting Examples.

In relation to these Examples, the following methods and agents are employed:

In general, the methods followed were as described in Sambrook et al, 1989 supra or Sambrook and Russell, Molecular Cloning: A Laboratory Manual 3$^{rd}$ edition, Cold Spring Harbor Laboratories, Cold Spring Harbor, N.Y., USA, 2001 or Plant Molecular Biology Manual (2$^{nd}$ edition), Gelvin and Schilperoot (eds), Kluwer Academic Publisher, The Netherlands, 1994 or Plant Molecular Biology Labfax, Croy (ed), Bios scientific Publishers, Oxford, UK, 1993.

Stages of Flower Development

*Petunia hybrida* cv. M1×V30 flowers were harvested at developmental stages defined as follows:
Stage 1: Unpigmented flower bud (less than 10 mm in length)
Stage 2: Unpigmented flower bud (10 to 20 mm in length)
Stage 3: Lightly pigmented closed flower bud (20 to 27 mm in length)
Stage 4: Pigmented closed flower bud (27 to 35 mm in length)
Stage 5: Fully pigmented closed flower bud (35 to 45 mm in length)
Stage 6: Fully pigmented bud with emerging corolla (45 to 55 mm in length)
Stage 7: Fully opened flower (55 to 60 mm in length)

Other petunia cultivars (such as R27 and W115) were grouped into similar developmental stages as described above, however, the overall lengths of the buds varied between cultivars.

Rose

Flowers of *Rosa hybrida* cv. Rote rose were obtained from a nursery in Kyoto, Japan.

Stages of *Rosa hybrida* flower development are defined as follows:
Stage 1: Unpigmented, tightly closed bud.
Stage 2: Pigmented, tightly closed bud.
Stage 3: Pigmented, closed bud; sepals just beginning to open
Stage 4: Flower bud beginning to open; petals heavily pigmented; sepals have separated.
Stage 5: Sepals completely unfolded; some curling. Petals are heavily pigmented and unfolding.

Petunia Plant Material

The *Petunia hybrida* lines used in the cDNA-AFLP screening were R27 (wild-type (wt)), W225 (an1, frame-shift mutation in R27 background), R144 (ph3-V2068 transposon insertion in PH3 in R27 background), R147 (ph4-X2058 transposon insertion in PH4 in R27 background) and R153 (ph5 transposon insertion in PH5 crossed into a R27 background). All lines have genetically identical background and to diminish differences in environmental conditions which could lead to differences in transcript levels, the plants were grown in a greenhouse adjacent to each other.

The *Petunia hybrida* line M1×V30 used in transformations experiments was an F1 hybrid of M1 (AN1, AN2, AN4, PH4, PPM1, PPM2) crossed with line V30 (AN1, AN2, AN4, PH4, PPM1, PPM2). Flowers of M1×V30 are red-violet and generally accumulate anthocyanins based upon malvidin and low levels of the flavonol quercetin.

*Petunia hybrida* Transformations

As described in Holton et al, *Nature* 366:276-279, 1993 or Brugliera et al, *Plant J.* 5:81-92, 1994 or de Vetten N et al, *Genes and Development* 11:1422-1434, 1997 or by any other method well known in the art.

Preparation of Petunia R27 Petal cDNA Library

A petunia petal cDNA library was prepared from R27 petals using standard methods as described in Holton et al, 1993 supra or Brugliera et al, 1994 supra or de Vetten N et al, 1997 supra.

Transient Assays

Transient expression assays were performed by particle bombardment of petunia petals as described previously (de Vetten et al, 1997 supra; Quattrocchio et al, *Plant J.* 13:475-488, 1998.

pH Assay

The pH of petal extracts was measured by grinding the petal limbs of two corollas in 6 mL distilled water. The pH was measured directly (within 1 min) with a normal pH electrode, to avoid that atmospheric $CO_2$ would alter pH of the extract HPLC and TLC Analysis HPLC analysis was as described in de Vetten et al, *Plant Cell* 11(8):1433-1444, 1999. TLC analysis was as described in van Houwelingen et al, *Plant J* 13(1):39-50, 1998.

Analysis of Nucleotide and Predicted Amino Acid Sequences

Unless otherwise stated nucleotide and predicted amino acid sequences were analyzed with the program Geneworks (Intelligenetics, Mountain View, Calif.) or MacVector™ application (version 6.5.3) (Oxford Molecular Ltd., Oxford, England). Multiple sequence alignments were produced with a web-based version of the program ClustalW (http://dot.imgen.bcm.tmc.edu:9331/multi-align/multi-align.html) using defaults settings (Matrix=blossom; GAPOPEN=0, GAPEXT=0, GAPDIST=8, MAXDIV=40). Phylogenetic trees were built with PHYLIP (bootstrap count=1000) via the same website, and visualized with Treeviewer version 1.6.6 (http://taxonomy.zoology.gla.ac.uk/rod/rod.html)

Homology searches against Genbank, SWISS-PROT and EMBL databases were performed using the FASTA and TFASTA programs (Pearson and Lipman, *Proc. Natl. Acad. Sci. USA* 85(8): 2444-2448, 1988) or BLAST programs (Altschul et al., *J. Mol. Biol.* 215(3): 403-410, 1990). Percentage sequence identities and similarities were obtained using LALIGN program (Huang and Miller, *Adv. Appl. Math.* 12: 373-381, 1991) or ClustalW program (Thompson et al., *Nucleic Acids Research* 22: 4673-4680, 1994) within the MacVector™ application (Oxford Molecular Ltd., England) using default settings.

RNA Isolation and RT-PCR

RNA isolation and RT-PCR analysis were carried out as described by de Vetten et al, 1997 supra. Rapid amplification of cDNA (3') ends (RACE) was done as described by Frohman et al, *PNAS* 85:8998-9002, 1988.

EXAMPLE 1

Transcript Profile Analysis

A combination of cDNA-AFLP and microarray analysis were utilized in order to identify transcripts that were down-regulated in an1⁻, ph3⁻ and ph4⁻ mutants. A summary of results is shown in Table 3

EXAMPLE 2

Description of cDNA-AFLP

Using 256 primer combinations of MseI+NN/EcoRI+NN, around 20,000 fragments were analyzed which covered around 25% of total transcripts. 80 fragments were isolated from the gel and 20 were further characterized by RT-PCR of total RNA isolated from petunia mutant lines including wild-type and an1, ph2, ph3, ph4, ph5 mutants. Sixteen of these fragments (see Table 3) were confirmed as being down-regulated in an1, ph3 and ph4 petunia lines compared to their expression levels in wild-type, ph2 and ph5 petunia lines.

RNA Isolation and cDNA Synthesis

The petunia lines R27 (wt), W225 (an1⁻), R144 (ph3⁻), R147 (ph4⁻) and R153 (ph5⁻) were used in the cDNA-AFLP screening. Around 25 to 30 flower buds (flower developmental stage 5, 6) were harvested from each petunia line and stored at -70° C. Total RNA was extracted from 10 corollas according to Logemann et al, *Anal Biochem.* 163(1):16-20, 1987. PolyA⁺ RNA was then isolated from 500 micrograms of total RNA using oligo(dT) coupled to magnetic beads according to the PolyATract (Registered) System (PROMEGA) protocol. One microgram of polyA⁺ RNA was then used for synthesizing double stranded (ds) cDNA using the GIBCO-BRL Superscript II system. After synthesis of ds cDNAs, the cDNAs were phenol extracted (Sambrook et al, 2001 supra) and the cDNA precipitated with the addition of salt and ethanol. The DNA pellet was then resuspended in 30 µL of distilled water.

Template Preparation

Restriction endonucleases MseI (digests a 4 base recognition sequence) and EcoRI (digests a 6 base recognition

TABLE 3

Transcripts identified by cDNA-AFLP or microarray analysis that are down regulated in an1⁻, ph3⁻ and ph4⁻ mutants and found at wild-type levels in ph2⁻ and ph5⁻ mutants

| Name | Size (bp) | Normal | Down regulated | NCBI Blast search |
|---|---|---|---|---|
| CAC 4.4 | 116 | wt, ph2, ph5 | an1, ph3, ph4 | No significant similarity |
| CAC 5.6 | 250 | wt, ph2, ph5 | an1, ph3, ph4 | putative outer membrane protein |
| CAC 7.0 | 300 | wt, ph2, ph5 | an1, ph3, ph4 | No significant similarity |
| CAC 7.4 | 150 | wt, ph2, ph5 | an1, ph3, ph4 | No significant similarity |
| CAC 7.5 | 170 | wt, ph2, ph5 | an1, ph3, ph4 | putative PM-type protein |
| CAC 8.3 | 150 | wt, ph2, ph5 | an1, ph3, ph4 | No significant similarity |
| CAC 8.9 | 252 | wt, ph2, ph5 | an1, ph3, ph4 | PREG1 like neg. regulator |
| CAC 10.6 | 181 | wt, ph2, ph5 | an1, ph3, ph4 | putative phosphatidylinositol kinase |
| CAC 12.1 | 71 | TBD | TBD | TBD |
| CAC 12.3 | 803 | wt, ph2, ph5 | an1, ph3, ph4 | 3'-5' exonuclease containing protein |
| CAC 13.4 | 126 | wt, ph2, ph5 | an1, ph3, ph4 | unknown protein |
| CAC 13.10 | 452 | wt, ph2, ph5 | an1, ph3, ph4 | membrane transporter like protein |
| CAC 14.2 | 1276 | wt, ph2, ph5 | an1, ph3, ph4 | no long ORF |
| CAC 14.3 | 1312 | wt, ph2, ph5 | an1, ph3, ph4 | putative SPFH domain containing protein |
| CAC 14.4 | TBD | TBD | TBD | TBD |
| CAC 16.1 | 188 | wt, ph2, ph5 | an1, ph3, ph4 | No significant similarity |
| CAC 16.2 | 1440 | wt, ph2, ph5 | an1, ph3, ph4 | no long ORF |
| CAC 16.5 | 1025 | wt, ph2, ph5 | an1, ph3, ph4 | cysteine proteinase |
| MAC F55 | full length | wt, ph2, ph5 | an1, ph3, ph4 | Plasma membrane ATPase |
| MAC 1D2 | 1164 | wt, ph2, ph5 | an1, ph3, ph4 | putative myosin protein |
| MAC 9F1 | 956 | wt, ph2, ph5 | an1, ph3, ph4 | unknown protein |
| MAC 10F12 | TBD | TBD | TBD | TBD |

ORF = open reading frame
TBD = to be done
CAC = transcript identified using cDNA-AFLP
MAC = transcript identified using microarray
NCBI- Blast search = Any similarities to known sequences were discovered by using a BLAST search (Altschul et al, Nucl. Acids Res. 25: 3389-3402, 1997) on the National Center for Biotechnology Information (NCBI) website (as of February 2005).

sequence) were used for the template preparation for cDNA-AFLP analysis. The cDNAs were digested with both restriction endonucleases in combination with ligation of adapters (Mse A1 (SEQ ID NO:7) and Mse A2 (SEQ ID NO:8)) annealed to each other and EcoA1 (SEQ ID NO:14) and EcoA2 (SEQ ID NO:15) also annealed to each other to form respectively a PCR adaptor for the MseI site and one for the EcoRI site) to the MseI and EcoRI ends. Each "restriction-ligation" reaction was performed in a total volume of 50 L which included 24 μL ds cDNA, 10 μL 5×RL buffer (50 mM Tris HAc pH7.5, 50 mM MgAc, 250 mM KAc, 25 mM DTT, 250 μg/μL BSA), 0.1 μL 100 mM ATP, 5 units MseI (New England Biolabs), 5 units EcoRI (New England Biolabs), 50 μmol MseI adapter (Mse A1 and Mse A2) (SEQ ID NO:7 and 8) and 50 pmol EcoRI adapter (EcoA1 and EcoA2) (SEQ ID NO:14 and 15). The adapters had previously been boiled for 2 minutes and then slowly allowed to cool to room temperature prior to their addition to the reaction. The "restriction-ligation" reaction was incubated for 4 hours at 37° C.

Amplification

Prior to amplification, cDNA templates were diluted 10-fold in water and then a volume of 10 μL was used in the first, non-radioactive, PCR amplification step with one nucleotide selective extension (EcoRI+N, MseI+N) primers (SEQ ID NO:10 to 13 and 16 to 19))(see Table 4) in a touch-down PCR program. The PCR cycle included a 94° C. denaturation step followed by annealing step of 30 seconds at temperatures starting at 65° C. and reducing in 0.7° C. increments down to 56° C. over 17 cycles followed by 18 cycles of 56° C. for 30 sec and finally an elongation step at 72° C. for 1 min. Eight microliters of the products from this first PCR were electrophoresced through a 1% w/v agarose gel and the expected DNA smear between 200 and 750 bp was detected. Subsequently, 0.5 μL of these products were used as template in a second "hot" PCR using 2 nucleotide extension (EcoRI+NN, MseI+NN) primers (SEQ ID NO. 20 to 51) (see Table 5) in standard PCR conditions with a touch-down PCR program as described previously. The EcoRI primers in the second PCR were radio-labeled with $^{33}$P in a reaction which included 50 ng primer, 5 μL 10×T4 kinase buffer, 10 μL $^{33}$P-CTP, 24 μL water and 9 units T4 polynucleotide kinase. The reaction was incubated for 1 hour at 37° C., followed by inactivation of the T4 kinase by treatment at 65° C. for 10 minutes.

TABLE: 4

Primers used in the cDNA-AFLP analysis

| SEQ ID NO. | Primer No. | Primer name | Primer sequence (5' to 3') |
|---|---|---|---|
| 7 | 701 | Mse A1 | GAC GAT GAG TCC TGA G |
| 8 | 702 | Mse A2 | TAC TCA GGA CTC AT |
| 9 | 703 | mse + 0 | GAC GAT GAG TCC TGA GTA A |
| 10 | 704 | Mse + A | GAC GAT GAG TCC TGA GTA AA |
| 11 | 705 | Mse + C | GAC GAT GAG TCC TGA GTA AC |
| 12 | 706 | Mse + G | GAC GAT GAG TCC TGA GTA AG |
| 13 | 707 | Mse + T | GAC GAT GAG TCC TGA GTA AT |
| 14 | 724 | EcoA1 | GTG ATA TCT CCA CTG ACG T |
| 15 | 725 | EcoA2 | CTC GTA GAG TGC GTA CC |
| 16 | 726 | Eco + A | AAT TGG TAC GCA GTC |

TABLE: 4-continued

Primers used in the cDNA-AFLP analysis

| SEQ ID NO. | Primer No. | Primer name | Primer sequence (5' to 3') |
|---|---|---|---|
| 17 | 727 | Eco + C | AGA CTG CGT ACC AAT TCA |
| 18 | 728 | Eco + G | AGA CTG CGT ACC AAT TCC |
| 19 | 729 | Eco + T | AGA CTG CGT ACC AAT TCG |

TABLE: 5

Primers with 2 nucleotide extensions used in the cDNA-AFLP analysis

| SEQ ID NO. | Primer No. | Primer name | Primer sequence (5' to 3') |
|---|---|---|---|
| 20 | 708 | Mse + AA | GAT GAG TCC TGA GTA AAA |
| 21 | 709 | Mse + AC | GAT GAG TCC TGA GTA AAC |
| 22 | 710 | Mse + AG | GAT GAG TCC TGA GTA AAG |
| 23 | 711 | Mse + AT | GAT GAG TCC TGA GTA AAT |
| 24 | 712 | Mse + CA | GAT GAG TCC TGA GTA ACA |
| 25 | 713 | Mse + CC | GAT GAG TCC TGA GTA ACC |
| 26 | 714 | Mse + CG | GAT GAG TCC TGA GTA ACG |
| 27 | 715 | Mse + CT | GAT GAG TCC TGA GTA ACT |
| 28 | 716 | Mse + GA | GAT GAG TCC TGA GTA AGA |
| 29 | 717 | Mse + GC | GAT GAG TCC TGA GTA AGC |
| 30 | 718 | Mse + GG | GAT GAG TCC TGA GTA AGG |
| 31 | 719 | Mse + GT | GAT GAG TCC TGA GTA AGT |
| 32 | 720 | Mse + TA | GAT GAG TCC TGA GTA ATA |
| 33 | 721 | Mse + TC | GAT GAG TCC TGA GTA ATC |
| 34 | 722 | Mse + TG | GAT GAG TCC TGA GTA ATG |
| 35 | 723 | Mse + TT | GAT GAG TCC TGA GTA ATT |
| 36 | 730 | Eco + AA | GAC TGC GTA CCA ATT CAA |
| 37 | 731 | Eco + AC | GAC TGC GTA CCA ATT CAC |
| 38 | 732 | Eco + AG | GAC TGC GTA CCA ATT CAG |
| 39 | 733 | Eco + AT | GAC TGC GTA CCA ATT CAT |
| 40 | 734 | Eco + CA | GAC TGC GTA CCA ATT CCA |
| 41 | 735 | Eco + CC | GAC TGC GTA CCA ATT CCC |
| 42 | 736 | Eco + CG | GAC TGC GTA CCA ATT CCG |
| 43 | 737 | Eco + CT | GAC TGC GTA CCA ATT CCT |
| 44 | 738 | Eco + GA | GAC TGC GTA CCA ATT CGA |
| 45 | 739 | Eco + GC | GAC TGC GTA CCA ATT CGC |
| 46 | 740 | Eco + GG | GAC TGC GTA CCA ATT CGG |
| 47 | 741 | Eco + GT | GAC TGC GTA CCA ATT CGT |

TABLE: 5-continued

Primers with 2 nucleotide extensions used in the cDNA-AFLP analysis

| SEQ ID NO. | Primer No. | Primer name | Primer sequence (5' to 3') |
|---|---|---|---|
| 48 | 742 | Eco + TA | GAC TGC GTA CCA ATT CTA |
| 49 | 743 | Eco + TC | GAC TGC GTA CCA ATT CTC |

In summary using 256 primer combinations of MseI+NN/EcoRI+NN, around 20,000 fragments were analyzed which covered around 25% of total transcripts. 80 fragments were isolated from the gel and 20 were further characterized by RT-PCR of total RNA isolated from petunia mutant lines including wild-type and an1, ph2, ph3, ph4, ph5 mutants. Sixteen of these CAC fragments (see Table 3) were confirmed as being down-regulated in an1, ph3 and ph4 petunia lines compared to their expression levels in wild-type, ph2 and ph5 petunia lines. A summary of the CAC fragments and their respective sizes along with detected sequence similarities to known sequences is shown in Table 6.

TABLE 6

A summary of fragments isolated by cDNA-AFLP that are down-regulated in an1, ph3 and ph4 *petunia* lines compared to their expression levels in wild-type, ph2 and ph5 *petunia* lines.

| Fragment | Further info | BLASTx result | Similarity E-value | Fragment size |
|---|---|---|---|---|
| CAC 4.4 | | NSS | — | 114 bp |
| CAC 5.6 | | Putative membrane prot. | 1 | 250 bp |
| CAC 6.6 | | NSS | — | 191 bp |
| CAC 7.0 | | ESTc74501(rice)/lipid transfer protein (A. th) | 0.021/0.17 | 279 |
| CAC 7.4 | | Putative senescence ass. prot. | $1 \times E^{-19}$ | 350 |
| CAC 7.5 | | Putative plasma membrane prot. | 0.2 | 543 bp |
| CAC 8.3 | | No sequence | — | — |
| CAC 8.8 | | Glycolate oxidase | 0.015 | 95 bp |
| CAC 8.9 | | PREG1-like negative regulator | $1 \times E^{-29}$ | 245 bp |
| CAC10.6 | | Put. phosphatidyl kinase | $1 \times E^{-11}$ | 181 bp |
| CAC 12.1 | | NSS | — | 71 bp |
| CAC 12.3 | | 3contains 3'-5'exonucl. domain | $2 \times E^{-5}$ | 845 bp |
| CAC 13.4 | | Unknown prot. (A. th.) | $2 \times E^{-10}$ | 124 bp |
| CAC 13.10 | | Membrane transporter | $1 \times E^{-10}$ | 346 bp |
| CAC 14.2 | | Same than 16.2 | — | 1261 bp |
| CAC 14.3 | | Putative SPFH protein | $1 \times E^{-137}$ | 1312 bp |
| CAC 14.4 | | No sequence data | — | — |
| CAC 16.1 | | Histone H2B-like prot. (TAIR) | 0.0077 | 87 bp |
| CAC 16.2 | | No long ORF | — | 1405 bp |
| CAC 16.4 | | No sequence data | — | — |
| CAC 16.5 | | Cystein proteinase | $2 \times E^{-50}$ | 1169 bp |
| CAC 13.2 | Only down in an1 mutants | Anthocyanins 3-O-glucosyltransferase | $6 \times E^{-10}$ | 215 bp |
| CAC 8.11 | Up in ph3, ph4 and an1 mutants | Hypothetical Protein AF420410 | $1 \times E^{-18}$ | 255 bp |
| CAC 4.5 | Only down in an1 mutants | Anthocyanins 5-O-glucosyltransferase | $1 \times E^{-21}$ | 251 bp |

Similarity E-value = a parameter generated by a BLASTX search that indicates the relative identity to an aligned sequence. The closer to 0 the E-value is the more significant the match
NSS = no sequence similarity TABLE: 5-continued Primers with 2 nucleotide extensions used in the cDNA-AFLP analysis

| SEQ ID NO. | Primer No. | Primer name | Primer sequence (5' to 3') |
|---|---|---|---|
| 50 | 744 | Eco + TG | GAC TGC GTA CCA ATT CTG |
| 51 | 745 | Eco + TT | GAC TGC GTA CCA ATT CTT |

Analysis of PCR Products:

The reaction products were analyzed by electrophoresing through a 5% denaturing polyacrylamide gel. After electrophoresis the gels were dried on a slab gel dryer and then exposed overnight. The radiolabeled signals of the reaction products were then detected using a Phosphor imager (Molecular Dynamics, Sunnyvale, Calif., USA).

EXAMPLE 3

Micro Array Analysis

For the micro-array hybridization, petal tissue of developmental stage 5 of both wildtype (R27) and an1⁻ mutant line (W225) was used to isolate polyA⁺ RNA according to protocol of the supplier (polyATtract mRNA Isolation System III, Promega). Microarrays were prepared and hybridized using conditions described by Verdonk et al, *Phytochemistry* 62: 997-1008, 2003.

Description of Microarray

Of 1415 ESTs spotted onto microarrays, 9 ESTs were found to be down-regulated by more than 10-fold in the an1 mutant petunia line (W225). Five of these sequences represented genes previously isolated and characterized (see Table 7). Four ESTs were further characterized by RT-PCR of total RNA isolated from petunia mutant lines including wild-type and an1, ph2, ph3, ph4, ph5 mutants. Two of these ESTs (MAC F55 and MAC 9F1) were confirmed as being down-regulated in an1 petunia lines.

TABLE 7

Clones identified in the microarray screen that showed 50 to 100 times downregulation in an1 mutants.

| Fragment | Further info | BLASTx result | Similarity E-value | Fragment size |
| --- | --- | --- | --- | --- |
| MAC F55 | | Plasma ATP-ase | $1 \times E^{-39}$ | 2850 bp |
| MAC ID 12 | | Putative myosin heavy chain | $2 \times E^{-48}$ | 1511 bp |
| MAC 9F1 | | *A. thaliana* At2g17710 expressed prot. | $1 \times E^{-16}$ | 687 bp |
| MAC C90 | | No sequence data | | |
| MAC 10F12 | | TBD | TBD | TBD |
| MAC M33 | Already known AN1 target | Cyt. b5 like | 0 | Full size cDNA |
| MAC DFRA | Already known AN1 target | *Petunia* DFR-A | 0 | Full size cDNA |
| MAC Rt | Already known AN1 target | *Petunia* RT | 0 | Full size cDNA |
| MAC AN9 | Already known AN1 target | *Petunia* GST | 0 | Full size cDNA |

Several more clones show a lower level of down regulation and could be considered in a second round of analysis.

The expression pattern and genetic control was determined for several of these genes by RT PCR in different petunia tissues and in flowers of wild type and mutant plants. The majority of these genes show higher expression in petals than in other parts of the plant and the expression studies in the mutants confirmed the pattern previously seen by transcript profiling.

The nucleotide and deduced amino acid sequences of MACF55 (Petunia) are shown in SEQ ID NOs:1 and 2; MAC9F1 nucleotide and deduced amino acid sequences are shown in SEQ ID NOs:3 and 4; CAC16.5 nucleotide and deduced amino acid sequences are shown in SEQ ID NOs:5 and 6.

EXAMPLE 4

Construction of RNAi Constructs for Expression in Petunia

In order to assess the role of these genes in the acidification of the vacuolar lumen in flower epidermal cells inverted repeat constructs of each gene were or are expressed in wild-type petunia plants with the aim of silencing the endogenous gene.

To date down regulation of three genes has resulted in a change in flower color with a concomitant change in vacuolar pH. These include MAC F55 (PPM1) (SEQ ID NO:1), MAC 9F1 (SEQ ID NO:3) and CAC 16.5 (SEQ ID NO:5).

Down Regulation of AL4C F55 (PPM1)

The MAC F55 clone codes for a plasma membrane ATPase (PPM), Petunia Plasma Membrane ATPase 1) (SEQ ID NO:1) and has a relatively high sequence identity with ATPase genes already isolated. However, alignment of the different members of the ATPase gene family, show that PPM1 groups together with AHA10 from *Arabidopsis* and PMA9 from Tobacco in the class III plasma ATPases (Arango et al, *Planta*, 216:335-365, 2003). These proteins all diverge from the other plasma ATPases in the C terminal part, which represents the site of interaction with 14.3.3 factors regulating the activity of the pump. Cellular localization and function have never been defined for any member of this group, leaving open the possibility that PPM1 resides in other cellular membranes than the plasma membrane. Baxter et al, *PNAS*, 102:2649-2654, 2005 describe analysis of *Arabidopsis* AHA10 mutants. AHA10 was described as having a specific effect on proanthocyanidin and vacuole biogenesis. The aha10 mutants characterized had decreased levels of proanthocyanidins in their seed coats and the seed coat endothelial cells displayed many small vacuoles rather than one central vacuole as observed in wild-type seeds.

In order to assess the role of PPM1 gene in the acidification of the vacuolar lumen in flower epidermal cells, wild type petunia plants (V30×M1) were transformed with two inverted repeat constructs: a 233 bp inverted repeat spanning from nucleotide 2937 to nucleotide 3170 of the PPM1 full size cDNA (SEQ ID NO:1) and a 499 bp inverted repeat spanning from nucleotide 2671 to nucleotide 3170 of the PPM1 full size cDNA (SEQ ID NO:1), both under the control of the CaMV 35S promoter.

Inverted Repeat Constructs (Gateway)

A *P. hybrida* R27 petal cDNA library was hybridized with $^{32}$P-labeled fragments of PPM1. The PPM1 fragment was generated using PCR amplification with first stand cDNA from RNA isolated from petunia petals as template and the primers #1702 (SEQ ID NO:52) and #1703 (SEQ ID NO:53). The full length PPM1 sequence was obtained using a double 5' Rapid Amplification of cDNA (5'/3'-RACE KIT 2ND generation, Roche, USA) according to the manufacturer's protocols. Primers #1703 (SEQ ID NO:53), #1742 (SEQ ID NO:55) and #1832 (SEQ ID NO:61) were used for the first 5'-RACE whilst primers #1789 (SEQ ID NO:58), #1812 (SEQ ID NO:59) and #1831 (SEQ ID NO:60) were used for the second 5'-RACE.

PCR conditions in all amplifications was as follows: 96° C., 30 seconds, 65° C., 30 seconds and 72° C. for 3 minutes, 32 cycles (T3 thermocycler, Biometra).

TABLE 8

Primers used in amplification of PPM1 fragments.

| SEQ ID NO: | Primer No. | Direction | Sequence 5' to 3' |
|---|---|---|---|
| 52 | 1702 | Forward | GGACCTTAACAAAATTCAAACAG |
| 53 | 1703 | reverse | AAATTAATGAATGATATGAGG |
| 54 | 1741 | Forward | TGAAGAAATGTCATCAGCCG |
| 55 | 1742 | reverse | GTTCAGCAATCATAGATGGC |
| 56 | 1750 | Forward | GCTCTGACTGGAGAAGCCTGG |
| 57 | 1788 | Forward | CCAAGAGAAGCAACAGATAGCTGCAA |
| 58 | 1789 | reverse | TTGCAGCTATCTGTTGCTTCTCTTGG |
| 59 | 1812 | reverse | GAATCAATGTAAGTGATTGCAGTCCG |
| 60 | 1831 | reverse | AACTGATAGGACTGTTGGCATAGC |
| 61 | 1832 | reverse | GCTGGTGCATCATTTACTCCATC |
| 62 | 1847 | Forward | ATGGCCGAAGATCTGGAGAGACC |
| 63 | 1848 | reverse | CTGCAGGGATGATATCACCAAGC |
| 64 | 1861 | Forward | CTGATAATAGCAATCCTAAATGATGG |
| 65 | 1864 | Forward | CGGAATTCATGGCCGAAGATCTGGAGAGACCTTTAC |
| 66 | 1885 | reverse | CCCGGGCTTCTCCAGTCAGAGCATATCAAACAGCAA |
| 67 | 1886 | Forward | AAGAATTCGTTTGTTATGCTCTGACTGGAGA |
| 68 | 1956 | reverse | GACTGCGGGTAACAAATATTAGCG |
| 69 | 2035 | Forward | GCAAATATCAGGGAAGTGCATTTCC |
| 70 | 2037 | Forward | CGGAATTCTCGCAAATATCAGGGAAGTGCATTTCCTT |
| 71 | 2038 | reverse | TTATGAATCAATGTAAGTGATTGCAGTCCG |
| 72 | 2039 | Forward | TAGCCCATGGCCGAAGATCTGGAGAGACC |
| 73 | 2040 | reverse | CATGAGCCATGGACAAACTGTATGAGCTGTTTG |
| 74 | 2073 | Forward | GCTTGCTGATCCAAAGGAGGCACGT |
| 75 | 2075 | reverse | GTAAGGATTCCCCAGTAAGAGC |
| 76 | 2078 | reverse | CGGGATCCTGGAGCCAGAAGTTTGTTATAGGAGG |
| 77 | 2123 | reverse | GGTCTTGGAGATGGTTTAACCC |
| 78 | 2124 | Forward | GCTGCTAGGAGTGCTGCTGATCTTG |
| 79 | 2196 | reverse | GCATGATACAATGTCCTAGATTCACTTC |
| 80 | 2270 | Forward | CTAACCATGGCCGAAGACCTGGAGAGACCT |
| 81 | 2271 | reverse | GTTTGATCAGACGTCACATGTCTCCAAACTGTATGAGCTGTTTGA |

Figure 2:
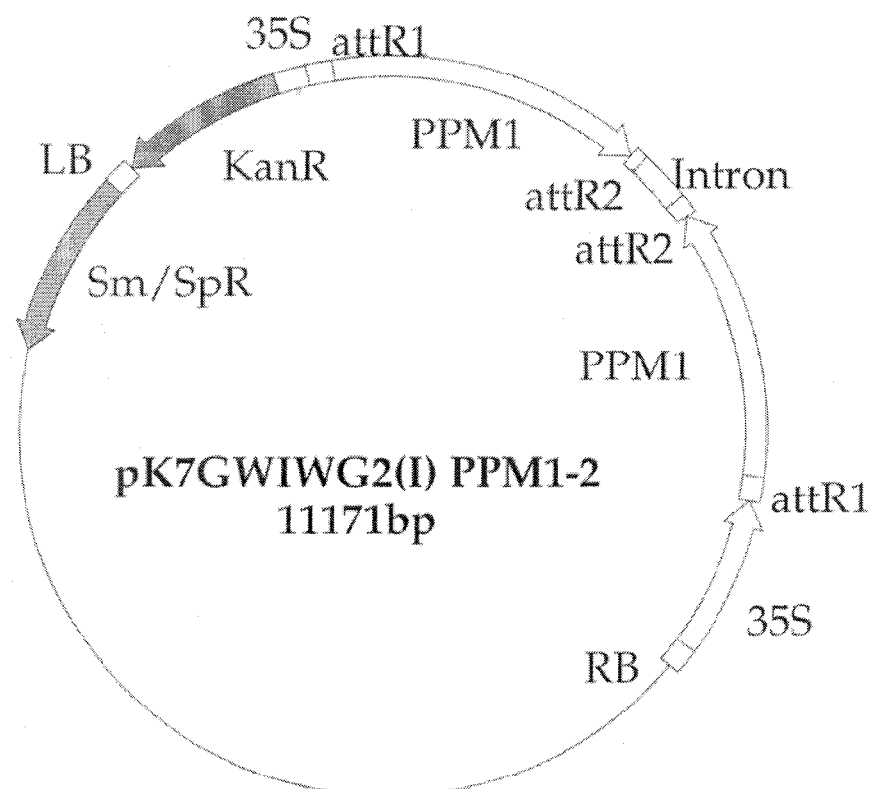
FIG. 2 is a diagrammatical representation of replicon pK7GWIWG2(I) PPM1-2 11171bp.

Two PPM1 cDNA fragments (A and B) were amplified using the following primers: A, #1703 (SEQ ID NO:53) and #1702 (SEQ ID NO:52) and B, #1703 (SEQ ID NO:53) and #1750 (SEQ ID NO:56). The PCR products were then ligated into the vector pGemt-easy (Promega). Clones containing the correct insert were selected by PCR, digested with EcoRI and subsequently cloned into the EcoRI restriction site of the entry vector pDONR207(1) of the Gateway system (INVITROGEN). Using the Gateway LR recombination reaction (INVITROGEN), the inserts were translocated into pK7GWIWG2(I) and transformed into competent *E. coli* DH5a cells. With the primer combinations 35S promoter (#27) together with the pK7GWIWG2(I) intron reverse primer (#1777), and 35S terminator (#629) together with the intron forward primer (#1778) clones containing the insert in an inverted repeat arrangement were selected. Subsequently, these clones, pK7GWIWG2 (I) PPM1-1 (FIG. 1) and pK7GWIWG2 (I) PPM1-2, (FIG. 2) were introduced into *Agrobacterium tumefaciens* by electroporation and transfected into petunia via leaf disk transformation. Transformed plants were selected on MS plates containing 250 microgram/mL of kanamycin, and after rooting, were grown in normal greenhouse conditions.

Of the 6 transgenic plants produced using p K7GWIWG2 (I) PPM1-1, 6 resulted in a change in flower color from red to purple/blue. Of the 3 transgenic plants produced using p K7GWIWG2 (I) PPM1-2, 3 resulted in a change in flower color from red to purple/blue. The changes in color correlated with silencing of the endogenous PPM1 transcript and a pH increase of the crude flower extract of about 0.5 units. No effect was detectable on the amount and type of anthocyanin pigment accumulated in the flowers of the silenced plants as determined by TLC and HPLC.

Petunia plants mutated in different petunia pH loci as well as those transgenic plants showing silencing of PPM1, still express another member of the plasma membrane ATPase family from Petunia namely, PPM2.

PPM2 shows high homology with class II of plasma ATPase proteins containing PMA4 from *Nicotiana* and AHA2 from *Arabidopsis* for which plasma membrane localization in plant cells has been shown, as well as the capability of complementing pmp1 mutants in yeast and their regulation by 14.3.3 proteins (Jahn et al, *JBC*, 277, 6353-6358, 2002).

TABLE 9

Primers used in amplification of PPM2 fragments.

| SEQ ID NO: | PPM2 | Direction | Sequence (5' to 3') |
|---|---|---|---|
| 102 | 1969 | forward | CTTGTTGACAGCACCAACAATG |
| 103 | 1970 | reverse | CAAGGATCTATCGACACTCAACTTG |

The PPM-1 gene is intriguing because the possible involvement of a P-type ATPase in vacuolar acidification has never been proposed before. From preliminary analysis of PPM1 expression in Petunia, it was found that the gene is specifically expressed in the flower limb (nowhere else in the plant). Because petunia flowers mutated in AN1, PH3 or PH4 do not show any expression of PPM-1, and still look healthy, it is tempting to think that the function of this specific gene is confined to the control of the vacuole environment, while it does not contribute to the regulation of the cytosolic pH. It is also possible that other members of the P-ATPase family are expressed in these same cells and control the proton gradient through the plasma membrane.

A question of considerable significance concerns the cellular localization of this protein. P-ATPases are membrane associated proteins but in this specific case it is not expected that the PPM-1 protein would be localized on the plasma membrane as this would not explain its contribution to vacuolar pH control. A GFP fusion of the full-size PPM-1 cDNA was expressed in petunia cells (transient expression in flowers via particle bombardment) and its localization was visualized by confocal microscopy. The different cellular compartment and vacuolar types are identified by marker GFP fusions (Di Sansebastiano et al, *Plant Physiology*, 126, 78-86, 2001). The PPM-1 protein appeared to be localized on the tonoplast or in vesicles that later fuse to the central vacuole of the flower epidermal cells, which opens a new view of the role of these proteins in cellular homeostasis.

The capability of a PPM-1 expression construct is also tested to complement the yeast Pmal mutant missing the endogenous P-ATPase activity to make sure that PPM-1 encoded proteins has indeed P-ATPase activity.

Further studies on the role of PPM-1 in the pathway leading to flower vacuole acidification will suggest studies on how the activity of this class of P-ATPases is regulated. As already mentioned, nothing is known about the function and regulation of class III P-ATPases in plants. Although the protein sequences are overall very homologous to those of other P-ATPases, these proteins have a different sequence in the C-terminal tail that has been demonstrated to enable interaction with 14-3-3 proteins required for reaching a high state of activation (Arango et al, 2003, supra). This raises the question whether P-ATPases of this class interact with 14-3-3 regulators or not. A yeast two hybrid screening of a petunia corolla cDNA library was performed to look for proteins interacting with this part of PPM-1 and the purified PPM-1 protein was analyzed for binding to 14-3-3 protein in vitro (overlay assay).

Phosphorylation of Thr947 has also been recognized as an important step in the regulation of the ATPase activity (Jahn et al, 2001, supra). The PH2 gene from petunia has been cloned and shown that this encodes a h/Ser protein kinase of which PPM-1 may directly or indirectly (e.g. via a cascade of protein kinases) be the target of this kinase. To test this possibility, a full-size PPM-1 cDNA fused to a Hys-tag was expressed in wild type and in ph2-petunia plants. The recombinant PPM-1 protein was purified from flower extracts using a nickel column, then visualized using SDS-PAGE and immunodetection with anti-ATPase and antiphosphothreonine antibodies. This, therefore, assists in reconstructing a new small part of this pH-controlling pathway.

Down Regulation of MAC 9F1, A Target Gene of AN1, PH3 and PH4 Essential for Vacuolar Acidification The nucleotide and derived amino acid sequence of the clone MAC 9F1 (SEQ ID NO:3 and 4, respectively) do not show clear homology with any identified nucleic acid sequence or protein of known function, respectively. However, when inverted repeats of 9F1 were expressed in petunia wild-type plants the silencing of the 9F1 endogenous gene resulted in blue flowers with increased flower extract pH.

Inverted Repeat Constructs (Gateway)

Figure 3:
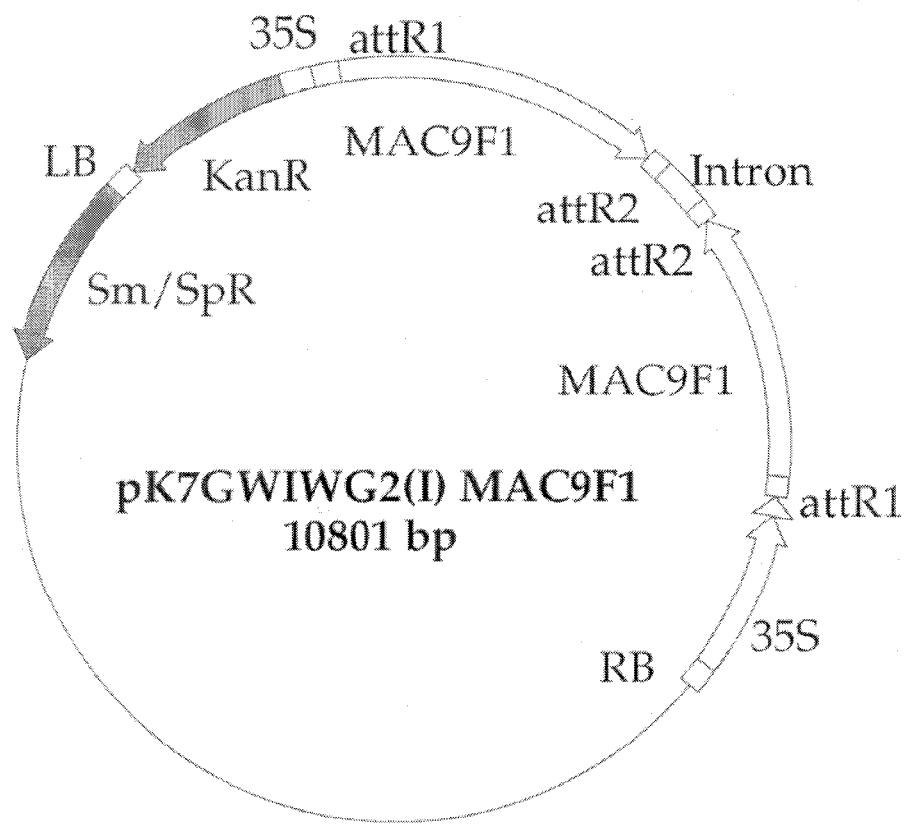
FIG. 3 is a diagrammatical representation of replicon pK7GWIWG2(I) MAC9F1 10801bp.

An inverted repeat construct, pK7GWIWG2(I) MAC9F1 (FIG. 3), of 9F1 was prepared using primers described in Table 10 and the Gateway system as described above.

The inverted repeat 9F1 construct was introduced into *Agrobacterium tumefaciens* by electroporation and transfected into petunia via leaf disk transformation. Transformed plants were selected on MS plates containing 250 microgram/mL of kanamycin, and after rooting, were grown under normal greenhouse conditions.

Of 2 transgenic plants produced, 1 resulted in a change in flower color from red to purple/blue. The change in flower color correlated with silencing of the endogenous 9F1 gene and a pH increase of the crude flower extract of 0.5 units. No effect was detectable on the amount and type of anthocyanin pigment accumulated in the flowers of the silenced plants as determined by TLC and HPLC.

TABLE 10

Primers used in amplification of MAC9F1 fragments.

| SEQ ID NO: | Primer No. | Direction | Sequence 5' to 3' |
|---|---|---|---|
| 82 | 1706 | reverse | GTTCGCAAGCGCAATACTTAC |
| 83 | 1707 | forward | GGAATTCGGCACGAGGTCAC |
| 84 | 1743 | forward | AAGAGTAGCTGATCATGG |
| 85 | 1768 | forward | GATGAGGACATGAAGGAGCAAAGAG |
| 86 | 1876 | reverse | CTTCAGTCTTGCGTTTCTGCTTCC |
| 87 | 1877 | reverse | CTCCTGTTTTGTCAGGCTTGGTGC |
| 88 | 1878 | reverse | CGGCGGCGGTGGACTTGTCTTC |
| 89 | 2061 | reverse | GCTCTAGACTAGAATATGCCAAAAGTGGTTGCAAC |
| 90 | 2101 | forward | ATCGAATTCATGGCTGCACCAAGCCTAACAAAACAG |
| 91 | 2178 | reverse | ACCGCTCGAGCTAGAATATGCCAAAAGTGGTTGCAAC |

To gain more insight into the function of the small protein encoded by the 9F1 gene, the cellular localization is defined by studying a GFP fusion in transient assay and look for possible interacting partners which are screened via yeast two hybrid screening of a cDNA library. An indication of the biochemical function of 9F1 also comes from the phenotype of plants overexpressing this gene.

The result of a BLAST search with this protein identifies a small family of proteins of which the two members with the highest homology to 9F1 come from *Arabidopsis* and rice. The characterization of an *Arabidopsis* knockout (KO) mutant for the 9F1 homolog might, therefore, be helpful.

Down Regulation of CAC16.5

The nucleotide and derived amino acid sequence of the clone CAC16.5 is shown in SEQ ID NO:5 and 6, respectively. The predicted amino acid sequence shows relatively high homology with Cysteine Proteases. The localization of these enzymes is typically vacuolar and their activity is dependent on relatively low environmental pH.

When a construct containing inverted repeats of CAC16.5 was introduced into petunia wild-type plants the silencing of the CAC16.5 endogenous gene surprisingly resulted in blue flowers with increased flower extract pH.

Inverted Repeat Constructs (Gateway)

Figure 4:
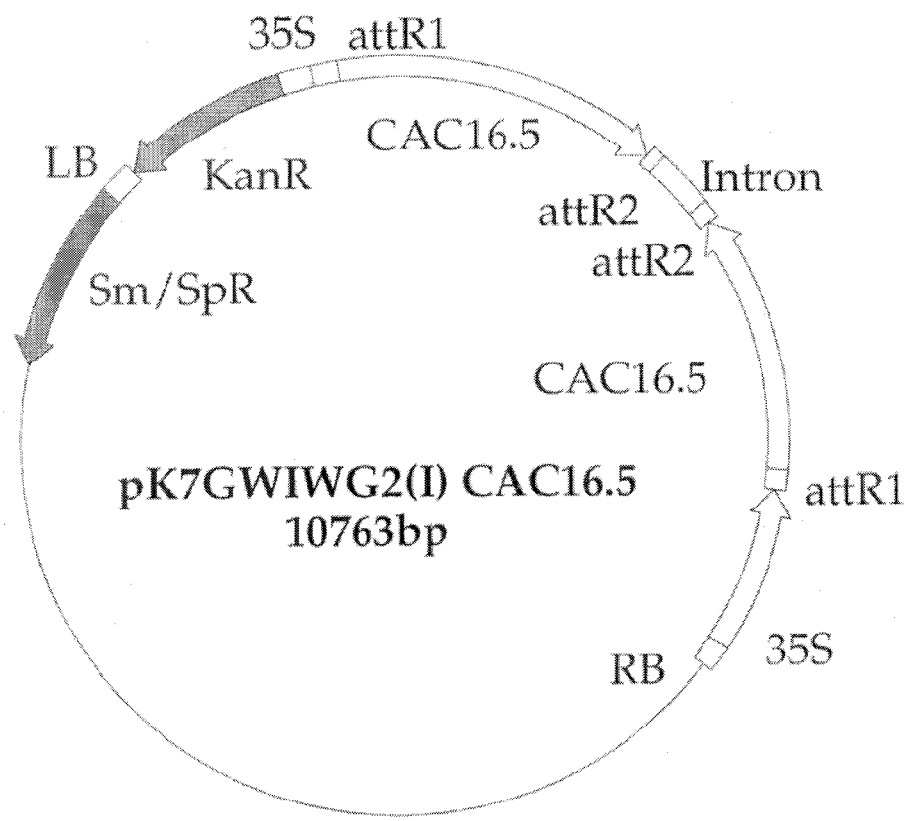
FIG. 4 is a diagrammatical representation of replicon pK7GWIWG2(I) CAC16.5 10763bp.

An inverted repeat construct, pK7GWIWG2(I) CAC16.5 (FIG. 4), of CAC16.5 was prepared using primers described in Table 11 and the Gateway system as described above.

The inverted repeat CAC16.5 construct was introduced into *Agrobacterium tumefaciens* by electroporation and transfected into petunia via leaf disk transformation. Transformed plants were selected on MS plates containing 250 microgram/mL of kanamycin, and after rooting, were grown in normal greenhouse conditions.

Of 4 transgenic plants produced, 3 resulted in a change in flower color from red to purple/blue. The change in flower color correlated with silencing of the endogenous CAC16.5 and a pH increase of the crude flower extract of 0.3 units. No effect was detectable on the amount and type of anthocyanin pigment accumulated in the flowers of the silenced plants as determined by TLC and HPLC.

TABLE 11

Primers used in amplification of CAC16.5 fragments.

| SEQ ID NO: | Primer No. | Direction | Sequence 5' to 3' |
|---|---|---|---|
| 92 | 1654 | reverse | CCTGTATATAGTTGGAAATCC |
| 93 | 1655 | forward | CAAGGCACTTGCAATATCACC |
| 94 | 1769 | reverse | GTAATGACATTCAAACAGCATCC |
| 95 | 1770 | forward | CTTCGTCGCCTCCTTATCCATCTCC |
| 96 | 1870 | reverse | GGATTATCAAGAATTCATGGGG |
| 97 | 1871 | reverse | GCCTCCTTATCCATCTCCAGCCC |

Because the function of cysteine proteases is the cleavage of a variety of other peptides, it is interesting to identify the target of the proteolitic action of CAC16.5. To do this a construct "bait" plasmid is constructed for yeast two hybrid screening in which the Cys25 residue in the active site of the CAC16.5 gene is mutated. This avoids the cleavage of the substrate when the two protein interact with each other and will allow to isolate the "prey" plasmid(s) containing the gene(s) that encodes for the target of CAC16.5. The characterization of the target of this proteolitic activity helps to further reconstruct the acidification pathway.

Detailed analysis of flowers from wild type, pH mutant and plants overexpressing regulators of the pH pathway has recently shown structural differences in the vacuoles of the epidermal cells. The most relevant difference involves the dimension and shape of the vacuoles in these cells and points towards a role of the PH genes in defining the height and width of vacuolar structure. Because the papillar shape of the cells in the corolla epidermis is peculiar to this tissue (to which this entire acidification pathway is restricted as shown by expression studies of the genes involved), it is speculated that the genes controlling acidity in the vacuolar lumen possibly also define the vacuole type (e.g. lytic or storage vacuole) and with it cell identity.

With this in mind, the pathway of events regulated by AN1, PH3 and PH4 is dissected to understand if specific steps are related with the gaining of identity of the vacuole (and therefore, of the cell) or the cell shape is simply a secondary effect of the internal pH of the vacuole compartment. The microscopic analysis of epidermal cells in flowers of plants silenced for different genes along the pH regulating pathway will provide an answer to this question and will possibly open a window on the mechanism of vacuolar diversification.

pH4 is a member of the MYB family of transcription factors that is expressed in the petal epidermis and that can physically interact with AN1 and JAF13. This indicates that AN1 is present in at least two distinct transcription complexes. One complex includes pH4 and activates a set of unknown target genes involved in vacuolar acidification, whereas another (pH4-independent) complex activates the structural anthocyanin genes.

EXAMPLE 5

Isolation of PPM cDNA Homologs from Rose

A Rose (cv. 'rote rose') petal cDNA library was constructed utilizing total RNA isolated from petals from developmental stages 1 to 3 rose buds and a λZAP cDNA synthesis kit (Stratagene) according to procedures described above and those recommended by the manufacturer. A library of $3 \times 10^5$ pfu was thus constructed for isolation of a rose PPM1 cDNA clone.

Around 300,000 pfu of the rose petal cDNA library were screened with a DIG-labelled petunia PPM1 probe using low stringency conditions as described the manufacturer except that the hybridisation buffer contained 30% v/v formamide and was done at 37° C. overnight (as described below). ADIG-labeled petunia PPM-1 R27 cDNA fragment of around 700 bp was prepared usingprimer sets described below (SEQ ID NO:100 and 101). The primers were designed based on the petunia PPM1 sequence (SEQ ID NO:1).

```
#2124:
5'-GCTAGGAGTGCTGCTGATCTTG        (SEQ ID NO: 100)

#2078:
5'-GGAGCCAGAAGTTTGTTATAGGAGG     (SEQ ID NO: 101)
```

The PCR conditions used for labelling of the petunia PPM1 probe were as follows.
94° C. 1 min×1 cycle
94° C. 30 sec, 55° C. 30 sec, 72° C. 1 min×25 cycles
72° C. 7 min×1 cycle Hybond-N(Amersham) membranes were used and treated according to the manufacture's instructions. Prior to hybridization, duplicate plaques lifts were washed in a prewash solution (50 mM Tris-HCl, pH7.5, 1 M NaCl, 1 mM EDTA, 0.1% w/v sarcosine) at 65° C. for 30 minutes. This was followed by washing in 0.4M sodium hydroxide at 65° C. for 30 minutes, then in a solution of 0.2M Tris-HCl, pH 8.0, 0.1×SSC, 0.1% w/v SDS at 65° C. for 30 minutes and finally rinsed in 2×SSC, 1.0% w/v SDS.

Hybridization conditions included a prehybridization step at 37° C. for 2-3 hr in Hybridization Buffer (5×SSC, 30% v/v Formamide, 2% w/v Blocking Reagent, 0.1% w/v N-lauroylsarcosine (Sodium salt), 1% w/v SDS, 50 mM Na-Phosphate Buffer (pH7.0)). Following removal of the prehybridization buffer, hybridization mix was added which contained Hybridization Buffer (5×SSC, 30% v/v Formamide, 2% w/v Blocking Reagent, 0.1% w/v N-lauroylsarcosine (Sodium salt), 1% w/v SDS, 50 mM Na-Phosphate Buffer (pH7.0)) with DIG labeled petunia PPM1 (SEQ ID NO:1) probe added. Hybridization was carried out overnight at 37° C. Subsequent to this the filters were washed in 5×SSC/1% w/v SDS twice at 55° C. for 1 hr each.

Figure 23:
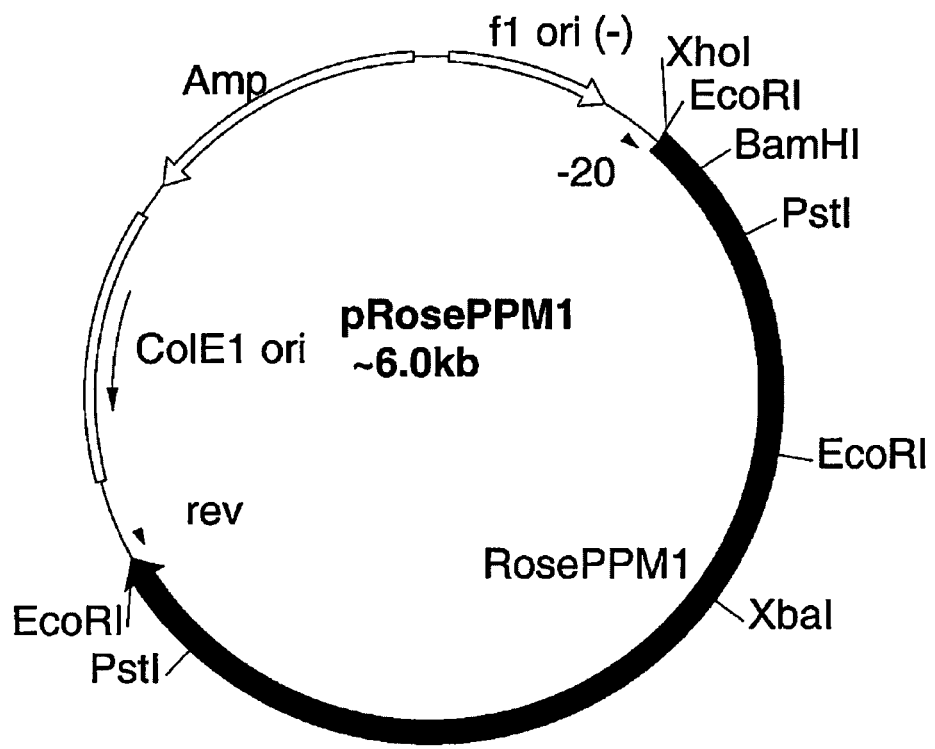
FIG. 23 is a diagrammatic representation of the plasmid pRosePPM1 containing the rosePPM1 cDNA clone (SEQ ID NO: 98) in a pBluescript SK– vector. Selected restriction endonuclease sites are marked.

Two rounds of screening yielded 36 positively hybridizing clones. These were in vivo excised according to the manufacture's instructions. In each case the excised cDNA was cloned in a phagemid vector pBluescript SK– and the inserts were subsequently sequenced. Of the original 36 clones, three were found to encode an identical cDNA, the longest of them, clone 1-2 (pRosePPM1 FIG. 23) was used for further analysis. This sequence (SEQ ID NO: 98) was identified as a rose PPM1 clone by reason of homology with the petunia PPM1 clone. The rose PPM1 nucleotide sequence (SEQ ID NO: 98) shared 72% identity with the petunia PPM1 nucleotide sequence (SEQ ID NO: 1) The deduced amino acid sequence of the rose PPM1 clone (SEQ ID NO: 99) shared 83% identity and 91% similarity with the deduced amino acid sequence of the petunia PPM1 clone (SEQ ID NO: 2). Added to this the deduced amino acid sequence of the rose PPM1 clone (SEQ ID NO: 99) when aligned with the petunia PPM1 sequence (SEQ ID NO:2) also contained the same 3 amino acid residues ("HTV") (FIG. 24) at the C-terminus which have been identified (International Patent Application PCT/AU2006/000451) as 'tell-tale' or typical of this class of P-ATPases. The nucleotide and amino acid sequences of rose PPM1 are shown in FIGS. 21 and 22, respectively.

EXAMPLE 6

Construction of Plant Transformation Vectors for Down Regulation of Rose PPM1

Figure 8:
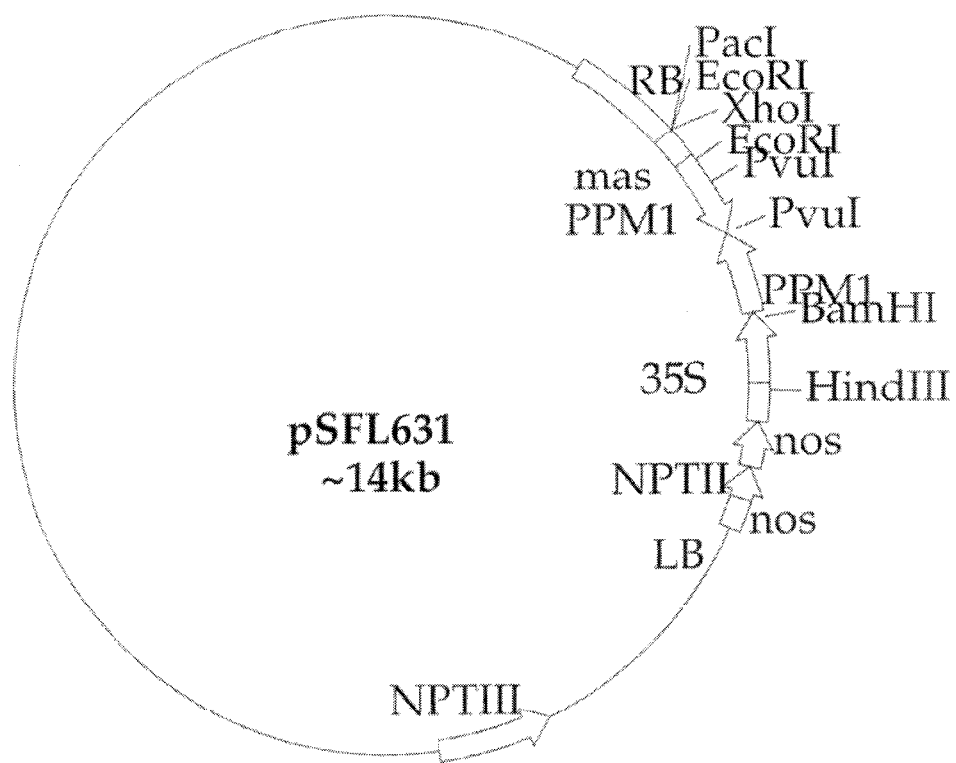
FIG. 8 is a diagrammatical representation of pSFL631 (~14 kb).

The rose PPM cDNA was used as a basis for construction of a plant transformation vector aimed at downregulation or gene knockout of rose PPM1 in rose petals. Knockout of rose PPM1 would thus lead to elevation of petal vacuolar pH and change of flower color. To achieve gene knockout a strategy aimed at production of dsRNA for rose PPM1 was used. Thus a hairpin structure was engineered using 600 bp of 5' sequence of the cDNA (SEQ ID NO: 98) and incorporated into a CaMV $^{35}$S:mas expression cassette in the binary vector pBinPLUS. This construct was named pSFL631 (FIG. 8). It was transferred into *Agrobacterium tumefaciens* preparatory to transformation of rose tissue according to the method described below. A further construct aimed at confining expression of the rose PPM1 knockout cassette to petal tissue is now in progress. One example of such a strategy will include the use of a rose CHS promoter (International Patent Application PCT/AU03/01111). Other genes of the anthocyanin biosynthetic pathway will be a useful source of promoters for limiting expression of a gene cassette to petals as desired. Manipulation of the sequences included in further constructs will be used to alter the specificity of (i) gene knockout or silencing, and (ii) gene expression, that is expression of the pH-modulating sequences which are typically configured, using technology such as RNAi, to downregulate or silence the target gene. Such pH-modulating sequences will include PPM1, MAC9F1 and CAC16.5 homologs from rose.

Construction of Plant Transformation Vectors for Down Regulation of Rose PPM1 Using 3' End of RosePPM1 sequence.

An alternative plant transformation vector is produced by generating a hairpin structure using the sequence at the 3' end of the rose PPM-1 sequence (SEQ ID NO: 98). This would be more specific to the rose PPM-1 sequence without downregulating other plasma ATPases that may be vital to plant or flower development. One example of such a strategy includes isolating the ~240 bp PstI/EcoRI fragment from pRosePPM1 (FIG. 23) encompassing the 3' end of the cDNA clone. This fragment is then ligated with an ~5.9 kb PstI/EcoRI fragment of pKIWI101 containing a hybrid promoter consisting of a promoter region from CaMV 35S gene with enhancer elements from a promoter fragment of mannopine synthase (mas) gene of *Agrobacterium tumefaciens* and ~1.6 kb terminator fragment from octopine synthase gene of *A. tumefaciens* (Janssen and Gardner, Plant Molecular Biology, 14: 61-72, 1989; International Patent Application PCT/AU03/01111). Correct insertion of the fragment is established by restriction endonuclease analysis of plasmid DNA isolated from ampicillin-resistant transformants. The resulting plasmid is then linearised with EcoRI and the overhanging ends are repaired. The ~240 bp PstI/EcoRI ends of the rosePPM1 fragment (described above) are also repaired and the resulting fragment is ligated with the blunt ends of the linearised plasmid. Correct insertion of the fragment in an antisense direction is established by restriction endonuclease analysis and sequencing of plasmid DNA isolated from ampicillin-resistant transformants. The ~2.4 kb fragment containing 35S: sense 3' rosePPM1/antisense 3' rosePPM1: ocs chimaeric gene contained is then released upon digestion with XhoI/XbaI and the overhanging ends are repaired. The resulting 2.4 kb fragment is isolated and ligated with SmaI ends of the binary vector pCGP1969 (International Patent Application PCT/AU03/01111) or other binary vector containing F3'5'H genes (International Patent Application PCT/AU03/01111, International Patent Application PCT/JP2004/011958). The T-DNAs contained in the binary vector plasmids are introduced into *Rosa* hybrida cultivars such as but not limited to Kardinal, Soft Promise, Sonia, Medeo, Lavande via *Agrobacterium*-mediated transformation (International Patent Application PCT/AU03/01111; International Patent Application PCT/JP2004/011958) or other method known in the art.

Alternatively the 3' end of the rose PPM1 cDNA clone is amplified using primers such as rosePPM F1 (SEQ ID NO: 104) (incorporating EcoRI and PstI recognition sites) and rose PPM1 R1 (SEQ ID NO: 107) (incorporating an EcoRI recognition site) or rosePPM F2 (SEQ ID NO: 105) (incorporating EcoRI and PstI recognition sites) and rose PPM1 R1 (SEQ ID NO: 107) or rosePPM F3 (SEQ ID NO: 106) (incorporating EcoRI and PstI recognition sites) and rose PPM1 R1 (SEQ ID NO: 107) [Table 12].

TABLE 12

Primers used in amplification of rose PPM1 fragments

| SEQ ID NO: | Sequence Name | Sequence (5' to 3') | Co-ordinates (SEQ ID NO: 98) |
|---|---|---|---|
| 104 | rosePPM F1 | GCAT GAATTCTGCAG CGTTATTTCCGCCCACAC | 2942-2959 |
| 105 | rosePPM F2 | GCAT GAATTCTGCAG TTATTTCCGCCCACACAG | 2944-2961 |
| 106 | rosePPM F3 | GCAT GAATTCTGCAG ATTTCCGCCCACACAGTC | 2946-2963 |
| 107 | rosePPM R1 | GCAT GAATTC TTATTACACAAAAACAGAAGGTC | 3222-3200 |

The PCR products are cloned into a cloning vector such as pCR2.1 (Invitrogen) and sequenced and compared to the nucleotide sequence of rosePPM1 (SEQ ID NO: 98) to ensure the correct product has been amplified. A fragment containing the rose PPM13' end is then released from the cloning vector using the restriction endonucleases PstI and EcoRI and the resulting 240 bp fragment is ligated with an ~5.9 kb PstI/EcoRI fragment of pKIWI101 containing a hybrid promoter consisting of a promoter region from CaMV 35S gene with enhancer elements from a promoter fragment of mannopine synthase (mas) gene of *Agrobacterium tumefaciens* and ~1.6 kb terminator fragment from octopine synthase gene of *A. tumefaciens* (described above). Correct insertion of the fragment is established by restriction endonuclease analysis of plasmid DNA isolated from ampicillin-resistant transformants. The resulting plasmid is then linearised with EcoRI. The PCR products of the 3' end of the rose PPM1 clone are then released on a ~240 bp fragment using EcoRI restriction digest and ligated with the linearised plasmid and correct insertion of the fragment in an antisense direction is established by restriction endonuclease analysis and sequencing of plasmid DNA isolated from ampicillin-resistant transformants. The ~2.4 kb fragment containing 35S: sense 3' rosePPM1/antisense 3' rosePPM1: ocs chimaeric gene is released upon digestion with XhoI/XbaI and the overhanging ends are repaired. The resulting 2.4 kb fragment is isolated and ligated with SmaI ends of the binary vector pCGP1969 (International Patent Application PCT/AU03/01111) or other binary vector containing F3'5'H genes (International Patent Application PCT/AU03/01111, International Patent Application PCT/JP2004/011958). The T-DNAs contained in the binary vector plasmids are introduced into *Rosa hybrida* cultivars such as but not limited to Kardinal, Soft Promise, Sonia, Medeo, Lavande via *Agrobacterium*-mediated transformation (International Patent Application PCT/AU03/01111 International Patent Application PCT/JP2004/011958) or other method known in the art.

EXAMPLE 7

Isolation of PPM cDNA Homologs from Carnation

Screening for a carnation PPM1 cDNA could utilize either combined rose and petunia probes or individual probes. Initially, a rose PPM1 probe was used to screen a carnation cDNA library.

Construction of Carnation cv. Kortina Chanel cDNA library

Twenty micrograms of total RNA was isolated from stages 1, 2 and 3 of Kortina Chanel (KC) flowers and reverse transcribed in a 50 µL volume containing 1× Superscript (Trademark) reaction buffer, 10 mM dithiothreitol (DTT), 500 µM dATP, 500 µM dGTP, 500 µM dTTP, 500 µM 5-methyl-dCTP, 2.8 µg Primer-Linker oligo from ZAP-cDNA Gigapack III Gold cloning kit (Stratagene) and 2 µL Superscript (Trademark) reverse transcriptase (BRL). The reaction mix was incubated at 37° C. for 60 minutes, then placed on ice. A ZAP-cDNA Gigapack III Gold Cloning kit (Stratagene) was used to complete the library construction. The total number of recombinants was $2.4 \times 10^6$.

The KC carnation petal cDNA library was subsequently titred, prior to screening for PPM1 sequences, at $1.95 \times 10^5$ pfu (total). A 25 mL Culture of XL1 Blue MRF' cells in 25 mL LB supplemented with 250 µL 20% Maltose and 250 µL 1M $MgSO_4$ was incubated until $OD_{600}$ 0.6-1. Cells were centrifuged at 4,000 rpm for 10 mins and then gently resuspended in 10 mM $MgSO_4$. The mixture was stored on ice. A 200 µL aliquot of the XL1 Blue MRF' cells was placed in a 12 mL falcon tube with a 10 µL aliquot of the diluted carnation petal cDNA library and incubated at 37° C. for 15 minutes. Five mL of NZY top agar (held at 50° C.) was then added and the contents were inverted gently to ensure no bubbles and then poured onto small (30 mL) NZY plates pre-warmed at 42° C. These were incubated at room temperature for around 15 minutes and allowed to set. Plates were then inverted and incubated at 37° C. overnight to allow plaques to form.

The KC carnation petal cDNA library was plated at 40,000 pfu per plate over 12 large plates thus including 500,000 plaques in the primary screen. A 25 mL culture of XL1 Blue MRF' cells in 25 mL LB supplemented with 250 µL 20% w/v maltose and 250 µL 1M $MgSO_4$ was incubated until $OD_{600}$ 0.6-1.0 Cells were centrifuged at 4,000 rpm (approx 3,000 g) for 10 mins in an eppendorf centrifuge and then gently resuspended in 10 mM $MgSO_4$ and placed on ice An appropriate dilution of the library was made to generate 40,000 pfu/10 µL per plate. Following the procedure outlined above 12 plates were generated for transfer to nylon membranes preparatory to screening for pH-modulating sequences such as PPM1, MAC9F1 and CAC16.5.

Following transfer the filters were transferred into prewash solution for 15 mins at 65° C. and then into denaturing solution for 15 mins at room temperature and then into neutralising solution for 15 mins at room temperature.

Filters were subjected to prehybridization (6 large per bottle) in 20 mL of 20% w/v NEN hybridisation mix (low stringency) at 42° C. for at least 1 hour before overnight hybridization at 42° C. with a $^{32}P$ labeled rose PPM1 DNA probe generated using PCR. Low stringency washes were carried out as follows: 6×SSC/1% w/v SDS 55° C. for 1 hr×2, 2×SSC/1% w/v SDS 42° C. for 40 mins, 2×SSC/1% w/v SDS 50° C. for 20 mins and 2×SSC/1% w/v SDS 65° C. for 30 minutes. Twenty-four putative positives were selected based on relative hybridization signal for secondary screening.

Positive "plugs" were excised and placed into an eppendorf tube containing 500 µL of PSB (phage storage buffer) [Sambrook et al., supra] and 20 µL chloroform. These were agitated for 4 hrs at room temperature and allowed to settle before removal of a 1 µL aliquot into PSB for plating as previously described. A total of 14 plaques were chosen for rescue and sequencing. As in the case of rose (see above) sequence analysis will reveal whether any of the clones isolated are in fact carnation PPM1 by virtue of sequence alignment and a closer examination of the C-terminal sequence of the deduced amino acid sequence derived from the cDNAs isolated as described.

EXAMPLE 8

Construction of a Plant Transformation Vector for Down Regulation of Carnation PPM1

The carnation PPM cDNA is used as a basis for construction of a plant transformation vectors aimed at down regulation or gene knockout of carnation PPM1 in carnation petals. Knockout of carnation PPM1 would thus lead to elevation of petal vacuolar pH and change in flower color. To achieve gene knockout a strategy aimed at production of dsRNA for carnation PPM1 is used. Thus a hairpin structure is engineered using the sequence of the cDNA from a region specific to the carnation PPM1 sequence and incorporated into both (i) constitutive, and (ii) petal-specific gene expression cassettes. In the former a CaMV 35S expression cassette (CaMV 35S promoter and terminator elements) and in the latter a petal specific promoter from carnation. A promoter from a carnation ANS gene is one example of a promoter for petal-specific expression which is used. The anthocyanin pathway genes provide a useful source of promoters for controlling petal-specific gene expression. However, such expression is not confined to the use of these promoters.

dsRNA (RNAi) gene silencing constructs are based on a 500 bp inverted repeat with an intervening 182 bp intron all under the control of 35S promoter or a petal specific promoter such as that from a carnation ANS gene.

Carnation PPM1—ANS Intermediate

Figure 9:
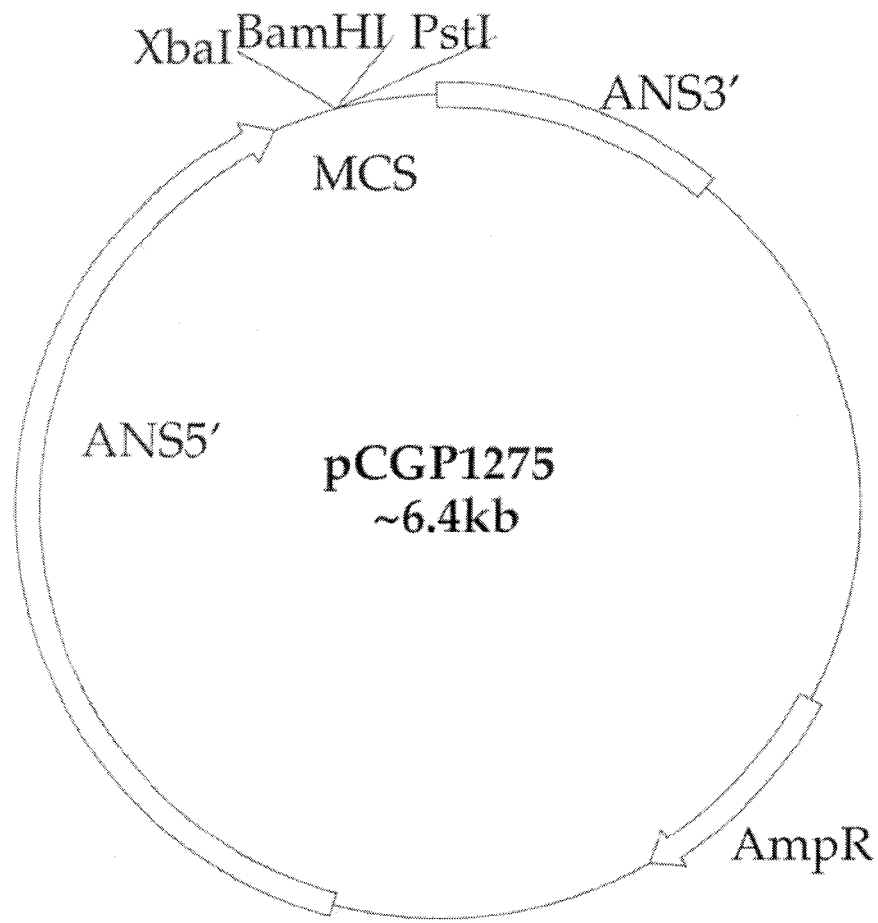
FIG. 9 is a diagrammatical representation of pCGP1275 (~6.4 kb).
Figure 10:
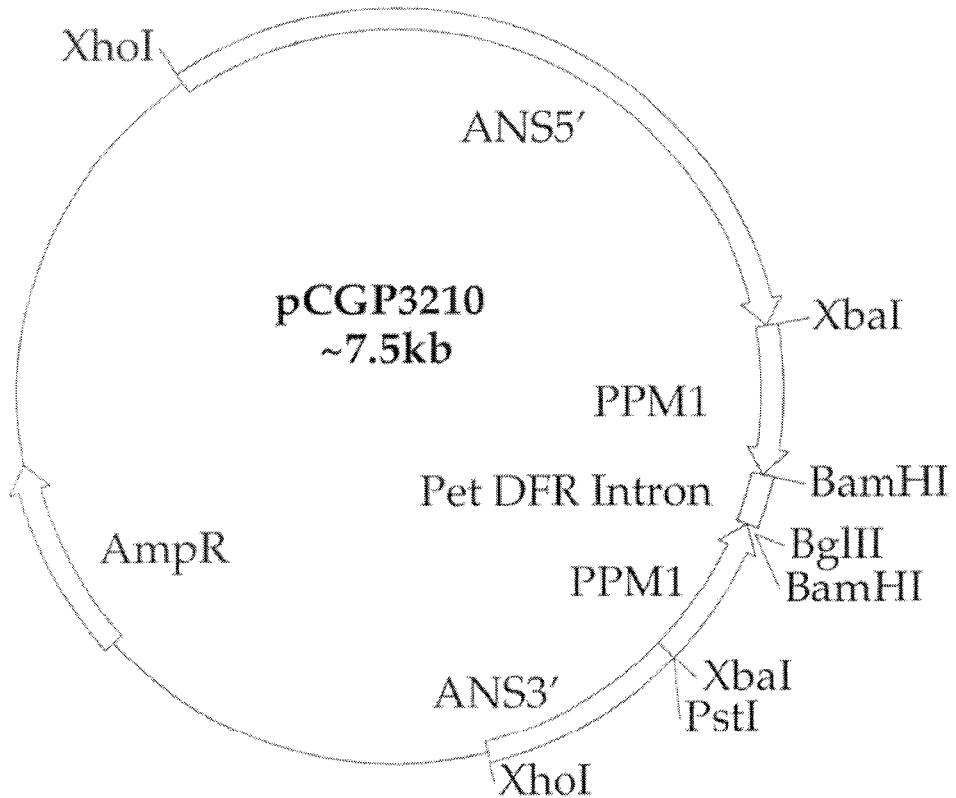
FIG. 10 is a diagrammatical representation of pCGP3210 (~7.5 kb).

The intron is cloned into pCGP1275 (FIG. 9) using BamHI creating pCGP1275i. The sense carnation PPMI (carnPPM1) is then cloned into pCGP1275i using XbaI/BamHI creating pCGP1275i-s-carnPPM1. The antisense PPM1 is then cloned into pCGP1275i-s-carnPPM1 using PstI/XbaI creating pCGP3210 (FIG. 10).

Carnation PPM1-ANS in pWTT2132 Binary Transformation Vector

Figure 11:
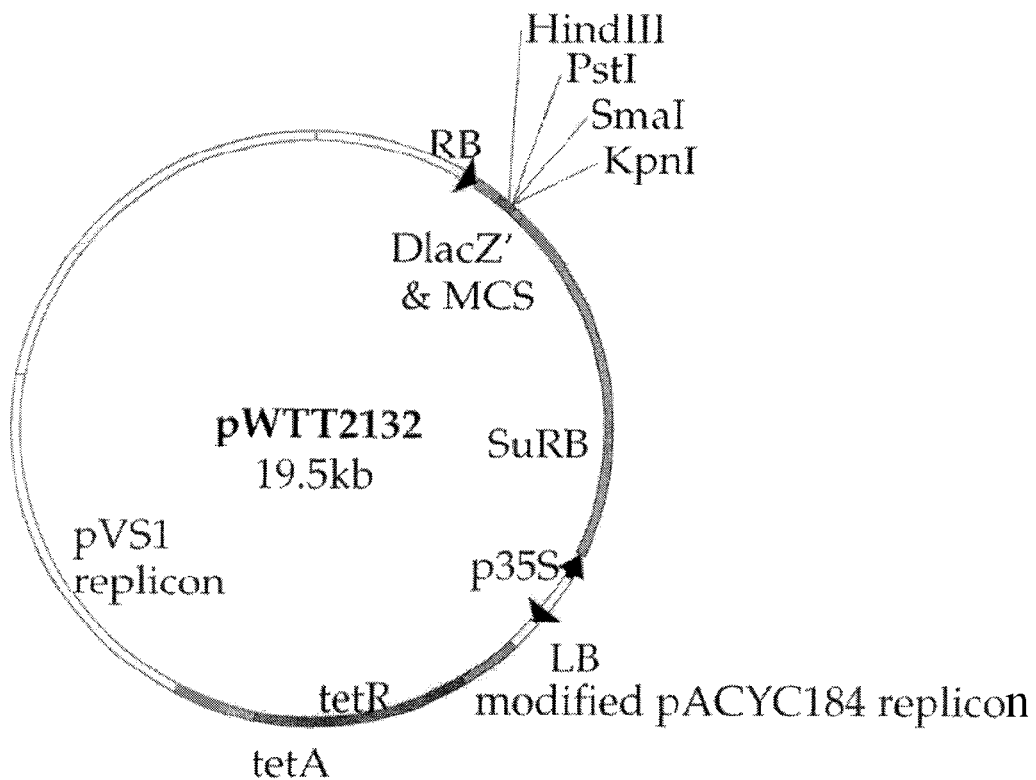
FIG. 11 is a diagrammatical representation of replicon pWTT2132 (~19.5 kb).
Figure 12:
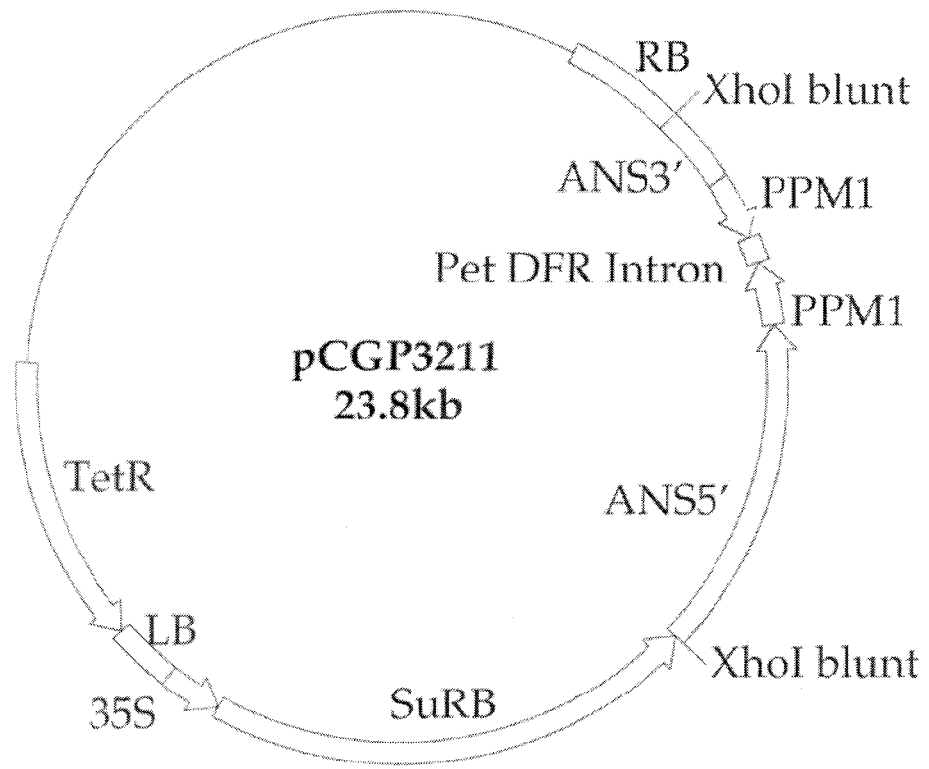
FIG. 12 is a diagrammatical representation of pCGP3211 (~23.8 kb).

The carnPPM1/ANS cassette is cut out of pCGP3210 with XhoI (blunt) and ligated into the binary transformation vector pWTT2132 (FIG. 11) to create the binary transformation vector pCGP3211 (FIG. 12)

Carnation PPM1—ANS in pBinPLUS Binary

Figure 13:
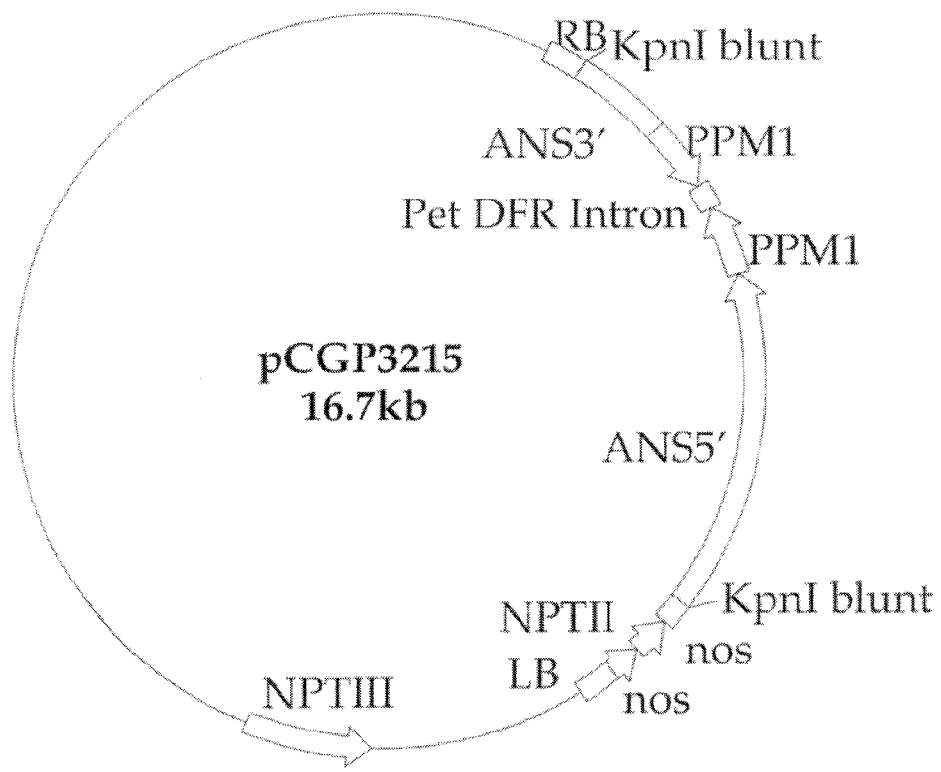
FIG. 13 is a diagrammatical representation of pCGP3215 (~16.7 kb).

The carnPPM1/ANS cassette is again cut out of pCGP3210 XhoI (blunt) and ligated into pBinPLUS KpnI (blunt) to create the binary transformation vector pCGP3215 (FIG. 13).

Carnation PPM1—ANS in pCGP2355 Binary

Figure 14:
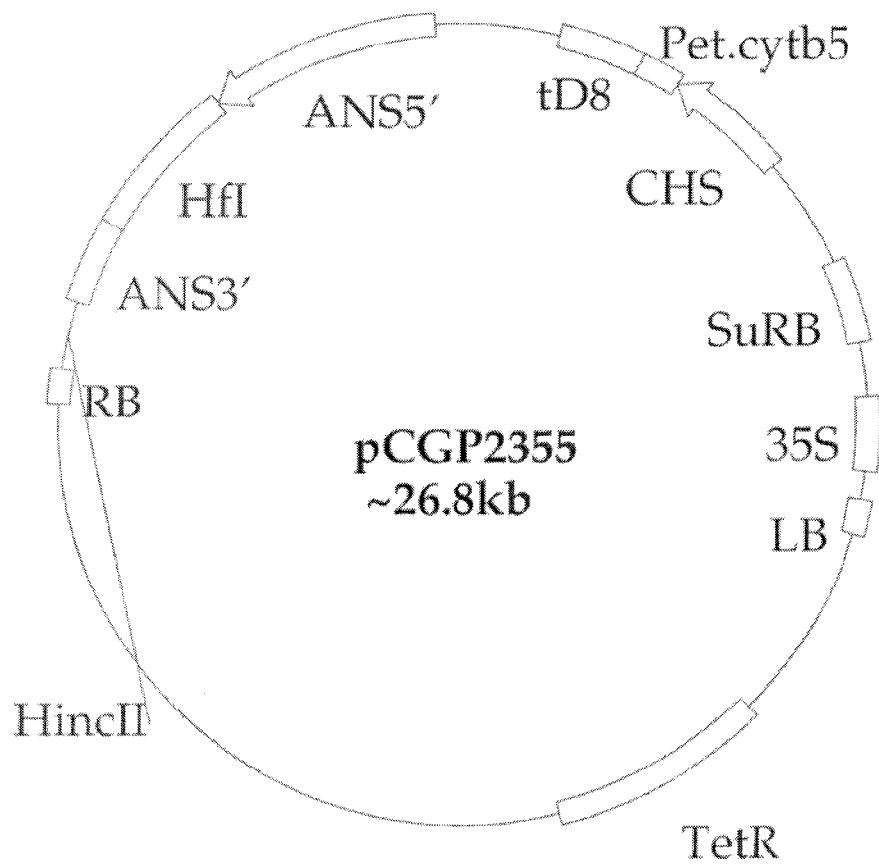
FIG. 14 is a diagrammatical representation of replicon pCGP2355 (~26.8 kb).
Figure 15:
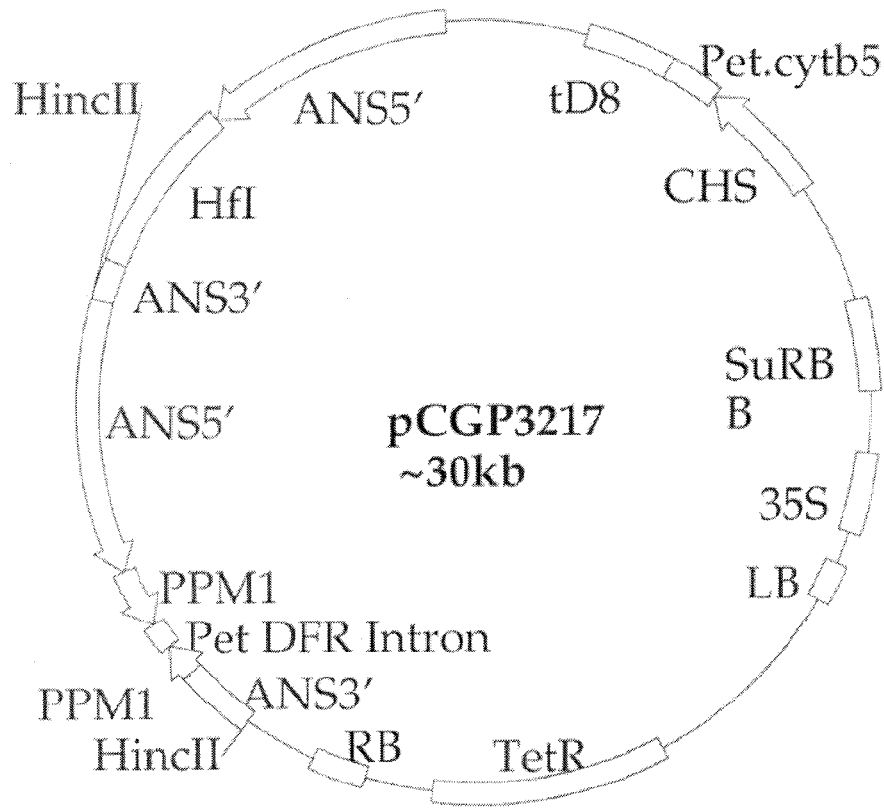
FIG. 15 is a diagrammatical representation of pCGP2355 (~30 kb).

The carnPPM1/ANS cassette is again cut out of pCGP3210 and ligated into pCGP2355 (FIG. 14) to create the binary transformation vector pCGP3217 (FIG. 15)

PPMI-35S Intermediate

Figure 16:
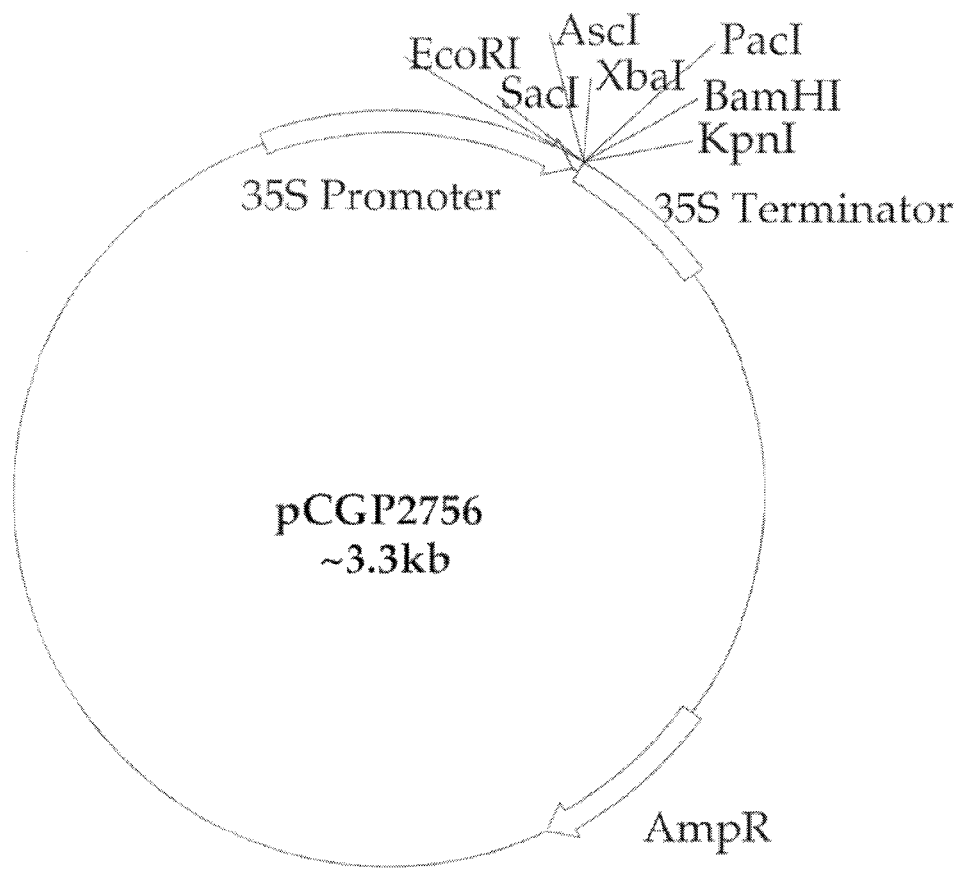
FIG. 16 is a diagrammatical representation of pCGP2756 (~3.3 kb).
Figure 17:
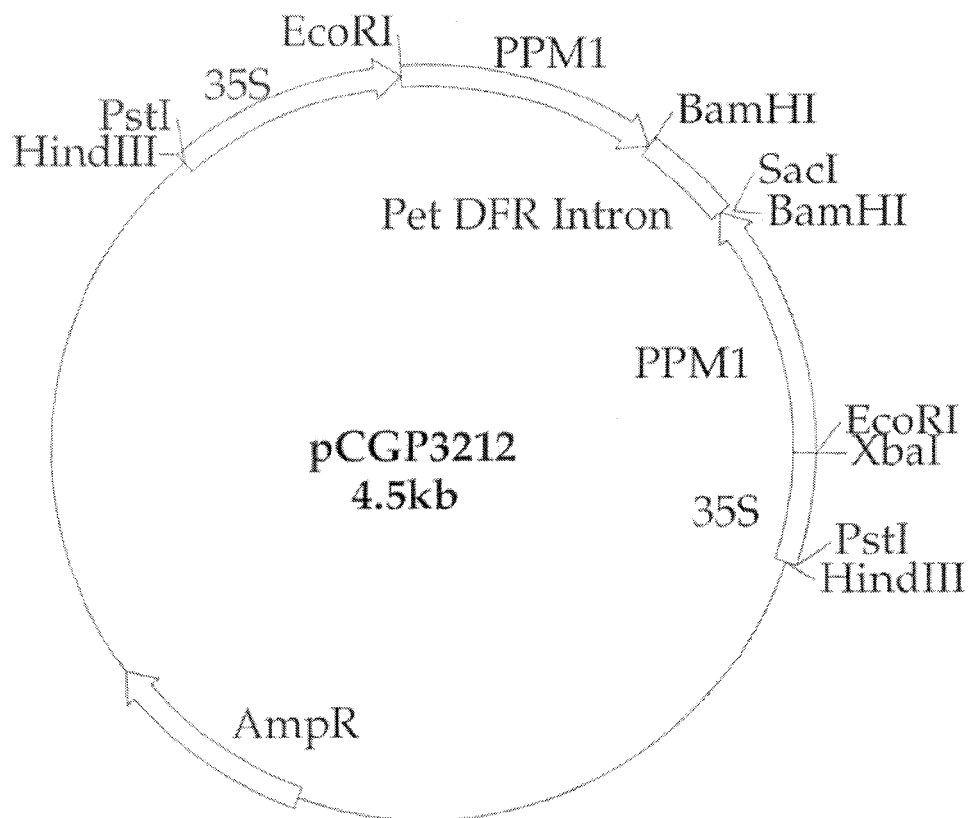
FIG. 17 is a diagrammatical representation of pCGP3212 (~4.5 kb).

The carnation ANS intron is cloned into pCGP2756 (FIG. 16) using BamHI creating pCGP2756i. The sense carnPPMI is cloned into pCGP2756i using EcoRI/BamHI creating pCGP2756i-s-carnPPM1. The antisense PPM1 is cloned into pCGP2756i-s-carnPPM1 using SacI/XbaI creating pCGP3212 (FIG. 17).

Carnation PPM1-35S in pWTT2132 Binary

Figure 18:
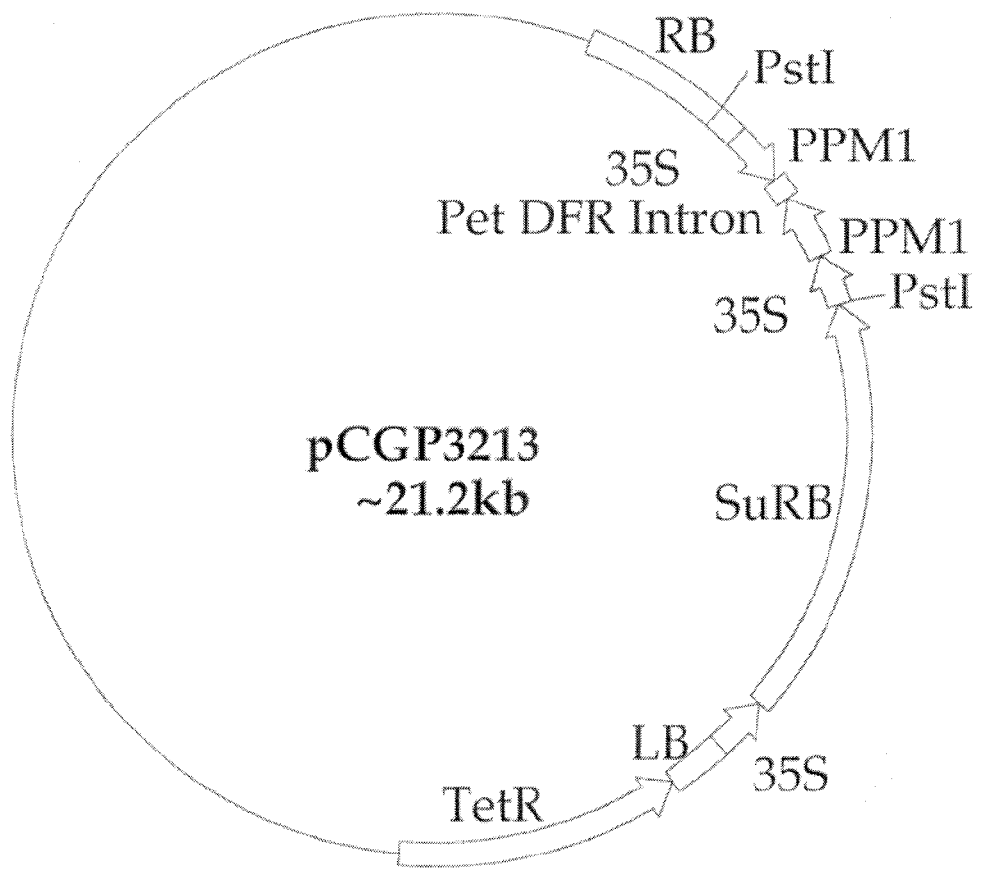
FIG. 18 is a diagrammatical representation of pCGP3213 (~21.2 kb).

The carnPPM1/ANS cassette will then be cut out of pCGP3212 with PstI to be ligated into pWTT2132 to create the binary transformation vector pCGP3213 (FIG. 18)

Carnation PPM1-35S in pBinPLUS Binary

Figure 19:
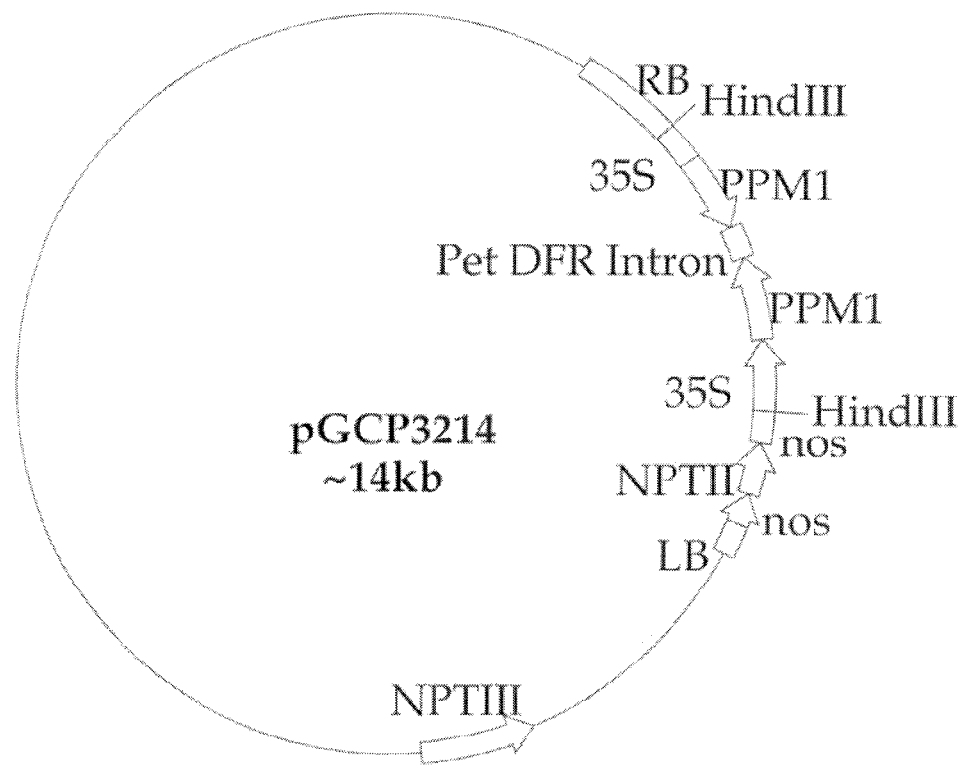
FIG. 19 is a diagrammatical representation of pGCP3214 ((~14 kb).

The carnPPM1/ANS cassette is then cut out of pCGP3212 with HindIII ligated into pWTT2132 to create the binary transformation vector pCGP3214 (FIG. 19).

Carnation PPM1-35S in pCGP2355 Binary

Figure 20:
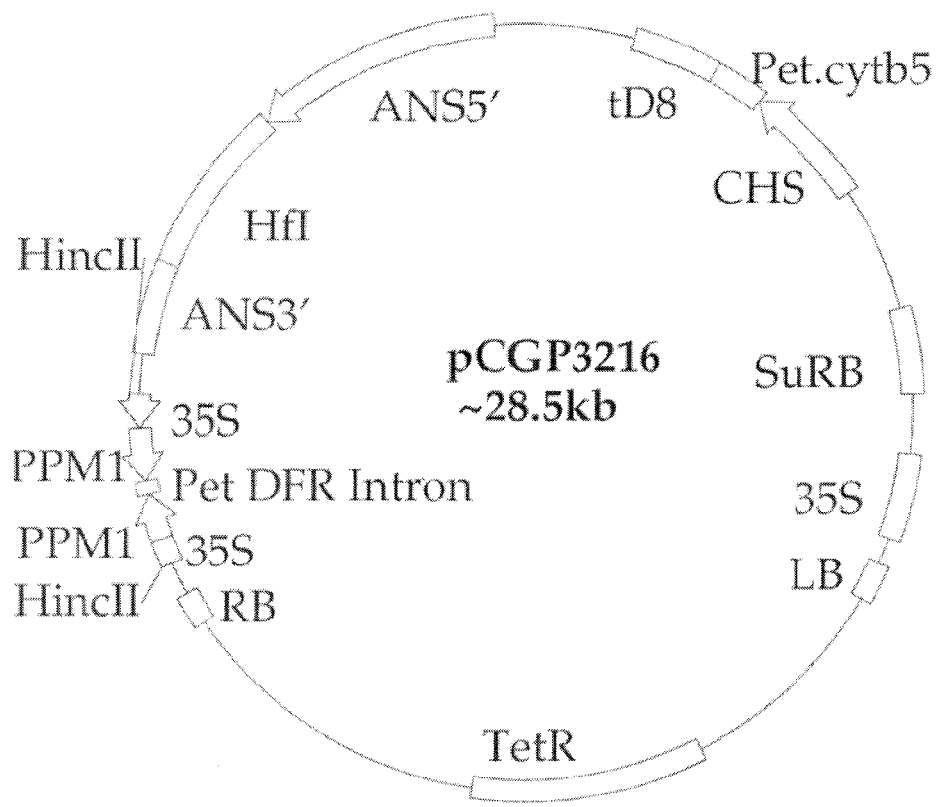
FIG. 20 is a diagrammatical representation of pCGP3216 (~28.5 kb).

The carnPPM1/ANS cassette is cut out of pCGP3212 with HindIII and ligated into pCGP2355 to create the binary transformation vector pCGP3216 (FIG. 20).

The transformation vectors generated above used to engineer pH-modulation in a number of different targets and tissues. In general, expression of pH-modulating sequences, such as silencing of carnation PPM1, is either constitutive or petal-specific. Targets for transformation include both carnations which produce delphinidin and those that do not. In each case assessment of the efficacy of pH modulation is measured through measurement of pH and/or visualization of color change.

EXAMPLE 9

Isolation of pH Modulating cDNAs from Other Species

Anthocyanins of an array of colors are produced in various species such as but not limited to *Alstroemeria* sp., *Anthurium* sp., Dracaena ap., *Erica* sp., *Ficus* sp., *Freesia* sp., *Fuchsia* sp., *Gladiolus* sp., *Petunia* sp., *Plumbago* sp., *Vitis* sp., *Babiana stricta, Pinus* sp., *Picea* sp., *Larix* sp., *Phaseolus* sp., *Solanum* sp., *Vaccinium* sp., *Cyclamen* sp., *Iris* sp., *Pelargo-* nium sp., *Geranium* sp., *Pisum* sp., *Lathyrus* sp., *Clitoria* sp., *Catharanthus* sp., *Malvia* sp., *Mucuna* sp., *Vicia* sp., *Saintpaulia* sp., *Lagerstroemia* sp., *Tibouchina* sp., *Hypocalyptus* sp., *Rhododendron* sp., *Linum* sp., *Macroptilium* sp., *Hibiscus* sp., *Helianthus* sp., *Hyacinth* sp., *Hypericum* sp., *Hydrangea* sp., *Impatiens* sp., *Iris* sp., *Chamelaucium* sp., *Kalanchoe* sp., *Lisianthus* sp., *Lobelia* sp., *Narcissus* sp., *Ipomoea* sp., *Nicotiana* sp., *Cymbidium* sp., *Millettia* sp., *Hedysarum* sp., *Lespedeza* sp., *Antigonon* sp., *Pisum* sp., *Begonia* sp., *Centaurea* sp., *Commelina* sp., *Rosa* sp., *Dianthus* sp. (carnation), *Chrysanthemum* sp. (chrysanthemums), *Dendranthema* sp., *Gerbera* sp., *Gentiana* sp. *Torenia* sp., *Nierembergia sp*, *Liatrus* sp. lily, *Gypsophila* sp., *Torenia* sp., orchid, *Dendrobium* sp., *Phalaenopsis* sp., *Iris* sp., *Ornithoglaum* sp., *Osteospermum* sp., *Paeonia* sp., *Pelargonium* sp., *Plumbago* sp., *Primrose* sp., *Ruscus* sp., *Saintpaulia* sp., *Solidago* sp., *Spathiphyllum* sp., *Tulip* sp., *Verbena* sp., *Viola* sp. and *Zantedeschia* sp.

These plants are proposed to contain pH modulating sequences and that down regulation of these pH modulating sequences results in a change in flower color.

Detection of Putative pH-Modulating Sequences in Other Plant Species

Figure 5:
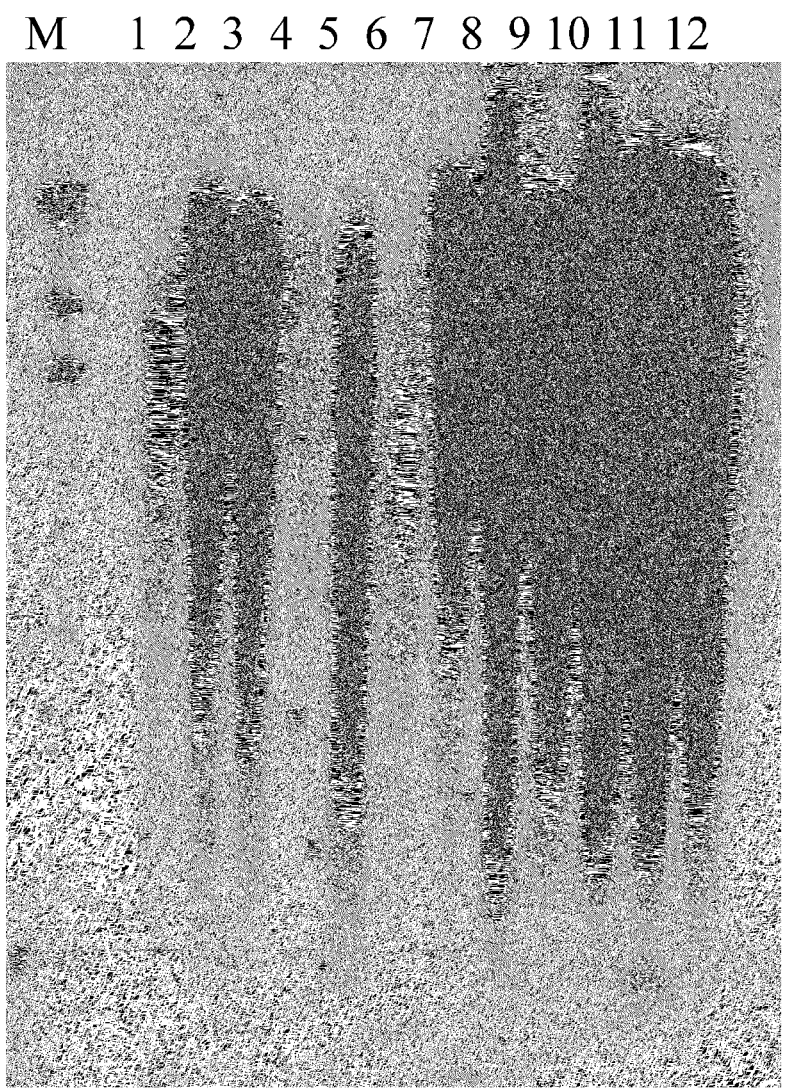
FIG. 5 is a photographic representation of an autoradiograph of a Southern blot probed with $^{32}$P-labeled Rose PPM1 fragment. Each lane contained 10 μg of DNA digested with EcoRI. Washing conditions were: twice in 6×SSC/1% w/w SDS at 50° C. for 1 hour. Lanes contain DNA from: M: markers, 1:Anemone , 2:Carnation, 3:Chrysanthemum, 4: Gerbera, 5:Hyacinth, 6:Iris, 7:Liatrus, 8:Pansy (Viola), 9:Petunia, 10:Nierembergia, 11:Rose, 12:Tobacco
Figure 6:
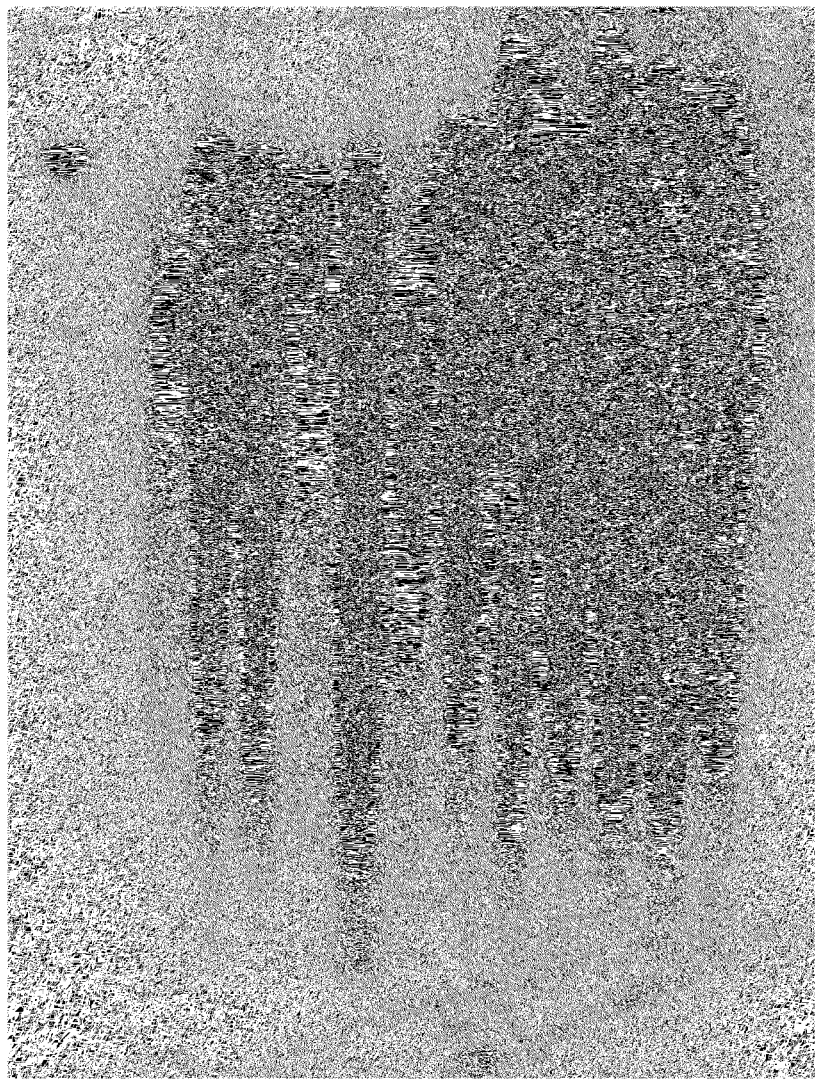
FIG. 6 is a photographic representation of an autoradiograph of a Southern blot probed with $^{32}$P-labeled Petunia CAC16.5 fragment. Each lane contained 10 μg of DNA digested with EcoRI. Washing conditions were: 6×SSC/1% w/w SDS at 50° C. for 30 minutes. Lanes contain DNA from: M: markers, 1:Anemone , 2:Carnation, 3:Chrysanthemum, 4: Gerbera, 5:Hyacinth, 6:Iris, 7:Liatrus, 8:Pansy (Viola), 9:Petunia, 10:Nierembergia, 11:Rose, 12:Tobacco
Figure 7:
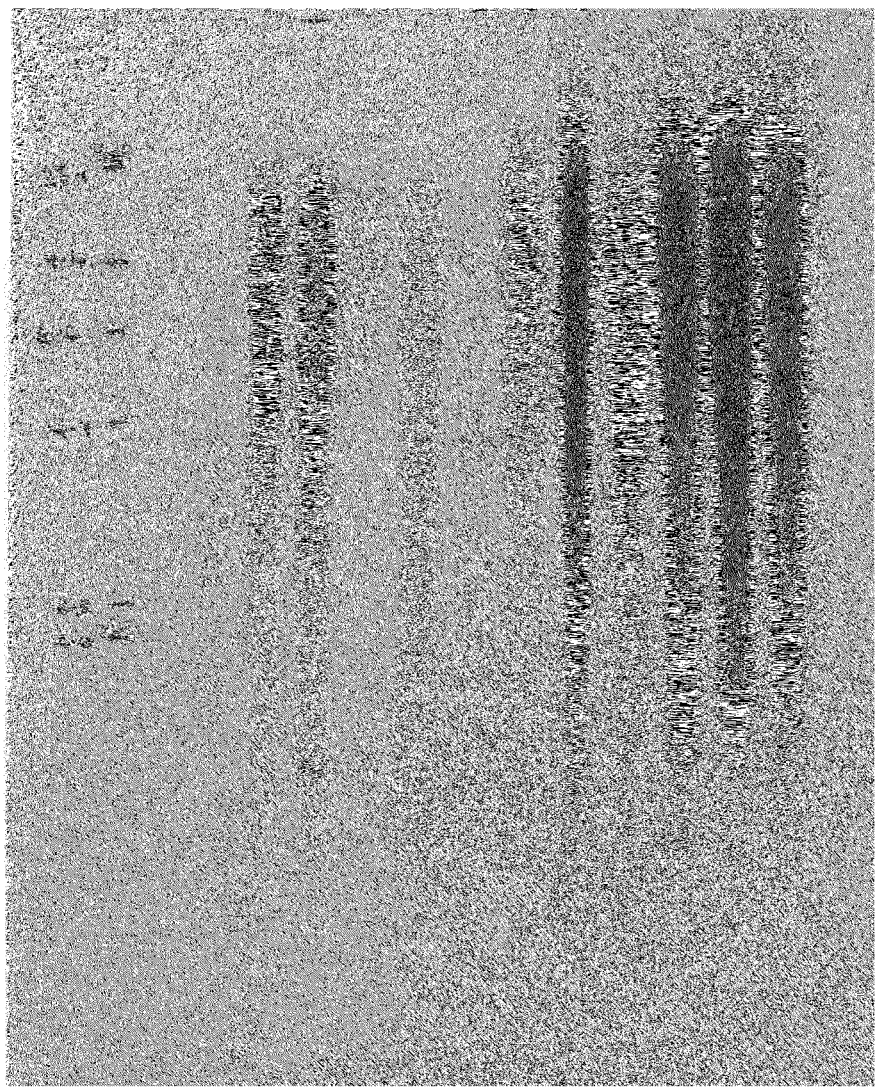
FIG. 7 is a photographic representation of an autoradiograph of a Southern blot probed with $^{32}$P-labeled Petunia MAC9F1 fragment. Each lane contained 10 μg of DNA digested with EcoRI. Washing conditions were: 6×SSC/1% w/w SDS at 50° C. for 30 minutes. Lanes contain DNA from: M: markers, 1:Anemone , 2:Carnation, 3:Chrysanthemum, 4: Gerbera, 5:Hyacinth, 6:Iris, 7:Liatrus, 8:Pansy (Viola), 9:Petunia, 10:Nierembergia, 11:Rose, 12:Tobacco

The presence of pH-modulating polypeptides such as PPM1 (SEQ ID NO:2 or 98) MAC9F1 (SEQ ID NO:4) and CAC16.5 (SEQ ID NO:6) or other sequences identified as such is correlated with the occurrence of genes encoding these proteins. It is expected that such genes from other species would hybridize with petunia sequences such as PPM1 (SEQ ID NO:1), MAC9 µl (SEQ ID NO:3) and CAC16.5 (SEQ ID NO:5) or rose PPM1 (SEQ ID 98) under conditions of low stringency. As an example of this DNA was isolated from a number of floral species and subjected to Southern analysis whereby fractionated DNA was transferred to a membrane and hybridized with (i) $^{32}$P-labeled rose PPM1 (SEQ ID NO:98), FIG. 5 or (ii) $^{32}$P-labeled petunia MAC9 µl (SEQ ID NO:3) and petunia CAC16.5 (SEQ ID NO:5), FIGS. 6 and 7, respectively. Therefore, the isolation of pH-modulating genes from other floral species is possible using petunia or rose probes from genes identified as encoding pH-modulating proteins.

The isolation of pH modulating cDNAs from the plants listed above and others is accomplished by the screening of respective petal cDNA libraries with SEQ ID NO:1 and/or 3 and/or 5 and/or 98 using low stringency hybridization conditions such as those described below or in the introduction of the instant specification.

Alternatively, the isolation of pH modulating cDNA fragments are accomplished using the polymerase chain reaction using primers such as those listed in the Examples above or specifically designed degenerate primers. The amplification products are cloned into bacterial plasmid vectors and DNA fragments used as probes to screen respective cDNA libraries to isolate longer and full-length pH modulating cDNA clones. The functionality and specificity of the cDNA clones are ascertained using methods described in Examples described above.

Isolation of pH Sequences from Other Species Such as Carnation, Gerbera, Chrysanthemum, Lily, Iris, Hyacinth, Pansy, Nierembergia, tobacco, Anenome etc.

The isolation of sequences that surprisingly modulate the pH of the petal vacuole without any obvious impact on other metabolic pathways (SEQ ID NO:1 to 6 and 98 and 99) allow the isolation similar sequences from other species by various molecular biology and/or protein chemistry methods. These include but are not limited to preparation of cDNA libraries from RNA isolated from petal tissue, screening the petal cDNA libraries using low stringency hybridization conditions using the labeled petunia or rose sequences (SEQ ID NO:1, 3, 5 and 98) as probes, sequencing the hybridizing purified cDNA clones and comparing these sequences and the deduced amino acid sequences with the petunia sequences (SEQ ID NO:1 to 6) or rose PPM1 sequence (SEQ ID NO: 98 and 99) and searching for any sequence identity and similarity, determining expression profiles of the isolated cDNA clones and selecting those that are preferentially expressed in petals, preparing gene constructs that allow for the specific sequence to be silenced in the plant using for example, antisense expression, co-suppression or RNAi expression. Ideally the plant of interest produces delphinidin (or its derivatives). This is achieved in one embodiment by expressing a Flavonoid 3', 5' hydroxylase (F3'5'H) sequence as described in International Patent Applications PCT/AU92/00334 and/or PCT/AU96/00296 and/or PCT/JP04/11958 and/or PCT/AU03/01111.

Preparation of Petal cDNA Libraries

Total RNA is isolated from the petal tissue of flowers using the method of Turpen and Griffith (*BioTechniques* 4: 11-15, 1986). Poly(A)$^+$ RNA is selected from the total RNA, using oligotex-dT (Trademark) (Qiagen) or by three cycles of oligo-dT cellulose chromatography (Aviv and Leder, *Proc. Natl. Acad. Sci. USA* 69: 1408, 1972).

µZAPII/Gigapack II Cloning kit (Stratagene, USA) (Short et al, *Nucl. Acids Res.* 16: 7583-7600, 1988) is used to construct directional petal cDNA libraries in λZAPII using around 5 µg of poly(A)$^+$ RNA isolated from petal as template.

After transfecting XL1-Blue MRF' cells, the packaged cDNA mixtures are plated at around 50,000 pfu per 15 cm diameter plate. The plates are incubated at 37° C. for 8 hours, and the phage is eluted in 100 mM NaCl, 8 mM MgSO$_4$, 50 mM Tris-HCl pH 8.0, 0.01% (w/v) gelatin (Phage Storage Buffer (PSB)) (Sambrook et al, 1989, supra). Chloroform is added and the phages stored at 4° C. as amplified libraries.

Around 100,000 or more pfu of the amplified libraries are plated onto NZY plates (Sambrook et al, 1989, supra) at a density of around 10,000 pfu per 15 cm plate after transfecting XL1-Blue MRF' cells, and are then incubated at 37° C. for 8 hours. After incubation at 4° C. overnight, duplicate lifts are taken onto Colony/Plaque Screen (Trademark) filters (DuPont) and are treated as recommended by the manufacturer.

Plasmid Isolation

Helper phage R408 (Stratagene, USA) is used to excise pBluescript phagemids containing cDNA inserts from amplified λZAPII or λZAP cDNA libraries using methods described by the manufacturer.

Screening of Petal cDNA Libraries

Prior to hybridization, duplicate plaque lifts are washed in prewashing solution (50 mM Tris-HCl pH7.5, 1 M NaCl, 1 mM EDTA, 0.1% w/v sarcosine) at 65° C. for 30 minutes; followed by washing in 0.4 M sodium hydroxide at 65° C. for 30 minutes; then washed in a solution of 0.2 M Tris-HCl pH 8.0, 0.1×SSC, 0.1% w/v SDS at 65° C. for 30 minutes and finally rinsed in 2×SSC, 1.0% w/v SDS.

The membrane lifts from the petal cDNA libraries are hybridized with $^{32}$P-labeled fragments of petunia PPM1 (SEQ ID NO:1) or petunia 9F1 (SEQ ID NO:3) or petunia CAC16.5 (SEQ ID NO:5) or rose PPM1 (SEQ ID NO:98).

Hybridization conditions include a prehybridization step in 10% v/v formamide, 1 M NaCl, 10% w/v dextran sulphate, 1% w/v SDS at 42° C. for at least 1 hour. The $^{32}$P-labeled fragments (each at 1×10$^6$ cpm/mL) are then added to the hybridization solution and hybridization is continued at 42° C. for a further 16 hours. The filters are then washed in 2×SSC, 1% w/v SDS at 42° C. for 2×1 hour and exposed to Kodak XAR film with an intensifying screen at −70° C. for 16 hours.

Strongly hybridizing plaques are picked into PSB (Sambrook et al, 1989, supra) and rescreened to isolate purified plaques, using plating and hybridization conditions as described for the initial screening of the cDNA library. The plasmids contained in the λZAPII or λZAP bacteriophage vectors are rescued and sequence data is generated from the 3' and 5' ends of the cDNA inserts. New pH modulating cDNA clones are identified based on nucleic acid and predicted amino acid sequence similarity to the petunia PPM1 (SEQ ID NO:1 and 2), MAC9F1 (SEQ ID NO:3 and 4) or CAC16.5 (SEQ ID NO:5 and 6) or rose PPM1 (SEQ ID NO:98 and 99).

EXAMPLE 10

Use of pH Modulating Sequences

In order to modulate (increase or decrease) the petal vacuolar pH in species or cultivars of species that do not normally produce delphinidin-based pigments and do not contain a flavonoid 3' 5' hydroxylases capable of hydroxylating dihydroflavonols, specifically dihydrokaempferol and/or dihydroquercetin, constructs containing the combination of a F3'5'H gene (such as but not limited to F3'5'H genes described in International Patent Applications PCT/AU92/00334 and/or PCT/AU03/0111) and a pH modulating or altering sequence are introduced into a species that does not normally produce delphinidin-based pigments. Such plants may include but are not limited to rose, carnation, chrysanthemum, gerbera, orchids, lily, gypsophila, *Euphorbia, Begonia* and apple.

In order to modulate the petal vacuolar pH in species or cultivars of species that produce delphinidin or cyanidin but have a vacuolar pH such that the color exhibited is not blue, constructs containing one or more pH modulating sequences are introduced into such species. Such plants include but are not limited to pansy, *Nierembergia*, lisianthus, cultivars of grapevine, lily, *Kalanchoe*, pelargonium, *Impatiens, Catharanthus*, cyclamen, *Torenia*, orchids, *Petunia*, iris and *Fuchsia*.

Construction of Plant Transformation Vectors for Down Regulation of pH Modulating Genes.

The above strategy is used to downregulate or silence pH modulating genes such as PPM1, MAC9F1 and CAC16.5 and their homologs in carnation, rose, gerbera, chrysanthemum and other floral species of commercial value. Typically such a strategy involves isolation of a homolog from the target species. However, the strategy is not confined to this approach as gene silencing technologies such as RNAi can be applied across species given conservation of appropriate sequences. Determination of whether such a strategy would be effective across species is determined through the isolation and characterization of homologs form a target species. Such characterization includes determination of the nucleotide sequence and subsequently the deduced amino acid sequence of pH-modulating genes such as PPM1, MAC9F1 and CAC16.5. A rose PPM1 sequence is, therefore, used to design effective pH-modulating gene silencing constructs for use in another species such as carnation, gerbera or chrysanthemum.

Binary transformation vectors, such as those described above, are used in plant transformation experiments to generate plants carrying the desired genes, in this case pH-modulating genes. It is in this fashion that the use of pH-modulating genes from petunia, rose and carnation to alter petal pH is intended and thus flower color in rose, carnation, gerbera, chrysanthemum and other floral species of commercial value.

Plant Transformations

*Rosa hybrida* Transformations

Introduction of pH modulating sequences into roses is achieved using methods as described in U.S. Pat. No. 542,841 (PCT/US91/04412) or Robinson and Firoozabady, *Scientia Horticulturae*, 55:83-99, 1993 or Rout et al, *Scientia Horticulturae*, 81:201-238, 1999 or Marchant et al, *Molecular Breeding* 4:187-194, 1998 or Li et al, *Plant Physiol Biochem.* 40:453-459, 2002 or Kim et al, *Plant Cell Tissue and Organ Culture* 78:107-111, 2004 or by any other method well known in the art.

*Dianthus caryophyllus* Transformations

Introduction of pH modulating sequences into carnations is achieved using methods as described in International Patent Application No. PCT/US92/02612, or International Patent Application No. PCT/AU96/00296, Lu et al, *Bio/Technology* 9:864-868, 1991, Robinson and Firoozabady, 1993 supra or by any other method well known in the art.

*Chrysanthemum* Transformations

Introduction of pH modulating sequences into chrysanthemum is achieved using methods as described in da Silva, *Biotechnology Advances*, 21:715-766, 2003 or Aswath et al, *Plant Science* 166:847-854, 2004 or Aida et al, *Breeding Sci.* 54:51-58, 2004 or by any other method well known in the art.

Gerbera Transformations

Introduction of pH modulating sequences into gerbera is achieved using methods as described in Elomaa and Teeri (In YPS Bajaj, ed, *Biotechnology in Agriculture and Forestry*, Transgenic Crops III., Springer-Verlag, Berlin 48:139-154, 2001) or by any other method well known in the art.

Ornamental Plant Transformations

Introduction of pH modulating sequences into ornamental plants is achieved using methods as described or reviewed in Deroles et al, (In: Geneve R L, Preece J E & Markle SA (eds) *Biotechnology of Ornamental Plants* CAB International, Wallingford 87-119, 1997) or Tanaka et al, (In: Chopra V L, Malik V S & Bhat S R (eds) *Applied Plant Biotechnology.* Oxford & IBH) New Delhi:177-231, 1999 or Tanaka et al, *Plant Cell, Tissue and Organ Culture* 80:1-24, 2005 by any other method well known in the art.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

Aida et al, *Breeding Sci.* 54:51-58, 2004
Altschul et al, *Nucl. Acids Res.* 25: 3389-3402, 1997
Altschul et al., *J. Mol. Biol.* 215(3): 403-410, 1990
Arango et al, *Planta,* 216:335-365, 2003
Aswath et al, *Plant Science* 166:847-854, 2004
Ausubel et al., "Current Protocols in Molecular Biology" John Wiley & Sons Inc, 1994-1998, Chapter 15.
Baxter et al, *PNAS,* 102:2649-2654, 2005
Bonner and Laskey, *Eur. J. Biochem.* 46: 83, 1974.
Brugliera et al, *Plant J.* 5, 81-92, 1994
da Silva, *Biotechnology Advances,* 21:715-766, 2003
de Vetten et al, *Genes Dev.* 11:1422-1434, 1997
de Vetten et al, *Plant Cell* 11(8):1433-1444, 1999
de Vlaming et al *Theor. Appl. Genet.* 66, 271-278, 1983

Deroles et al, (In: Geneve R L, Preece J E & Markle S A (eds) *Biotechnology of Ornamental Plants* CAB International, Wallingford 87-119, 1997
Di Sansebastiano et al, *Plant Physiology,* 126, 78-86, 2001
Elomaa and Teeri (In YPS Bajaj, ed, *Biotechnology in Agriculture and Forestry, Transgenic Crops III.*, Springer-Verlag, Berlin 48:139-154, 2001
Frohman et al, *PNAS* 85: 8998-9002, 1988
Fukada-Tanaka et al *Nature* 407, 581, 2000
Holton et al, *Nature* 366: 276-279, 1993
Holton and Cornish, *Plant Cell* 7:1071-1083, 1995
Huang and Miller, *Adv. Appl. Math.* 12: 373-381, 1991
Jahn et al, *JBC,* 277:6353-6358, 2002
Janssen and Gardner, *Plant Molecular Biology,* 14: 61-72, 1989
Kim et al, *Plant Cell Tissue and Organ Culture* 78:107-111, 2004
Koes et al, *Trends in Plant Science, May* 2005
Li et al, *Plant Physiol Biochem.* 40:453-459, 2002
Logemann et al, *Anal Biochem.* 163(1):16-20, 1987
Lu et al, *Bio/Technology* 9:864-868, 1991
Marchant et al, *Molecular Breeding* 4:187-194, 1998
Merrifield, *J. Am. Chem. Soc.* 85:2149, 1964
Mol et al, *Trends Plant Sci.* 3: 212-217, 1998
Pearson and Lipman, *Proc. Natl. Acad. Sci. USA* 85(8): 2444-2448, 1988
Plant Molecular Biology Labfax, Croy (ed), Bios scientific Publishers, Oxford, UK, 1993
Plant Molecular Biology Manual ($2^{nd}$ edition), Gelvin and Schilperoot (eds), Kluwer Academic Publisher, The Netherlands, 1994
Quattrocchio et al, *Plant J.* 13, 475-488, 1998
Quattrocchio et al, *Plant Cell,* 2005 (submitted)
Robinson and Firoozabady, *Scientia Horticulturae,* 55:83-99, 1993
Rout et al, *Scientia Horticulturae,* 81:201-238, 1999
Sambrook et al, *Molecular Cloning: A Laboratory Manual,* $2^{nd}$ edition, Cold Spring Harbor Laboratories, Cold Spring Harbor, N.Y., USA, 1989
Sambrook and Russell, Molecular Cloning: A Laboratory Manual $3^{rd}$ edition, Cold Spring Harbor Laboratories, Cold Spring Harbor, N.Y., USA, 2001
Spelt, C. et al. *Plant Cell* 14, 2121-2135, 2002
Tanaka et al., *Plant Cell Physiol* 37: 711-716, 1996
Tanaka et al, (In: Chopra V L, Malik V S & Bhat S R (eds) *Applied Plant Biotechnology*. Oxford & IBH), New Delhi: 177-231, 1999
Tanaka et al, *Plant Cell, Tissue and Organ Culture* 80:1-24, 2005
Thompson et al., *Nucleic Acids Research* 22: 4673-4680, 1994
van Houwelingen et al, *Plant J.* 13(1): 39-50, 1998
Verdonk et al. *Phytochemistry* 62:997-1008, 2003
Winkel-Shirley, *Plant Physiol.* 126: 485-493, 2001a
Winkel-Shirley, *Plant Physiol.* 127: 1399-1404, 2001b
Yoshida et al. *Nature* 373, 291, 1995

What is claimed is:

1. An isolated nucleic acid molecule comprising a sequence of nucleotides encoding a polypeptide having the amino acid sequence as set forth in SEQ ID NO: 99 or an amino acid sequence having at least 95% identity thereto, which comprises a Histidine-Threonine-Valine (HTV) amino acid sequence in the C-terminus and has a plasma membrane H⁺ATPase activity, wherein the nucleic acid molecule further comprises a heterologous nucleic sequence.

2. The isolated nucleic acid molecule of claim 1 wherein the sequence of nucleotides is as set forth in SEQ ID NO: 98 or a nucleotide sequence having at least 95% identity thereto.

3. The isolated nucleic acid molecule of claim 2 encoding a polypeptide having the amino acid sequence as set forth in SEQ ID NO: 99.

4. The isolated nucleic acid molecule of claim 2 comprising a nucleotide sequence as set forth in SEQ ID NO: 98.

5. The isolated nucleic acid molecule of claim 1 wherein the nucleotide sequence is from rose.

6. An RNAi construct comprising a sense or antisense fragment of the nucleic acid molecule of claim 1 that down-regulates expression of the nucleic acid molecule of claim 1, wherein the sense or antisense fragment of the nucleic acid molecule further comprises a heterologous nucleic acid sequence.

7. A method for elevating the pH in a vacuole of a plant cell from *Rosa* spp, said method comprising introducing into said plant cell the RNAi construct of claim 6, and wherein the RNAi construct is expressed.

8. A method for producing a transgenic flowering plant exhibiting altered inflorescence, said method comprising introducing into a cell of a plant from *Rosa* spp the RNAi construct of claim 6 and regenerating a transgenic plant comprising the RNAi construct from the cell, wherein the RNAi construct is expressed in the transgenic plant or plant cell.

9. A genetically modified, isolated cell or tissue of a transgenic plant produced in a method according to claim 8, which cell or tissue comprises said RNAi construct and comprises an increased pH in a vacuole of the cell or cells of the tissue as compared to the vacuolar pH in a cell or cells from tissues of a non-transgenic plant of the same species.

10. A plant part comprising a tissue of claim 9, wherein said plant part is selected from the group consisting of a flower, fruit, vegetable, nut, root, stem, leaf and seed.

11. An RNAi construct according to claim 6, which down-regulates expression of the nucleotide sequence set forth in SEQ ID NO: 98.

* * * * *

UNITED STATES PATENT AND TRADEMARK OFFICE
CERTIFICATE OF CORRECTION

PATENT NO.        : 8,629,258 B2                                              Page 1 of 1
APPLICATION NO. : 12/303091
DATED             : January 14, 2014
INVENTOR(S)       : Quattrocchio et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1165 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 107

<210> SEQ ID NO 1
<211> LENGTH: 3217
<212> TYPE: DNA
<213> ORGANISM: Petunia hybrida

<400> SEQUENCE: 1
gttctgattt tgaggatatt tgcatgcatg catgcactac ttgtaacgct agttgtagtt      60
gctaagggaa ttaaggtaca ttgatttggt caattttttt gttcacttgg attatcaaag    120
gcgcctcaag cagctacatt atcctattca tcactaaaca tggccgaaga tctggagaga    180
cctttactag gtcctgataa tttcagtcgg gaagggattg atctggaaaa gttgccactc    240
gaacaagttt ttgaagaatt aagaacatca aaggaagggc tttcagatga agatgcagag    300
gagcgactga acatattcgg gccaaacaag cttgaagaga agcgagagaa caagtttatt    360
aagtttcttg gcttcatgtg gaatcctttg tcttgggtga tggaagcagc cgcaatcatg    420
gcaattgctc tagctaatgg tggaggacaa ggtcctgact ggcaggactt tgtaggcatt    480
gtttgtctgt tgttgataaa ttcaacaatt agctttatag aggaaaataa tgctgggaat    540
gctgcagcag ctctcatggc acgtttagct cctagaacta aggtccttag agatgggagg    600
tggcaagaaa aagatgcagc tattctagtg ccaggagaca tcattagtat aaagcttggt    660
gatatcatcc ctgcagatgc ccgcttgctt gaagggatc ccttgaaagt agatcagtca    720
gctcttactg gggaatcctt acccgtcacg aaaaagacag gagatgaagt tttctctgga    780
tctacttgta acatggaga aattgaagca gtagtaattg ccactggagt tcactctttc    840
tttggaaaag ctgcacatct tgttgactcc actcaagtca ctggtcactt ccagaaggtc    900
cttgcttcta ttggaaattt ctgcatatgc tcaatagcaa tgggaatgat acttgaaatc    960
```

-continued

```
attgtcatgt tccctgttca gaatcgttca tataggactg gaattaacaa cctccttgtt      1020
ctcttaattg gtggaatacc aatagctatg ccaacagtcc tatcagttac tcttgctatt      1080
ggctctcatc gactctctca acagggtgct attacaaaaa ggatgactgc cattgaagag      1140
atggctggta tggatgtact ctgcagtgac aagacaggga cgctaaccct gaatcgcctc      1200
actattgata ggaatcttat tgaggtgttc caaaaagata tggacaaaga tatggttgtg      1260
ttacttgctg ccagagcatc aagactggaa atcaggatg ctattgatgc agcagttatc       1320
aacatgcttg ctgatccaaa ggaggcacgt gcaaatatca gggaagtgca tttccttcca      1380
ttcaatcctg tcgacaaacg gactgcaatc acttacattg attcagatgg aaagtggtat      1440
cgagcaagca aaggagctcc tgaacagatt ctgaccttgt gccaagagaa gcaacagata      1500
gctgcaaaag tgcacacgat cattgacaag tttgctgaaa gagggttacg atctcttgct      1560
gtttcctttc aggaaattcc agagaactca aaggagagtc ctggagggcc ttggcaattt      1620
tgtggattgc ttcccttgtt tgatccacca aggcacgata tgctgagac cattcggaga       1680 gcactcaact taggagtttg tgttaagatg attactggtg accagttggc cattgcaaag      1740
gaaacaggcc gacgcttgg catgggaaca aatatgtatc cctcatgttc gttgtttggt       1800
cgtgacaagg atgaaactga agctctacca gttgatgagc tcattgaaaa agcagatggc      1860
tttgctggtg tatttcctga gcacaaatat gagatagtaa aaatcctgca aatgaatgag      1920
cacgtggttg gaatgactgg tgatggagta aatgatgcac cagctctcaa gaaagcggat      1980
attggtatag cagtcgctga tgctacagat gctgctagga gtgctgctga tcttgtcttg      2040
actgagcctg gcttaagtgt gattgtcagt gctgttttga ctagcagggc tatatttcaa      2100
agaatgaaaa ttatacaatt catgcttctg gcgctaatat ggaaatatga ctttcctcca      2160
ttcatggtac tgataatagc aatcctaaat gatggcacta ttatgactat ttcaaaagat      2220
cgggttaaac catctccaag acctgatagt tggaagctta acgagatatt tgcaactggc      2280
gttgtgcttg gcacatatct tgctttagtt actgtgttgt tttactggct tgcagacagc      2340
actcaattct ttgaggctca cttccatgta aaatctctaa gtggaagtag tgaagaaatg      2400
tcatcagccg tttatctgca agtaagtatt atcagccagg cgctaatatt tgttacccgc      2460
agtcagagtt ggtcatttac agagagaccg ggggctcttt tgatgtttgc atttgtggtg      2520
gcacaactgg ttgctacctt gatagcagtt tatgcacata ttagcttcgc atcagttaga      2580
ggcatcggtt ggggatgggc aggtgtcata tggttataca gtcttatttt ctatattccc      2640
ttggatataa tcaaatttgc tgtttgttat gctctgactg gagaagcctg gaacctactt      2700
ttcgataaga agactgcttt tacgtcgaaa aaggactatg gaagggagga cagagaggcc      2760
cagtgggtgc tttctcagag aagtttacag cgggtaatat caccagagtt tgaacctaga      2820
agcaggaggc catctatgat tgctgaacaa gctaagcgtc gagccgaaat aaccaggctt      2880
agagagttgt acactttgag aggtcatata gaatcagtag caagactcaa gaatctggac      2940
cttaacaaaa ttcaaacagc tcatacagtt tgatatttga atctgcatga aatctcatct      3000
cctcctataa caaacttctg gctccatgtt gtcttttaag taactttcta tcatcatgtg      3060
gtccatgaga gacatgtcaa gaggcaatgt tgttcatgat cttctgccaa aaaaaccatg      3120
ttgaggatgt ttcttttgaag ctggacacct catatcattc attaatttct cccggggaag     3180
tgaatctagg acattgtatc atgcttttaa aaaaaaa                               3217
```

<210> SEQ ID NO 2
<211> LENGTH: 937
<212> TYPE: PRT

<213> ORGANISM: Petunia hybrida

<400> SEQUENCE: 2

Met Ala Glu Asp Leu Glu Arg Pro Leu Leu Gly Pro Asp Asn Phe Ser
1               5                   10                  15

Arg Glu Gly Ile Asp Leu Glu Lys Leu Pro Leu Glu Gln Val Phe Glu
            20                  25                  30

Glu Leu Arg Thr Ser Lys Glu Gly Leu Ser Asp Glu Asp Ala Glu Glu
        35                  40                  45

Arg Leu Asn Ile Phe Gly Pro Asn Lys Leu Glu Glu Lys Arg Glu Asn
50                  55                  60

Lys Phe Ile Lys Phe Leu Gly Phe Met Trp Asn Pro Leu Ser Trp Val
65                  70                  75                  80

Met Glu Ala Ala Ala Ile Met Ala Ile Ala Leu Ala Asn Gly Gly Gly
                85                  90                  95

Gln Gly Pro Asp Trp Gln Asp Phe Val Gly Ile Val Cys Leu Leu Leu
            100                 105                 110

Ile Asn Ser Thr Ile Ser Phe Ile Glu Glu Asn Asn Ala Gly Asn Ala
        115                 120                 125

Ala Ala Ala Leu Met Ala Arg Leu Ala Pro Arg Thr Lys Val Leu Arg
130                 135                 140

Asp Gly Arg Trp Gln Glu Lys Asp Ala Ala Ile Leu Val Pro Gly Asp
145                 150                 155                 160

Ile Ile Ser Ile Lys Leu Gly Asp Ile Ile Pro Ala Asp Ala Arg Leu
                165                 170                 175

Leu Glu Gly Asp Pro Leu Lys Val Asp Gln Ser Ala Leu Thr Gly Glu
            180                 185                 190

Ser Leu Pro Val Thr Lys Lys Thr Gly Asp Glu Val Phe Ser Gly Ser
        195                 200                 205

Thr Cys Lys His Gly Glu Ile Glu Ala Val Val Ile Ala Thr Gly Val
210                 215                 220

His Ser Phe Phe Gly Lys Ala Ala His Leu Val Asp Ser Thr Gln Val
225                 230                 235                 240

Thr Gly His Phe Gln Lys Val Leu Ala Ser Ile Gly Asn Phe Cys Ile
                245                 250                 255

Cys Ser Ile Ala Met Gly Met Ile Leu Glu Ile Ile Val Met Phe Pro
            260                 265                 270

Val Gln Asn Arg Ser Tyr Arg Thr Gly Ile Asn Asn Leu Leu Val Leu
        275                 280                 285

Leu Ile Gly Gly Ile Pro Ile Ala Met Pro Thr Val Leu Ser Val Thr
290                 295                 300

Leu Ala Ile Gly Ser His Arg Leu Ser Gln Gln Gly Ala Ile Thr Lys
305                 310                 315                 320

Arg Met Thr Ala Ile Glu Glu Met Ala Gly Met Asp Val Leu Cys Ser
                325                 330                 335

Asp Lys Thr Gly Thr Leu Thr Leu Asn Arg Leu Thr Ile Asp Arg Asn
            340                 345                 350

Leu Ile Glu Val Phe Gln Lys Asp Met Asp Lys Asp Met Val Val Leu
        355                 360                 365

Leu Ala Ala Arg Ala Ser Arg Leu Glu Asn Gln Asp Ala Ile Asp Ala
370                 375                 380

Ala Val Ile Asn Met Leu Ala Glu Ser Lys Glu Ala Arg Ala Asn Ile
385                 390                 395                 400

Arg Glu Val His Phe Leu Pro Phe Asn Pro Val Asp Lys Arg Thr Ala

```
              405                 410                 415
Ile Thr Tyr Ile Asp Ser Asp Gly Lys Trp Tyr Arg Ala Ser Lys Gly
            420                 425                 430

Ala Pro Glu Gln Ile Leu Thr Leu Cys Gln Glu Lys Gln Gln Ile Ala
            435                 440                 445

Ala Lys Val His Thr Ile Ile Asp Lys Phe Ala Glu Arg Gly Leu Arg
            450                 455                 460

Ser Leu Ala Val Ser Phe Gln Glu Ile Pro Glu Asn Ser Lys Glu Ser
465                 470                 475                 480

Pro Gly Gly Pro Trp Gln Phe Cys Gly Leu Leu Pro Leu Phe Asp Pro
                485                 490                 495

Pro Arg His Asp Ser Ala Glu Thr Ile Arg Arg Ala Leu Asn Leu Gly
            500                 505                 510

Val Cys Val Lys Met Ile Thr Gly Asp Gln Leu Ala Ile Ala Lys Glu
            515                 520                 525

Thr Gly Arg Arg Leu Gly Met Gly Thr Asn Met Tyr Pro Ser Cys Ser
            530                 535                 540

Leu Phe Gly Arg Asp Lys Asp Glu Thr Glu Ala Leu Pro Val Asp Glu
545                 550                 555                 560

Leu Ile Glu Lys Ala Asp Gly Phe Ala Gly Val Phe Pro Glu His Lys
                565                 570                 575

Tyr Glu Ile Val Lys Ile Leu Gln Met Asn Glu His Val Val Gly Met
                580                 585                 590

Thr Gly Asp Gly Val Asn Asp Ala Pro Ala Leu Lys Lys Ala Asp Ile
            595                 600                 605

Gly Ile Ala Val Ala Asp Ala Thr Asp Ala Ala Arg Ser Ala Ala Asp
            610                 615                 620

Leu Val Leu Thr Glu Pro Gly Leu Ser Val Ile Val Ser Ala Val Leu
625                 630                 635                 640

Thr Ser Arg Ala Ile Phe Gln Arg Met Lys Ile Ile Gln Phe Met Leu
                645                 650                 655

Leu Ala Leu Ile Trp Lys Tyr Asp Phe Pro Pro Phe Met Val Leu Ile
                660                 665                 670

Ile Ala Ile Leu Asn Asp Gly Thr Ile Met Thr Ile Ser Lys Asp Arg
            675                 680                 685

Val Lys Pro Ser Pro Arg Pro Asp Ser Trp Lys Leu Asn Glu Ile Phe
            690                 695                 700

Ala Thr Gly Val Val Leu Gly Thr Tyr Leu Ala Leu Val Thr Val Leu
705                 710                 715                 720

Phe Tyr Trp Leu Ala Asp Ser Thr Gln Phe Phe Glu Ala His Leu His
                725                 730                 735

Val Lys Ser Leu Ser Gly Ser Ser Glu Glu Met Ser Ser Ala Val Tyr
            740                 745                 750

Leu Gln Val Ser Ile Ile Ser Gln Ala Leu Ile Phe Val Thr Arg Ser
            755                 760                 765

Gln Ser Trp Ser Phe Thr Glu Arg Pro Gly Ala Leu Leu Met Phe Ala
770                 775                 780

Phe Val Val Ala Gln Leu Val Ala Thr Leu Ile Ala Val Tyr Ala His
785                 790                 795                 800

Ile Ser Phe Ala Ser Val Arg Gly Ile Gly Trp Gly Trp Ala Gly Val
                805                 810                 815

Ile Trp Leu Tyr Ser Leu Ile Phe Tyr Ile Pro Leu Asp Ile Ile Lys
                820                 825                 830
```

| | | | | | | | | | | | | |
|---|---|---|---|---|---|---|---|---|---|---|---|---|
|Phe|Ala|Val|Cys|Tyr|Ala|Leu|Thr|Gly|Glu|Ala|Trp|Asn|Leu|Leu|Phe|
| |835| | | | |840| | | | |845| | | | |

Asp Lys Lys Thr Ala Phe Thr Ser Lys Lys Asp Tyr Gly Arg Glu Asp
    850                 855                 860

Arg Glu Ala Gln Trp Val Leu Ser Gln Arg Ser Leu Gln Arg Val Ile
865                 870                 875                 880

Ser Pro Glu Phe Glu Pro Arg Ser Arg Arg Pro Ser Met Ile Ala Glu
            885                 890                 895

Gln Ala Lys Arg Arg Ala Glu Ile Thr Arg Leu Arg Glu Leu Tyr Thr
            900                 905                 910

Leu Arg Gly His Ile Glu Ser Val Ala Arg Leu Lys Asn Leu Asp Leu
            915                 920                 925

Asn Lys Ile Gln Thr Ala His Thr Val
            930                 935

<210> SEQ ID NO 3
<211> LENGTH: 687
<212> TYPE: DNA
<213> ORGANISM: Petunia hybrida
<220> FEATURE:
<221> NAME/KEY: misc_feature
<222> LOCATION: (9)..(9)
<223> OTHER INFORMATION: n is a, c, g, or t

<400> SEQUENCE: 3
ccttttcgnc gcgccgtcca ccaccaccaa catcaagatt ccttcttaag caggaaacta    60
ccagttgagc ctatggctgc accaagccta acaaaacagg agattgacaa gtattggaag   120
cagaagcgca tgactgaaga agaacatttt cttgatgcaa ttaaggctgc agccagaatc   180
agggcacgca atctctcgga ggaggactac acacacttcg tggattcttt gaaggaggat   240
ggtgattata aggagaatgg ggtaactaag aacatctcca aaattgatga ggacatgaag   300
gagcaaagag ttggcataaa agactggtgg acaaagagca atatgcttta tctaaaccag   360
ccagcagtga atcgatgga aggcaaaggc tcctcttata ttccccaatt atattgctac   420
aaggctcctc ctccaccagt tgcaaccact tttggcatat tctagggaat tttcatatat   480
acactcatat tcatgtattc gtattgtgct tgtagtatat aattgaattg ttaaagtgtg   540
catcctccaa agaattgtct catatgattg aaattgttgt aagtattgcg cttgcgaact   600
actttggttt tatgaaacca tgtgttaata ataatataa tggttctatt atattgttgg   660
atgcttgata taaaaaaaaa aaaaaaa                                      687

<210> SEQ ID NO 4
<211> LENGTH: 154
<212> TYPE: PRT
<213> ORGANISM: Petunia hybrida

<400> SEQUENCE: 4

Pro Phe Arg Arg Ala Val His His Gln His Gln Asp Ser Phe Leu
1               5                   10                  15

Ser Arg Lys Leu Pro Val Glu Pro Met Ala Ala Pro Ser Leu Thr Lys
            20                  25                  30

Gln Glu Ile Asp Lys Tyr Trp Lys Gln Lys Arg Met Thr Glu Glu Glu
        35                  40                  45

His Phe Leu Asp Ala Ile Lys Ala Ala Ala Arg Ile Arg Ala Arg Asn
    50                  55                  60

Leu Ser Glu Glu Asp Tyr Thr His Phe Val Asp Ser Leu Lys Glu Asp
65                  70                  75                  80

```
Gly Asp Tyr Lys Glu Asn Gly Val Thr Lys Asn Ile Ser Lys Ile Asp
                85                  90                  95

Glu Asp Met Lys Glu Gln Arg Val Gly Ile Lys Asp Trp Trp Thr Lys
            100                 105                 110

Ser Lys Tyr Ala Tyr Leu Asn Gln Pro Ala Val Lys Ser Met Glu Gly
        115                 120                 125

Lys Gly Ser Ser Tyr Ile Pro Gln Leu Tyr Cys Tyr Lys Ala Pro Pro
    130                 135                 140

Pro Pro Val Ala Thr Thr Phe Gly Ile Phe
145                 150

<210> SEQ ID NO 5
<211> LENGTH: 1169
<212> TYPE: DNA
<213> ORGANISM: Petunia hybrida
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t

<400> SEQUENCE: 5
ggcacgagtc tgcttttgaa tgggtgatca acaatggtgg cattgattca gcttctgatt      60
atccctatac tgcaattcaa ggcacttgca atatcaccaa ggagaagact aagattgtta     120
caatgatgga naccaagatg ttgcanaana ggaaagtgcc ctctctcttg tgctgctgcg     180
caacaacctg ttatgttggc ataatggctc tagcttggga tttccaacta tatacagggg     240
gaatttatga tggagattgt gtctacaatc caaatgatgt gcgaccatgc agtataatag     300
taggatatgg ttctgaagga atgaccaata ttggattatc aagaattcat ggggtacatc     360
ttggggaatg gagggtatgc atatataaaa aggaacactg atttgtcata tggtgttttgt     420 gccattaact caattgcttc atatccaacg aaagaatcgt cttcttcgtc gcctccttat     480
ccatctccag cccttccccc acctccaccg ccttctccat caccaagtga atgtggagac     540
tactatttct gttcaatagg ccaaacatgt tgctgtgagt tagagttgtt tggagtctgc     600
ttcattcagg gttgctgtcc ttatgaaaat ggtgtttgct gtgacaaatc agaatactgc     660
tgcccaagtg gctattctgt tgttctgtt aatcaaggca tgtgcctcaa ggagtatggc     720
gactatcttg gtggttgcca gcaaagaaga aagaatagc caagtacaag ttatcatgga     780
gtactagtac aaaattaaca atggagatgg accaacatct gcagtggaag aggaatgaat     840
ttttagaaat gctgaaggta cagttgatac taaagaagac tcttagcatt gtcaaatggt     900
ttccaggtac taaaggctag gacatataga tggttcttgc ttatgaaacc atgaataatt     960
acttcatgaa actttgctt gtttctaatt gatagtacta ttttcttgat attaaggatt    1020
gaatagtgag ttctgtgaca cctttaatgt tcttagtggc ccctcaaagt agaactctac    1080
aaagtgaatt cgtaaatgta ataatgtata tggatgctgt tgaatgtca ttacatttag    1140 gttgttttgt gaaaaaaaaa aaaaaaaaa                                      1169

<210> SEQ ID NO 6
<211> LENGTH: 130
<212> TYPE: PRT
<213> ORGANISM: Petunia hybrida
```

<400> SEQUENCE: 6

```
Met Ala Ala Pro Ser Leu Thr Lys Gln Glu Ile Asp Lys Tyr Trp Lys
1               5                   10                  15

Gln Lys Arg Met Thr Glu Glu His Phe Leu Asp Ala Ile Lys Ala
            20                  25                  30

Ala Ala Arg Ile Arg Ala Arg Asn Leu Ser Glu Glu Asp Tyr Thr His
            35                  40                  45

Phe Val Asp Ser Leu Lys Glu Asp Gly Asp Tyr Lys Glu Asn Gly Val
        50                  55                  60

Thr Lys Asn Ile Ser Lys Ile Asp Glu Asp Met Lys Glu Gln Arg Val
65                  70                  75                  80

Gly Ile Lys Asp Trp Trp Thr Lys Ser Lys Tyr Ala Tyr Leu Asn Gln
                85                  90                  95

Pro Ala Val Lys Ser Met Glu Gly Lys Gly Ser Ser Tyr Ile Pro Gln
            100                 105                 110

Leu Tyr Cys Tyr Lys Ala Pro Pro Pro Val Ala Thr Thr Phe Gly
        115                 120                 125

Ile Phe
130
```

<210> SEQ ID NO 7
<211> LENGTH: 16
<212> TYPE: DNA
<213> ORGANISM: Petunia hybrida

<400> SEQUENCE: 7
gacgatgagt cctgag         16

<210> SEQ ID NO 8
<211> LENGTH: 14
<212> TYPE: DNA
<213> ORGANISM: Petunia hybrida

<400> SEQUENCE: 8
tactcaggac tcat           14

<210> SEQ ID NO 9
<211> LENGTH: 19
<212> TYPE: DNA
<213> ORGANISM: Petunia hybrida

<400> SEQUENCE: 9
gacgatgagt cctgagtaa      19

<210> SEQ ID NO 10
<211> LENGTH: 20
<212> TYPE: DNA
<213> ORGANISM: Petunia hybrida

<400> SEQUENCE: 10
gacgatgagt cctgagtaaa     20

<210> SEQ ID NO 11
<211> LENGTH: 20
<212> TYPE: DNA
<213> ORGANISM: Petunia hybrida

<400> SEQUENCE: 11
gacgatgagt cctgagtaac     20

```
<210> SEQ ID NO 12
<211> LENGTH: 20
<212> TYPE: DNA
<213> ORGANISM: Petunia hybrida

<400> SEQUENCE: 12
gacgatgagt cctgagtaag                                               20

<210> SEQ ID NO 13
<211> LENGTH: 20
<212> TYPE: DNA
<213> ORGANISM: Petunia hybrida

<400> SEQUENCE: 13
gacgatgagt cctgagtaat                                               20

<210> SEQ ID NO 14
<211> LENGTH: 19
<212> TYPE: DNA
<213> ORGANISM: Petunia hybrida

<400> SEQUENCE: 14
gtgatatctc cactgacgt                                                19

<210> SEQ ID NO 15
<211> LENGTH: 17
<212> TYPE: DNA
<213> ORGANISM: Petunia hybrida

<400> SEQUENCE: 15
ctcgtagact gcgtacc                                                  17

<210> SEQ ID NO 16
<211> LENGTH: 15
<212> TYPE: DNA
<213> ORGANISM: Petunia hybrida

<400> SEQUENCE: 16
aattggtacg cagtc                                                    15

<210> SEQ ID NO 17
<211> LENGTH: 18
<212> TYPE: DNA
<213> ORGANISM: Petunia hybrida

<400> SEQUENCE: 17
agactgcgta ccaattca                                                 18

<210> SEQ ID NO 18
<211> LENGTH: 18
<212> TYPE: DNA
<213> ORGANISM: Petunia hybrida

<400> SEQUENCE: 18
agactgcgta ccaattcc                                                 18

<210> SEQ ID NO 19
<211> LENGTH: 18
<212> TYPE: DNA
<213> ORGANISM: Petunia hybrida

<400> SEQUENCE: 19
agactgcgta ccaattcg                                                 18
```

```
<210> SEQ ID NO 20
<211> LENGTH: 18
<212> TYPE: DNA
<213> ORGANISM: Petunia hybrida

<400> SEQUENCE: 20
gatgagtcct gagtaaaa                                                 18

<210> SEQ ID NO 21
<211> LENGTH: 18
<212> TYPE: DNA
<213> ORGANISM: Petunia hybrida

<400> SEQUENCE: 21
gatgagtcct gagtaaac                                                 18

<210> SEQ ID NO 22
<211> LENGTH: 18
<212> TYPE: DNA
<213> ORGANISM: Petunia hybrida

<400> SEQUENCE: 22
gatgagtcct gagtaaag                                                 18

<210> SEQ ID NO 23
<211> LENGTH: 18
<212> TYPE: DNA
<213> ORGANISM: Petunia hybrida

<400> SEQUENCE: 23
gatgagtcct gagtaaat                                                 18

<210> SEQ ID NO 24
<211> LENGTH: 18
<212> TYPE: DNA
<213> ORGANISM: Petunia hybrida

<400> SEQUENCE: 24
gatgagtcct gagtaaca                                                 18

<210> SEQ ID NO 25
<211> LENGTH: 18
<212> TYPE: DNA
<213> ORGANISM: Petunia hybrida

<400> SEQUENCE: 25
gatgagtcct gagtaacc                                                 18

<210> SEQ ID NO 26
<211> LENGTH: 18
<212> TYPE: DNA
<213> ORGANISM: Petunia hybrida

<400> SEQUENCE: 26
gatgagtcct gagtaacg                                                 18

<210> SEQ ID NO 27
<211> LENGTH: 18
<212> TYPE: DNA
<213> ORGANISM: Petunia hybrida

<400> SEQUENCE: 27
gatgagtcct gagtaact                                                 18
```

```
<210> SEQ ID NO 28
<211> LENGTH: 18
<212> TYPE: DNA
<213> ORGANISM: Petunia hybrida

<400> SEQUENCE: 28
gatgagtcct gagtaaga                                                 18

<210> SEQ ID NO 29
<211> LENGTH: 18
<212> TYPE: DNA
<213> ORGANISM: Petunia hybrida

<400> SEQUENCE: 29
gatgagtcct gagtaagc                                                 18

<210> SEQ ID NO 30
<211> LENGTH: 18
<212> TYPE: DNA
<213> ORGANISM: Petunia hybrida

<400> SEQUENCE: 30
gatgagtcct gagtaagg                                                 18

<210> SEQ ID NO 31
<211> LENGTH: 18
<212> TYPE: DNA
<213> ORGANISM: Petunia hybrida

<400> SEQUENCE: 31
gatgagtcct gagtaagt                                                 18

<210> SEQ ID NO 32
<211> LENGTH: 18
<212> TYPE: DNA
<213> ORGANISM: Petunia hybrida

<400> SEQUENCE: 32
gatgagtcct gagtaata                                                 18

<210> SEQ ID NO 33
<211> LENGTH: 18
<212> TYPE: DNA
<213> ORGANISM: Petunia hybrida

<400> SEQUENCE: 33
gatgagtcct gagtaatc                                                 18

<210> SEQ ID NO 34
<211> LENGTH: 18
<212> TYPE: DNA
<213> ORGANISM: Petunia hybrida

<400> SEQUENCE: 34
gatgagtcct gagtaatg                                                 18

<210> SEQ ID NO 35
<211> LENGTH: 18
<212> TYPE: DNA
<213> ORGANISM: Petunia hybrida

<400> SEQUENCE: 35
gatgagtcct gagtaatt                                                 18
```

```
<210> SEQ ID NO 36
<211> LENGTH: 18
<212> TYPE: DNA
<213> ORGANISM: Petunia hybrida

<400> SEQUENCE: 36
gactgcgtac caattcaa                                                 18

<210> SEQ ID NO 37
<211> LENGTH: 18
<212> TYPE: DNA
<213> ORGANISM: Petunia hybrida

<400> SEQUENCE: 37
gactgcgtac caattcac                                                 18

<210> SEQ ID NO 38
<211> LENGTH: 18
<212> TYPE: DNA
<213> ORGANISM: Petunia hybrida

<400> SEQUENCE: 38
gactgcgtac caattcag                                                 18

<210> SEQ ID NO 39
<211> LENGTH: 18
<212> TYPE: DNA
<213> ORGANISM: Petunia hybrida

<400> SEQUENCE: 39
gactgcgtac caattcat                                                 18

<210> SEQ ID NO 40
<211> LENGTH: 18
<212> TYPE: DNA
<213> ORGANISM: Petunia hybrida

<400> SEQUENCE: 40
gactgcgtac caattcca                                                 18

<210> SEQ ID NO 41
<211> LENGTH: 18
<212> TYPE: DNA
<213> ORGANISM: Petunia hybrida

<400> SEQUENCE: 41
gactgcgtac caattccc                                                 18

<210> SEQ ID NO 42
<211> LENGTH: 18
<212> TYPE: DNA
<213> ORGANISM: Petunia hybrida

<400> SEQUENCE: 42
gactgcgtac caattccg                                                 18

<210> SEQ ID NO 43
<211> LENGTH: 18
<212> TYPE: DNA
<213> ORGANISM: Petunia hybrida

<400> SEQUENCE: 43
gactgcgtac caattcct                                                 18
```

```
<210> SEQ ID NO 44
<211> LENGTH: 18
<212> TYPE: DNA
<213> ORGANISM: Petunia hybrida

<400> SEQUENCE: 44
gactgcgtac caattcga                                                 18

<210> SEQ ID NO 45
<211> LENGTH: 18
<212> TYPE: DNA
<213> ORGANISM: Petunia hybrida

<400> SEQUENCE: 45
gactgcgtac caattcgc                                                 18

<210> SEQ ID NO 46
<211> LENGTH: 18
<212> TYPE: DNA
<213> ORGANISM: Petunia hybrida

<400> SEQUENCE: 46
gactgcgtac caattcgg                                                 18

<210> SEQ ID NO 47
<211> LENGTH: 18
<212> TYPE: DNA
<213> ORGANISM: Petunia hybrida

<400> SEQUENCE: 47
gactgcgtac caattcgt                                                 18

<210> SEQ ID NO 48
<211> LENGTH: 18
<212> TYPE: DNA
<213> ORGANISM: Petunia hybrida

<400> SEQUENCE: 48
gactgcgtac caattcta                                                 18

<210> SEQ ID NO 49
<211> LENGTH: 18
<212> TYPE: DNA
<213> ORGANISM: Petunia hybrida

<400> SEQUENCE: 49
gactgcgtac caattctc                                                 18

<210> SEQ ID NO 50
<211> LENGTH: 18
<212> TYPE: DNA
<213> ORGANISM: Petunia hybrida

<400> SEQUENCE: 50
gactgcgtac caattctg                                                 18

<210> SEQ ID NO 51
<211> LENGTH: 18
<212> TYPE: DNA
<213> ORGANISM: Petunia hybrida

<400> SEQUENCE: 51
gactgcgtac caattctt                                                 18
```

```
<210> SEQ ID NO 52
<211> LENGTH: 23
<212> TYPE: DNA
<213> ORGANISM: Petunia hybrida

<400> SEQUENCE: 52
ggaccttaac aaaattcaaa cag                                   23

<210> SEQ ID NO 53
<211> LENGTH: 21
<212> TYPE: DNA
<213> ORGANISM: Petunia hybrida

<400> SEQUENCE: 53
aaattaatga atgatatgag g                                     21

<210> SEQ ID NO 54
<211> LENGTH: 20
<212> TYPE: DNA
<213> ORGANISM: Petunia hybrida

<400> SEQUENCE: 54
tgaagaaatg tcatcagccg                                       20

<210> SEQ ID NO 55
<211> LENGTH: 20
<212> TYPE: DNA
<213> ORGANISM: Petunia hybrida

<400> SEQUENCE: 55
gttcagcaat catagatggc                                       20

<210> SEQ ID NO 56
<211> LENGTH: 21
<212> TYPE: DNA
<213> ORGANISM: Petunia hybrida

<400> SEQUENCE: 56
gctctgactg gagaagcctg g                                     21

<210> SEQ ID NO 57
<211> LENGTH: 26
<212> TYPE: DNA
<213> ORGANISM: Petunia hybrida

<400> SEQUENCE: 57
ccaagagaag caacagatag ctgcaa                                26

<210> SEQ ID NO 58
<211> LENGTH: 26
<212> TYPE: DNA
<213> ORGANISM: Petunia hybrida

<400> SEQUENCE: 58
ttgcagctat ctgttgcttc tcttgg                                26

<210> SEQ ID NO 59
<211> LENGTH: 26
<212> TYPE: DNA
<213> ORGANISM: Petunia hybrida

<400> SEQUENCE: 59
gaatcaatgt aagtgattgc agtccg                                26
```

```
<210> SEQ ID NO 60
<211> LENGTH: 24
<212> TYPE: DNA
<213> ORGANISM: Petunia hybrida

<400> SEQUENCE: 60
aactgatagg actgttggca tagc                                          24

<210> SEQ ID NO 61
<211> LENGTH: 23
<212> TYPE: DNA
<213> ORGANISM: Petunia hybrida

<400> SEQUENCE: 61
gctggtgcat catttactcc atc                                           23

<210> SEQ ID NO 62
<211> LENGTH: 23
<212> TYPE: DNA
<213> ORGANISM: Petunia hybrida

<400> SEQUENCE: 62
atggccgaag atctggagag acc                                           23

<210> SEQ ID NO 63
<211> LENGTH: 23
<212> TYPE: DNA
<213> ORGANISM: Petunia hybrida

<400> SEQUENCE: 63
ctgcagggat gatatcacca agc                                           23

<210> SEQ ID NO 64
<211> LENGTH: 26
<212> TYPE: DNA
<213> ORGANISM: Petunia hybrida

<400> SEQUENCE: 64
ctgataatag caatcctaaa tgatgg                                        26

<210> SEQ ID NO 65
<211> LENGTH: 36
<212> TYPE: DNA
<213> ORGANISM: Petunia hybrida

<400> SEQUENCE: 65
cggaattcat ggccgaagat ctggagagac ctttac                             36

<210> SEQ ID NO 66
<211> LENGTH: 36
<212> TYPE: DNA
<213> ORGANISM: Petunia hybrida

<400> SEQUENCE: 66
cccgggcttc tccagtcaga gcatatcaaa cagcaa                             36

<210> SEQ ID NO 67
<211> LENGTH: 31
<212> TYPE: DNA
<213> ORGANISM: Petunia hybrida

<400> SEQUENCE: 67
aagaattcgt ttgttatgct ctgactggag a                                  31
```

```
<210> SEQ ID NO 68
<211> LENGTH: 24
<212> TYPE: DNA
<213> ORGANISM: Petunia hybrida

<400> SEQUENCE: 68
gactgcgggt aacaaatatt agcg                                              24

<210> SEQ ID NO 69
<211> LENGTH: 25
<212> TYPE: DNA
<213> ORGANISM: Petunia hybrida

<400> SEQUENCE: 69
gcaaatatca gggaagtgca tttcc                                             25

<210> SEQ ID NO 70
<211> LENGTH: 37
<212> TYPE: DNA
<213> ORGANISM: Petunia hybrida

<400> SEQUENCE: 70
cggaattctc gcaaatatca gggaagtgca tttcctt                                37

<210> SEQ ID NO 71
<211> LENGTH: 30
<212> TYPE: DNA
<213> ORGANISM: Petunia hybrida

<400> SEQUENCE: 71
ttatgaatca atgtaagtga ttgcagtccg                                        30

<210> SEQ ID NO 72
<211> LENGTH: 29
<212> TYPE: DNA
<213> ORGANISM: Petunia hybrida

<400> SEQUENCE: 72
tagcccatgg ccgaagatct ggagagacc                                         29

<210> SEQ ID NO 73
<211> LENGTH: 33
<212> TYPE: DNA
<213> ORGANISM: Petunia hybrida

<400> SEQUENCE: 73
catgagccat ggacaaactg tatgagctgt ttg                                    33

<210> SEQ ID NO 74
<211> LENGTH: 25
<212> TYPE: DNA
<213> ORGANISM: Petunia hybrida

<400> SEQUENCE: 74
gcttgctgat ccaaggagg cacgt                                              25

<210> SEQ ID NO 75
<211> LENGTH: 22
<212> TYPE: DNA
<213> ORGANISM: Petunia hybrida

<400> SEQUENCE: 75
gtaaggattc cccagtaaga gc                                                22
```

```
<210> SEQ ID NO 76
<211> LENGTH: 34
<212> TYPE: DNA
<213> ORGANISM: Petunia hybrida

<400> SEQUENCE: 76
cgggatcctg agccagaaag tttgttatag gagg                          34

<210> SEQ ID NO 77
<211> LENGTH: 22
<212> TYPE: DNA
<213> ORGANISM: Petunia hybrida

<400> SEQUENCE: 77
ggtcttggag atggtttaac cc                                       22

<210> SEQ ID NO 78
<211> LENGTH: 25
<212> TYPE: DNA
<213> ORGANISM: Petunia hybrida

<400> SEQUENCE: 78
gctgctagga gtgctgctga tcttg                                    25

<210> SEQ ID NO 79
<211> LENGTH: 28
<212> TYPE: DNA
<213> ORGANISM: Petunia hybrida

<400> SEQUENCE: 79
gcatgataca atgtcctaga ttcacttc                                 28

<210> SEQ ID NO 80
<211> LENGTH: 30
<212> TYPE: DNA
<213> ORGANISM: Petunia hybrida

<400> SEQUENCE: 80
ctaaccatgg ccgaagacct ggagagacct                               30

<210> SEQ ID NO 81
<211> LENGTH: 45
<212> TYPE: DNA
<213> ORGANISM: Petunia hybrida

<400> SEQUENCE: 81
gtttgatcag acgtcacatg tctccaaact gtatgagctg tttga              45

<210> SEQ ID NO 82
<211> LENGTH: 21
<212> TYPE: DNA
<213> ORGANISM: Petunia hybrida

<400> SEQUENCE: 82
gttcgcaagc gcaatactta c                                        21

<210> SEQ ID NO 83
<211> LENGTH: 20
<212> TYPE: DNA
<213> ORGANISM: Petunia hybrida

<400> SEQUENCE: 83
ggaattcggc acgaggtcac                                          20
```

-continued

```
<210> SEQ ID NO 84
<211> LENGTH: 18
<212> TYPE: DNA
<213> ORGANISM: Petunia hybrida

<400> SEQUENCE: 84
aagagtagct gatcatgg                                                 18

<210> SEQ ID NO 85
<211> LENGTH: 25
<212> TYPE: DNA
<213> ORGANISM: Petunia hybrida

<400> SEQUENCE: 85
gatgaggaca tgaaggagca aagag                                         25

<210> SEQ ID NO 86
<211> LENGTH: 24
<212> TYPE: DNA
<213> ORGANISM: Petunia hybrida

<400> SEQUENCE: 86
cttcagtctt gcgtttctgc ttcc                                          24

<210> SEQ ID NO 87
<211> LENGTH: 24
<212> TYPE: DNA
<213> ORGANISM: Petunia hybrida

<400> SEQUENCE: 87
ctcctgtttt gtcaggcttg gtgc                                          24

<210> SEQ ID NO 88
<211> LENGTH: 22
<212> TYPE: DNA
<213> ORGANISM: Petunia hybrida

<400> SEQUENCE: 88
cggcggcggt ggacttgtct tc                                            22

<210> SEQ ID NO 89
<211> LENGTH: 35
<212> TYPE: DNA
<213> ORGANISM: Petunia hybrida

<400> SEQUENCE: 89
gctctagact agaatatgcc aaaagtggtt gcaac                              35

<210> SEQ ID NO 90
<211> LENGTH: 36
<212> TYPE: DNA
<213> ORGANISM: Petunia hybrida

<400> SEQUENCE: 90
atcgaattca tggctgcacc aagcctaaca aaacag                             36

<210> SEQ ID NO 91
<211> LENGTH: 37
<212> TYPE: DNA
<213> ORGANISM: Petunia hybrida

<400> SEQUENCE: 91
accgctcgag ctagaatatg ccaaaagtgg ttgcaac                            37
```

```
<210> SEQ ID NO 92
<211> LENGTH: 21
<212> TYPE: DNA
<213> ORGANISM: Petunia hybrida

<400> SEQUENCE: 92
cctgtatata gttggaaatc c                                              21

<210> SEQ ID NO 93
<211> LENGTH: 21
<212> TYPE: DNA
<213> ORGANISM: Petunia hybrida

<400> SEQUENCE: 93
caaggcactt gcaatatcac c                                              21

<210> SEQ ID NO 94
<211> LENGTH: 23
<212> TYPE: DNA
<213> ORGANISM: Petunia hybrida

<400> SEQUENCE: 94
gtaatgacat tcaaacagca tcc                                            23

<210> SEQ ID NO 95
<211> LENGTH: 25
<212> TYPE: DNA
<213> ORGANISM: Petunia hybrida

<400> SEQUENCE: 95
cttcgtcgcc tccttatcca tctcc                                          25

<210> SEQ ID NO 96
<211> LENGTH: 22
<212> TYPE: DNA
<213> ORGANISM: Petunia hybrida

<400> SEQUENCE: 96
ggattatcaa gaattcatgg gg                                             22

<210> SEQ ID NO 97
<211> LENGTH: 23
<212> TYPE: DNA
<213> ORGANISM: Petunia hybrida

<400> SEQUENCE: 97
gcctccttat ccatctccag ccc                                            23

<210> SEQ ID NO 98
<211> LENGTH: 3269
<212> TYPE: DNA
<213> ORGANISM: Rosa hybrida

<400> SEQUENCE: 98
gcttcgtcgc agaggaggag gaggaggaag aaggaagaag gaaggagctt cgtccctctt     60
cccgcgcttc cgaaatactt ggatactgat tggaagctcg aatcatggct gaagatctgg    120
acaaaccgtt gttggatcct gagaatttca atagagatgg catcgatttg gaacgcttac    180
ccctggaaga agtttttgaa caactgagaa catcagcgag aggactttca tccgatgatg    240
ctgaagccag attgcacatt tttggctaca caaacttga agagaagaca gagaacaaaa    300
ttttgaagtt tcttagcttt atgtggaacc ccttgtcatg ggttatggaa gctgcagcag    360
```

```
ttatggcact tgtccttgct aatggggag gtgagggtcc tgactggcaa gactttgttg      420
ggattattgt cctattaata atcaattcaa caattagttt catagaggag aataatgcgg     480
gaaatgctgc atcagctctt atggaacgtt tatctccaaa gacaagggtt ctcagagatg    540
ggcagtggca agagcaagat gcaggtattt tagtgccagg agacataatt agcataaagc    600
tcggggatat aattccagct gatgctcgtc tacttgaagg agaccctctg aaagttgatc    660
agtcggctct tacaggagag tctctggctg tcaccaagag gacaggtgat gaagtatttt    720
ctggttcaac atgtaagcat ggagaaattg aagctgtagt gatagcaacc ggagttcact    780
cattttttgg aaaagcagca catttagtcg acaccactga agttgtggga catttccagc    840
aggtccttac tgccattggg aatttctgca tttgctctat agctgtggga atggttcttg    900
aaatcattgt catgttcccc atacagcaac gttcttacag ggatggaatc aacaaccttc    960
ttgttctctt aattggagga attccaattg ctatgccaac agtgttatct gtgacacttg   1020
caattggttc tcatcgacta tctcaacagg gtgctattac aaaaaggatg acagcaattg   1080
aagaaatggc gggaatggat gtccctttgta gtgacaaaac tggaactctt accctgaacc   1140
gcctcactgt tgataaaaac ctggttgagg ttttttaacaa taatatagac agagacacag   1200
ttatcttatt tgcagccaga gcagcaagac tggagaatca agacgcaatt gatgcagcca   1260
ttaccaatat gcttggtgat ccaaaggagg cacgtgcaaa cattaccgaa gtgcattttc   1320
tgcccttcaa tccagtggac aagcgtactg ccattacata catcgactct gatggtaatt   1380
ggtatagggc cagcaaagga gctccagaac agattctaga tctttgccct gagaaaaatg   1440
agattgctgg aagagtacat agcaccattg acaaatttgc tgaaagaggc ttgcggtctc   1500
ttggagttgc ttatcaggaa gttccagaaa aaactaaaga aagccctggc ggtccttgga   1560
ccttttgtgg gttgttgccc ttgtttgatc ctccgaggca tgacagtgct gagaccattc   1620
gtagagcact taaccttgga gtcgctgtga agatgattac aggtgaccag ttggcaattg   1680
cgaaggagac agggagacgg cttggtatgg gaacaaacat gtatccttcc tcttcattat   1740
tgggccgcaa aaaagaagaa gaccacgaag ccgtgccagt ggacgagctg attgagaagg   1800
cagatggctt tgctggtgtc ttccctgaac acaagtatga aattgtaaaa atcttacaag   1860
aaaagaagca tgtcgttgga atgactggag atggcgttaa cgatgcacct gctttaaaga   1920
aagcagacat tggtatagca gtggcagatt ccacagatgc tgcgagaagt gcttctgata   1980
tagtcttaac ggaacctggc ttaagtgtca ttgtcagtgc tgtcctgacc agtcgagcta   2040
tattccagag aatgaagaat tatactatat atgctgtttc cattaccatt aggattgtgc   2100
ttggtttcgt gcttcttgca ttgatatggg agtatgattt cccacctttc atggttctga   2160
ttatagcaat actgaatgat gggaccatca tgacaatttc ccaagatcgg gtaaagccct   2220
ctccaaagcc tgacagttgg aagttgaatg agatatttgc aactggcatt gtcattggta   2280
catatctagc tttggttact gtgttatttt actggactgt cattgagacc accttctttg   2340
aggacacctt tggcttaatg tctatatccg acaacagtga ggaagtttca tctgctgtat   2400
atctgcaagt tagcatcata agtcaagctc tcatatttgt tacccgaagt caaggatggt   2460
catttcttga gagacctgga gctctgttga tgattgcatt tgttgtggct caactggtgg   2520
ctactctgat tgccgtctat gcggaaatca gctttgctta cattagcggc attggatggg   2580
gatgggctgg agtcatatgg ttgtatagtt tgatttttcta cttcccttg gacattatca    2640 agttcgcaat tcgctatgcc ttgagtggag atgcctggaa tttattgttt gatagaaaga   2700
cagcttttac tgctaagaaa gattatggga aggaagacag ggcagctaaa tgggtacttt   2760
```

-continued

```
ctcagagaac tttacagggg ttgcatgaca tggagttcaa ggcaggtaga actagcccca    2820
aaaatgctgg ttggattgcc gaacaggcca gacggcgcgc tgaaatagcc aggttgggag    2880
agctacacac tatgagagga catgtagaat ctgtaatgag ctaaaaaat ttggacccga     2940 acgttatttc cgcccacaca gtctgaagcc aatacatgga gacagtagta ttcaattttc    3000
tggtgaaaga aaattctgca gcatttgctc acataattga tgtttgggta tctgcaaaag   3060
aaattgacat ttggttacca gattttttt tgggatggcg taggtaactc tctgtaatgt     3120
tgtcaattct ttgggtgcta aaagtaagga gtatatttc ctagtattaa tttgtcttaa     3180
ttttcaatgt atacaagggg accttctgtt tttgtgtaat aattaggcta cttgaaacta    3240
ataaacccac atgctagagt ggaattttc                                      3269
```

<210> SEQ ID NO 99
<211> LENGTH: 953
<212> TYPE: PRT
<213> ORGANISM: Rosa hybrida

<400> SEQUENCE: 99

```
Met Ala Glu Asp Leu Asp Lys Pro Leu Leu Asp Pro Glu Asn Phe Asn
1               5                   10                  15

Arg Asp Gly Ile Asp Leu Glu Arg Leu Pro Leu Glu Glu Val Phe Glu
            20                  25                  30

Gln Leu Arg Thr Ser Ala Arg Gly Leu Ser Ser Asp Ala Glu Ala
        35                  40                  45

Arg Leu His Ile Phe Gly Tyr Asn Lys Leu Glu Glu Lys Thr Glu Asn
    50                  55                  60

Lys Ile Leu Lys Phe Leu Ser Phe Met Trp Asn Pro Leu Ser Trp Val
65                  70                  75                  80

Met Glu Ala Ala Ala Val Met Ala Leu Val Leu Ala Asn Gly Gly Gly
                85                  90                  95

Glu Gly Pro Asp Trp Gln Asp Phe Val Gly Ile Val Leu Leu Ile
            100                 105                 110

Ile Asn Ser Thr Ile Ser Phe Ile Glu Glu Asn Asn Ala Gly Asn Ala
        115                 120                 125

Ala Ser Ala Leu Met Glu Arg Leu Ser Pro Lys Thr Arg Val Leu Arg
    130                 135                 140

Asp Gly Gln Trp Gln Glu Gln Asp Ala Gly Ile Leu Val Pro Gly Asp
145                 150                 155                 160

Ile Ile Ser Ile Lys Leu Gly Asp Ile Ile Pro Ala Asp Ala Arg Leu
                165                 170                 175

Leu Glu Gly Asp Pro Leu Lys Val Asp Gln Ser Ala Leu Thr Gly Glu
            180                 185                 190

Ser Leu Ala Val Thr Lys Arg Thr Gly Asp Glu Val Phe Ser Gly Ser
        195                 200                 205

Thr Cys Lys His Gly Glu Ile Glu Ala Val Val Ile Ala Thr Gly Val
    210                 215                 220

His Ser Phe Phe Gly Lys Ala Ala His Leu Val Asp Thr Thr Glu Val
225                 230                 235                 240

Val Gly His Phe Gln Gln Val Leu Thr Ala Ile Gly Asn Phe Cys Ile
                245                 250                 255

Cys Ser Ile Ala Val Gly Met Val Leu Glu Ile Ile Val Met Phe Pro
            260                 265                 270

Ile Gln Gln Arg Ser Tyr Arg Asp Gly Ile Asn Asn Leu Leu Val Leu
        275                 280                 285
```

```
Leu Ile Gly Gly Ile Pro Ile Ala Met Pro Thr Val Leu Ser Val Thr
            290                 295                 300

Leu Ala Ile Gly Ser His Arg Leu Ser Gln Gln Gly Ala Ile Thr Lys
305                 310                 315                 320

Arg Met Thr Ala Ile Glu Glu Met Ala Gly Met Asp Val Leu Cys Ser
                325                 330                 335

Asp Lys Thr Gly Thr Leu Thr Leu Asn Arg Leu Thr Val Asp Lys Asn
                340                 345                 350

Leu Val Glu Val Phe Asn Asn Asn Ile Asp Arg Asp Thr Val Ile Leu
            355                 360                 365

Phe Ala Ala Arg Ala Ala Arg Leu Glu Asn Gln Asp Ala Ile Asp Ala
370                 375                 380

Ala Ile Thr Asn Met Leu Gly Asp Pro Lys Glu Ala Arg Ala Asn Ile
385                 390                 395                 400

Thr Glu Val His Phe Leu Pro Phe Asn Pro Val Asp Lys Arg Thr Ala
                405                 410                 415

Ile Thr Tyr Ile Asp Ser Asp Gly Asn Trp Tyr Arg Ala Ser Lys Gly
                420                 425                 430

Ala Pro Glu Gln Ile Leu Asp Leu Cys Pro Lys Asn Glu Ile Ala
                435                 440                 445

Gly Arg Val His Ser Thr Ile Asp Lys Phe Ala Glu Arg Gly Leu Arg
450                 455                 460

Ser Leu Gly Val Ala Tyr Gln Glu Val Pro Glu Lys Thr Lys Glu Ser
465                 470                 475                 480

Pro Gly Gly Pro Trp Thr Phe Cys Gly Leu Leu Pro Leu Phe Asp Pro
                485                 490                 495

Pro Arg His Asp Ser Ala Glu Thr Ile Arg Arg Ala Leu Asn Leu Gly
                500                 505                 510

Val Ala Val Lys Met Ile Thr Gly Asp Gln Leu Ala Ile Ala Lys Glu
                515                 520                 525

Thr Gly Arg Arg Leu Gly Met Gly Thr Asn Met Tyr Pro Ser Ser Ser
                530                 535                 540

Leu Leu Gly Arg Lys Lys Glu Glu Asp His Glu Ala Val Pro Val Asp
545                 550                 555                 560

Glu Leu Ile Glu Lys Ala Asp Gly Phe Ala Gly Val Phe Pro Glu His
                565                 570                 575

Lys Tyr Glu Ile Val Lys Ile Leu Gln Glu Lys Lys His Val Val Gly
                580                 585                 590

Met Thr Gly Asp Gly Val Asn Asp Ala Pro Ala Leu Lys Lys Ala Asp
                595                 600                 605

Ile Gly Ile Ala Val Ala Asp Ser Thr Asp Ala Ala Arg Ser Ala Ser
                610                 615                 620

Asp Ile Val Leu Thr Glu Pro Gly Leu Ser Val Ile Val Ser Ala Val
625                 630                 635                 640

Leu Thr Ser Arg Ala Ile Phe Gln Arg Met Lys Asn Tyr Thr Ile Tyr
                645                 650                 655

Ala Val Ser Ile Thr Ile Arg Ile Val Leu Gly Phe Val Leu Leu Ala
                660                 665                 670

Leu Ile Trp Glu Tyr Asp Phe Pro Pro Phe Met Val Leu Ile Ile Ala
                675                 680                 685

Ile Leu Asn Asp Gly Thr Ile Met Thr Ile Ser Gln Asp Arg Val Lys
                690                 695                 700

Pro Ser Pro Lys Pro Asp Ser Trp Lys Leu Asn Glu Ile Phe Ala Thr
705                 710                 715                 720
```

```
Gly Ile Val Ile Gly Thr Tyr Leu Ala Leu Val Thr Val Leu Phe Tyr
                725                 730                 735

Trp Thr Val Ile Glu Thr Thr Phe Phe Glu Asp Thr Phe Gly Leu Met
            740                 745                 750

Ser Ile Ser Asp Asn Ser Glu Val Ser Ser Ala Val Tyr Leu Gln
        755                 760                 765

Val Ser Ile Ile Ser Gln Ala Leu Ile Phe Val Thr Arg Ser Gln Gly
770                 775                 780

Trp Ser Phe Leu Glu Arg Pro Gly Ala Leu Leu Met Ile Ala Phe Val
785                 790                 795                 800

Val Ala Gln Leu Val Ala Thr Leu Ile Ala Val Tyr Ala Glu Ile Ser
                805                 810                 815

Phe Ala Tyr Ile Ser Gly Ile Gly Trp Gly Trp Ala Gly Val Ile Trp
            820                 825                 830

Leu Tyr Ser Leu Ile Phe Tyr Phe Pro Leu Asp Ile Ile Lys Phe Ala
        835                 840                 845

Ile Arg Tyr Ala Leu Ser Gly Asp Ala Trp Asn Leu Leu Phe Asp Arg
    850                 855                 860

Lys Thr Ala Phe Thr Ala Lys Lys Asp Tyr Gly Lys Glu Asp Arg Ala
865                 870                 875                 880

Ala Lys Trp Val Leu Ser Gln Arg Thr Leu Gln Gly Leu His Asp Met
                885                 890                 895

Glu Phe Lys Ala Gly Arg Thr Ser Pro Lys Asn Ala Gly Trp Ile Ala
            900                 905                 910

Glu Gln Ala Arg Arg Arg Ala Glu Ile Ala Arg Leu Gly Glu Leu His
        915                 920                 925

Thr Met Arg Gly His Val Glu Ser Val Met Arg Leu Lys Asn Leu Asp
    930                 935                 940

Pro Asn Val Ile Ser Ala His Thr Val
945                 950

<210> SEQ ID NO 100
<211> LENGTH: 22
<212> TYPE: DNA
<213> ORGANISM: Rosa hybrida

<400> SEQUENCE: 100
gctaggagtg ctgctgatct tg                                            22

<210> SEQ ID NO 101
<211> LENGTH: 25
<212> TYPE: DNA
<213> ORGANISM: Rosa hybrida

<400> SEQUENCE: 101
ggagccagaa gtttgttata ggagg                                         25

<210> SEQ ID NO 102
<211> LENGTH: 22
<212> TYPE: DNA
<213> ORGANISM: Rosa hybrida

<400> SEQUENCE: 102
cttgttgaca gcaccaacaa tg                                            22

<210> SEQ ID NO 103
<211> LENGTH: 25
<212> TYPE: DNA
```

-continued

```
<213> ORGANISM: Rosa hybrida

<400> SEQUENCE: 103
caaggatcta tcgacactca acttg                                          25

<210> SEQ ID NO 104
<211> LENGTH: 33
<212> TYPE: DNA
<213> ORGANISM: Rosa hybrida

<400> SEQUENCE: 104
gcatgaattc tgcagcgtta tttccgccca cac                                 33

<210> SEQ ID NO 105
<211> LENGTH: 33
<212> TYPE: DNA
<213> ORGANISM: Rosa hybrida

<400> SEQUENCE: 105
gcatgaattc tgcagttatt tccgcccaca cag                                 33

<210> SEQ ID NO 106
<211> LENGTH: 33
<212> TYPE: DNA
<213> ORGANISM: Rosa hybrida

<400> SEQUENCE: 106
gcatgaattc tgcagatttc cgcccacaca gtc                                 33

<210> SEQ ID NO 107
<211> LENGTH: 33
<212> TYPE: DNA
<213> ORGANISM: Rosa hybrida

<400> SEQUENCE: 107
gcatgaattc ttattacaca aaaacagaag gtc                                 33
```